(12) United States Patent
Chiku et al.

(10) Patent No.: US 11,821,896 B2
(45) Date of Patent: *Nov. 21, 2023

(54) KIT AND METHOD FOR MEASURING MEASUREMENT TARGET SUBSTANCE IN BIOLOGICAL SAMPLE

(71) Applicant: FUJIFILM Corporation, Tokyo (JP)

(72) Inventors: Hiroyuki Chiku, Ashigarakami-gun (JP); Kousuke Watanabe, Ashigarakami-gun (JP); Kazuhei Kaneko, Ashigarakami-gun (JP); Kazuhiro Hamada, Ashigarakami-gun (JP); Kouitsu Sasaki, Ashigarakami-gun (JP); Tomoaki Yoshioka, Ashigarakami-gun (JP); Naoyuki Hanaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 390 days.

This patent is subject to a terminal disclaimer.

(21) Appl. No.: 16/585,306

(22) Filed: Sep. 27, 2019

(65) Prior Publication Data
US 2020/0025748 A1    Jan. 23, 2020

Related U.S. Application Data

(63) Continuation of application No. PCT/JP2018/013406, filed on Mar. 29, 2018.

(30) Foreign Application Priority Data

Mar. 30, 2017    (JP) .................... 2017-066921

(51) Int. Cl.
G01N 33/533    (2006.01)
C07D 209/90    (2006.01)
G01N 21/64    (2006.01)

(52) U.S. Cl.
CPC ......... *G01N 33/533* (2013.01); *C07D 209/90* (2013.01); *G01N 21/6428* (2013.01)

(58) Field of Classification Search
CPC ..... C07D 209/90; C07F 5/02; G01N 21/6428; G01N 33/533; G01N 33/543
See application file for complete search history.

(56) References Cited

U.S. PATENT DOCUMENTS

| | | |
|---|---|---|
| 4,680,274 A | 7/1987 | Sakai et al. |
| 5,326,692 A | 7/1994 | Brinkley et al. |
| 5,573,909 A | 11/1996 | Singer et al. |
| 5,670,381 A | 9/1997 | Jou et al. |
| 5,723,218 A | 3/1998 | Haugland et al. |
| 11,136,500 B2 * | 10/2021 | Watanabe .......... C09K 11/0827 |
| 2006/0172357 A1 | 8/2006 | Yang et al. |
| 2009/0261269 A1 | 10/2009 | Horii et al. |
| 2011/0054187 A1 | 3/2011 | Rurack et al. |
| 2014/0295468 A1 | 10/2014 | Kasagi et al. |
| 2015/0051101 A1 | 2/2015 | Hoshino et al. |
| 2015/0171328 A1 | 6/2015 | Bura et al. |
| 2016/0069909 A1 | 3/2016 | Nakamura et al. |
| 2016/0370289 A1 | 12/2016 | Hikage et al. |

(Continued)

FOREIGN PATENT DOCUMENTS

| | | |
|---|---|---|
| CN | 1944540 A | 4/2007 |
| CN | 102174144 A | 9/2011 |

(Continued)

OTHER PUBLICATIONS

Posthuma-Trumpie et al., "Development of a competitive lateral flow immunoassay for progesterone: influence of coating conjugates and buffer components," Anal. Bioanal. Chem., 2008, vol. 392, pp. 1215-1223.*

Office Action dated Jul. 21, 2020, from the Japanese Patent Office in Application No. 2019-510171.

(Continued)

*Primary Examiner* — Galina M. Yakovleva

(74) *Attorney, Agent, or Firm* — Sughrue Mion, PLLC

(57) ABSTRACT

An object of the present invention is to provide a kit and a method which are capable of measuring a measurement target substance in a biological sample with high precision in a measurement range from a low concentration range to a high concentration range. According to the present invention, there is provided a kit for measuring a measurement target substance in a biological sample, including a labeled particle having a first binding substance capable of binding to a measurement target substance in a biological sample, and a substrate having a second binding substance capable of binding to any one of the measurement target substance or the first binding substance, in which the labeled particle is a luminescent labeled particle containing at least one kind of compound represented by Formula (1) and a particle.

(1)

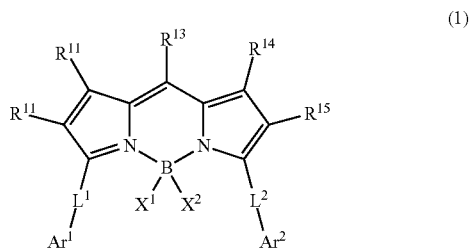

Each symbol in Formula (1) has the meaning described in the present specification.

18 Claims, 4 Drawing Sheets

(56) References Cited

U.S. PATENT DOCUMENTS

| | | | |
|---|---|---|---|
| 2019/0185745 A1 | 6/2019 | Watanabe et al. | |
| 2020/0025748 A1 | 1/2020 | Chiku et al. | |
| 2020/0025771 A1* | 1/2020 | Chiku | G01N 33/543 |
| 2020/0033334 A1* | 1/2020 | Chiku | C07F 5/022 |
| 2020/0378962 A1* | 12/2020 | Chiku | G01N 21/6428 |
| 2021/0364524 A1* | 11/2021 | Kanazawa | G01N 33/543 |
| 2021/0380881 A1 | 12/2021 | Watanabe et al. | |

FOREIGN PATENT DOCUMENTS

| | | |
|---|---|---|
| CN | 105462576 A | 4/2016 |
| CN | 106008581 A | 10/2016 |
| EP | 2 995 952 A1 | 3/2016 |
| JP | 60-256057 A | 12/1985 |
| JP | 4-72564 A | 3/1992 |
| JP | 7-508309 A | 9/1995 |
| JP | 8-503547 A | 4/1996 |
| JP | 10-153599 A | 6/1998 |
| JP | 11-337551 A | 12/1999 |
| JP | 2000-206115 A | 7/2000 |
| JP | 2000-221196 A | 8/2000 |
| JP | 2001-021563 A | 1/2001 |
| JP | 3442777 B2 | 9/2003 |
| JP | 2007-127438 A | 5/2007 |
| JP | 2008-527332 A | 7/2008 |
| JP | 2008-190946 A | 8/2008 |
| JP | 2008-249361 A | 10/2008 |
| JP | 2010-19553 A | 1/2010 |
| JP | 2010-112748 A | 5/2010 |
| JP | 2010-190880 A | 9/2010 |
| JP | 2012-47684 A | 3/2012 |
| JP | 2014-235081 A | 12/2014 |
| JP | 2015-072249 A | 4/2015 |
| JP | 2016-057145 A | 4/2016 |
| KR | 10-2014-0137676 A | 12/2014 |
| WO | 92/21769 A1 | 12/1992 |
| WO | 93/23492 A1 | 11/1993 |
| WO | 2013/146694 A1 | 10/2013 |
| WO | 2014/013205 A1 | 1/2014 |
| WO | 2015/129361 A1 | 9/2015 |
| WO | 2017/150516 A1 | 9/2017 |
| WO | 2018/038137 A1 | 3/2018 |
| WO | 2018/038138 A1 | 3/2018 |
| WO | 2018/181796 A1 | 10/2018 |
| WO | 2018/181798 A1 | 10/2018 |
| WO | 2018/181800 A1 | 10/2018 |

OTHER PUBLICATIONS

Mandy Hecht et al., "Fluorinated Boron-Dipyrromethene (BODIPY) Dyes: Bright and Versatile Probes for Surface Analysis", ChemistryOpen, vol. 2, 2013, pp. 25-38.

Olivier Galangau et al., "Rational design of visible and NIR distyryl-BODIPY dyes from a novel fluorinated platform", Organic Biomolecular Chemistry, vol. 8, 2010, pp. 4546-4553.

Junchao Xu et al., "meso-$C_6F_5$ substituted BODIPYs with distinctive spectroscopic properties and their application for bioimaging in living cells", Tetrahedron, vol. 70, 2014, pp. 5800-5805.

International Search Report dated Jun. 26, 2018 from the International Searching Authority in counterpart International Application No. PCT/JP2018/013406.

International Preliminary Report on Patentability dated Oct. 1, 2019 from the International Bureau in counterpart International Application No. PCT/JP2018/013406.

Written Opinion dated Jun. 26, 2018 from the International Bureau in counterpart International Application No. PCT/JP2018/013406.

Extended European Search Report dated Feb. 10, 2020 from the European Patent Office in European Application No. 18774345.5.

Communication dated Feb. 15, 2021, from the European Patent Office in European Application No. 18774345.5.

Office Action dated Jan. 29, 2021, issued by the Korean Intellectual Property Office in Korean Application No. 10-2019-7028398.

Yukie Suda et al., "Multi-thiophene-substituted NIR boron-dibenzopyrromethene dyes: synthesis and their spectral properties", Tetrahedron, vol. 71, Mar. 2015, pp. 4174-4182 (9 Pages Total).

U.S. Appl. No. 16/585,758, Pending.

U.S. Appl. No. 16/585,231, Allowed.

U.S. Appl. No. 16/282,327, U.S. Pat. No. 11,136,500.

U.S. Appl. No. 17/407,146, Pending.

U.S. Appl. No. 16/999,138, Pending.

U.S. Appl. No. 17/393,578, Pending.

Extended European Search Report dated Apr. 11, 2022 from the European Patent Office in European Application No. 20752374.7, corresponding to U.S. Appl. No. 17/393,578.

Office Action dated Mar. 3, 2022 from the China National Intellectual Property Administration in CN Application No. 201780051809.9, corresponding to U.S. Appl. No. 17/407,146.

Office Action dated Apr. 22, 2022 in U.S. Appl. No. 16/585,758.

International Preliminary Report on Patentability dated Oct. 1, 2019, issued by the International Bureau in application No. PCT/JP2018/013408, corresponds to U.S. Appl. No. 16/585,758.

International Search Report dated Jul. 3, 2018, issued by the International Searching Authority in application No. PCT/JP2018/013408, corresponds to U.S. Appl. No. 16/585,758.

Written Opinion dated Jul. 3, 2018, issued by the International Searching Authority in application No. PCT/JP2018/013408, corresponds to U.S. Appl. No. 16/585,758.

Communication dated Feb. 16, 2021, from the European Patent Office in application No. 18775758.8, corresponds to U.S. Appl. No. 16/585,758.

Office Action dated Jan. 14, 2021 issued by the Korean Intellectual Property Office in Korean Application No. 10-2019-7028409, corresponds to U.S. Appl. No. 16/585,758.

Extended European Search Report dated Feb. 10, 2020 from the European Patent Office in Application No. 18775758.8, corresponds to U.S. Appl. No. 16/585,758.

Office Action dated Jul. 21, 2020, from the Japanese Patent Office in Application No. 2019-510173, corresponds to U.S. Appl. No. 16/585,758.

Office Action dated Dec. 7, 2021 in U.S. Appl. No. 16/585,758.

Alina Brzeczek et al., "Systematic elongation of thienyl linkers and their effect on optical and electrochemical properties in Carbazole-BODIPY donor-acceptor systems", RSC Advances, Apr. 2016, pp. 36500-36509.

Huaxia Shi et al., "Tumor-targeting, enzyme-activated nanoparticles for simultaneous cancer diagnosis and photodynamic therapy", Journal of Materials Chemistry B, vol. 4, No. 1, Jan. 1, 2016, pp. 113-120.

International Search Report and Written Opinion dated Oct. 10, 2017 from the International Searching Authority in International Application No. PCT/JP2017/030054, corresponds to U.S. Appl. No. 16/282,327.

International Preliminary Report on Patentability dated Feb. 26, 2019 in International Application No. PCT/JP2017/030054, corresponds to U.S. Appl. No. 16/282,327.

Yan-Wei Wang et al., "Dihydronaphthalene-Fused Boron-Dipyrromethene (BODIPY) Dyes: Insight into the Electronic and Conformational Tuning Modes of BODIPY Fluorophores", Chemistry—A European Journal, vol. 16, No. 9, Feb. 19, 2010, pp. 2887-2903.

Yu Rong et al., "Multicolor Fluorescent Semiconducting Polymer Dots with Narrow Emissions and High Brightness", ACS Nano, Jan. 2, 2013, pp. 376-384.

Yu-Zhe Chen et al., "Water-soluble, membrane-permeable organic fluorescent nanoparticles with large tunability in emission wavelengths and Stokes shifts", Chemical Communications, vol. 49, No. 52, Jan. 1, 2013, pp. 5877-5879.

B. Kucukoz et al., "Enhancement of two photon absorption properties and intersystem crossing by charge transfer in pentaaryl boron-dipyrromethene (BODIPY) derivatives", Physical Chemistry Chemical Physics, vol. 18, No. 19, Apr. 19, 2016.

Lijuan Jiao et al., "Long wavelength ref fluorescent dyes from 3,5-diiodo-BODIPYs", Organic & Biomolecular Chemistry, vol. 8, No. 11, Apr. 14, 2010, pp. 2517-2519.

(56) References Cited

OTHER PUBLICATIONS

Ning Zhao et al., "Stepwise Polychlorination of 8-Chloro-BODIPY and Regioselective Functionalization of 2,3,5,6,8-Pentachloro-BODIPY", The Journal of Organic Chemistry, vol. 80, No. 16, Aug. 21, 2015, pp. 8377-8383.
Zeya Feng et al., "Regioselective and Stepwise Syntheses of Functionalized BODIPY Dyes through Palladium-Catalyzed Cross-Coupling Reactions and Direct C—H Arylations", The Journal of Organic Chemistry, vol. 81, No. 15, Jun. 30, 2016, pp. 6281-6291.
Bartelmess et al., "Synthesis and Characterization of Far-Red/NIR-Fluoroescent BODIPY Dyes, Solid-State Fluorescence and Application as Fluorescent Tags Attached to Carbon Nano-onions", Chem. Eu. J., 2015, vol. 21, pp. 9727-9732.
Cesar F. A. Gomez-Duran et al., "Near-IR BODIPY Dyes a la Carte-Programmed Orthogonal Functionalization of Rationally Designed Building Blocks", Chemistry—A European Journal, vol. 22, No. 3, Nov. 26, 2015, pp. 1048-1061.
Lyubov N. Sobenina et al., "Synthesis and Optical Properties of Difluorobora-s-diazaindacene Dyes with Trifluoromethyl Substituents", European Journal of Organic Chemistry, vol. 2013, No. 19, May 10, 2013, pp. 4107-4118.
Office Action of Europe Application 17843616.8 dated Nov. 19, 2020, corresponds to U.S. Appl. No. 16/282,327.
Office Action of Japan Application 2018-535725 dated Jan. 7, 2020, corresponds to U.S. Appl. No. 16/282,327.
Office Action of Korean Application 10-2019-7005239, dated Jul. 15, 2020, corresponds to U.S. Appl. No. 16/282,327.
Search Report of Europe Application No. 17843616.8, dated Jun. 14, 2019, corresponds to U.S. Appl. No. 16/282,327.
Shilei Zhu et al., "Highly water-soluble neutral near-infrared emissive BODIPY polymeric dyes", Journals of Materials Chemistry, vol. 22, Dec. 2011, pp. 271-2790.
Communication dated Feb. 15, 2021, from the European Patent Office in European Application No. 18774346.3, corresponds to U.S. Appl. No. 16/585,231.
Office Action dated Jul. 21, 2020, from the Japanese Patent Office in application No. 2019-510175, corresponds to U.S. Appl. No. 16/585,231.
Extended European Search Report dated Feb. 10, 2020 from European Patent Office in EP Application No. 18774346.3, corresponds to U.S. Appl. No. 16/585,231.
International Preliminary Report on Patentability dated Sep. 3, 2020, issued by the International Searching Authority in application No. PCT/JP2019/006705, corresponds to U.S. Appl. No. 16/999,138.
International Preliminary Report on Patentability with Translation of Written Opinion dated Oct. 1, 2019, in International Application No. PCT/JP2018/013410, corresponds to U.S. Appl. No. 16/585,231.
International Search Report and Written Opinion dated May 21, 2019, issued by the International Searching Authority in application No. PCT/JP2019/006705, corresponds to U.S. Appl. No. 16/999,138.
International Search Report dated Jun. 26, 2018 ,in International Application No. PCT/JP2018/013410, corresponds to U.S. Appl. No. 16/585,231.
O. Galanagau et al., "Electrochromic and electrofluorochromic properties of a new boron dipyrromethene-ferrocene conjugate", Electrochimica Acta, vol. 87, Dec. 2013, pp. 809-815.
Office Action dated Feb. 8, 2021 in U.S. Appl. No. 16/282,327.
Office Action of China Application 201780051809.9, dated May 31, 2021, corresponds to U.S. Appl. No. 16/282,327.
Office Action of Korean Application 10-2019-7005239, dated Jan. 12, 2021, corresponds to U.S. Appl. No. 16/282,327.
Wenbo Hu et al., "Engineering Lysosome—Targeting BODIPY Nanoparticles for Photoacoustic Imaging and Photodynamic Therapy and Near-Infrared Light", ACS Appl Mater Interfaces, Apr. 2016, pp. 12039-12047.

Written Opinion of the International Searching Authority dated Jun. 26, 2018, in International Application No. PCT/JP2018/013410, corresponds to U.S. Appl. No. 16/585,231.
Extended European Search Report dated Mar. 19, 2021 from the European Patent Office in Application No. 19756950.2, corresponding to U.S. Appl. No. 16/999,138.
International Preliminary Report on Patentability dated Feb. 22, 2021, issued by the International Searching Authority in application No. PCT/JP2020/004222, corresponds to U.S. Appl. No. 17/393,578.
International Search Report dated Apr. 21, 2020, issued by the International Searching Authority in application No. PCT/JP2020/004222, corresponds to U.S. Appl. No. 17/393,578.
Nagai et al., "Aromatic Ring-Fused BODIPY-Based Conjugated Polymers Exhibiting Narrow Near-Infrared Emission Bands", Macromolecules, vol. 43, No. 1, 2010, pp. 193-200.
Office Action dated Apr. 13, 2021 in Japanese Application No. 2019-501053, corresponds to U.S. Appl. No. 16/999,138.
Wild, "Logit-Log and Hour-Parameter Log-Logistic Methods", The Immunoassay Handbook, Third Edition, 2005, pp. 238-240 (4 pages total).
Office Action dated Apr. 25, 2022 in Chinese Application No. 201880022543.X, corresponds to U.S. Appl. No. 16/585,231.
Office Action dated May 13, 2022 in Chinese Application No. 201880022538.9, corresponds to U.S. Appl. No. 16/585,758.
Notice of Reasons for Refusal dated Aug. 2, 2022 from the Japanese Patent Office in Japanese Application No. 2020-571226, corresponds to U.S. Appl. No. 17/393,578.
Communication dated Jun. 13, 2022 from the Chinese Patent Office in Chinese Application No. 201780051809.9, corresponds to U.S. Appl. No. 17/407,146.
Office Action dated May 11, 2022 in Chinese Application No. 201880022541.0.
Office Action dated Aug. 5, 2022 from the China National Intellectual Property Administration in CN Application No. 201880022543.X, corresponds to U.S. Appl. No. 16/585,231.
Office Action dated Aug. 26, 2022 in Chinese Application No. 201880022541.0.
Office Action dated Sep. 23, 2022 in U.S. Appl. No. 16/585,758.
Office Action dated Oct. 19, 2022 in U.S. Appl. No. 16/585,231.
Office Action dated Sep. 15, 2022 in Chinese Application No. 201880022538.9, corresponds to U.S. Appl. No. 16/585,758.
Office Action dated Oct. 24, 2022 from the European Patent Office in EP Application No. 19756950.2, corresponds to U.S. Appl. No. 16/999,138.
Office Action dated Jan. 9, 2023 from the Chinese Intellectual Property Administration in CN Application No. 201880022543.X corresponding to U.S. Appl. No. 16/585,231.
Office Action dated Jan. 9, 2023 from the Chinese Intellectual Property Administration in CN Application No. 201880022538.9 corresponding to U.S. Appl. No. 16/585,758.
Office Action dated Dec. 16, 2022 from the Chinese Intellectual Property Administration in CN Application No. 201980014801.4 corresponding to U.S. Appl. No. 16/999,138.
Office Action dated Jan. 24, 2023 from the Japanese Patent Office in JP Application No. 2020-571226 corresponding to U.S. Appl. No. 17/393,578.
Office Action dated Jan. 5, 2023 from the Chinese Intellectual Property Administration in corresponding CN Application No. 201880022541.0.
Office Action dated Apr. 15, 2023 in Chinese Application No. 201980014801.4, corresponding to U.S. Appl. No. 16/999,138.
Notice of Allowance dated Mar. 14, 2023 in U.S. Appl. No. 16/585,758.
European Office Action dated Jun. 12, 2023 issued by European Patent Office in European Application No. 17843616.8.

\* cited by examiner

KIT AND METHOD FOR MEASURING MEASUREMENT TARGET SUBSTANCE IN BIOLOGICAL SAMPLE

CROSS-REFERENCE TO RELATED APPLICATIONS

This application is a Continuation of PCT International Application No. PCT/JP2018/013406 filed on Mar. 29, 2018, which claims priority under 35 U.S.C § 119(a) to Japanese Patent Application No. 2017-066921 filed on Mar. 30, 2017. Each of the above application(s) is hereby expressly incorporated by reference, in its entirety, into the present application.

BACKGROUND OF THE INVENTION

1. Field of the Invention

The present invention relates to a kit for measuring a measurement target substance in a biological sample, and a method for measuring a measurement target substance in a biological sample.

2. Description of the Related Art

A fluorescence detection method is widely used as a highly sensitive and easy measurement method for quantifying a protein, an enzyme, an inorganic compound, or the like. The fluorescence detection method is a method for confirming the presence of a measurement target substance by detecting the fluorescence emitted in the case where excitation light of a specific wavelength is applied to a sample considered to contain a measurement target substance which is excited by the light of a specific wavelength to emit fluorescence. In the case where the measurement target substance is not a phosphor, for example, the presence of the measurement target substance can be confirmed by bring a substance in which a substance specifically binding to the measurement target substance is labeled with a fluorescent dye into contact with a sample, and then detecting the fluorescence emitted in the case where excitation light is applied in the same manner as described above.

In the fluorescence detection method as described above, there is known a method for utilizing the effect of electric field enhancement by plasmon resonance to improve sensitivity for detecting a measurement target substance present in a small amount. In this method, in order to generate plasmon resonance, a sensor chip having a metal layer in a predetermined area on a transparent support is prepared, and excitation light is incident from a surface side of the support opposite to a surface on which metal layer is formed, with respect to an interface between the support and the metal film, at a predetermined angle equal to or more than the total reflection angle. The surface plasmon is generated in the metal layer by the irradiation with the excitation light, and the signal/noise ratio (S/N ratio) is improved by fluorescence enhancement, which is induced by the electric field enhancement effect caused by generation of the surface plasmon, and thus high-sensitive measurement can be achieved. The fluorescence detection method by surface plasmon excitation (hereinafter referred to as "SPF method") is about 10 times stronger in a signal enhancement degree than the fluorescence detection method by epi-excitation (also referred to as epi-fluorescence method), and thus high-sensitive measurement can be achieved.

JP3442777B discloses fluorescent microparticles produced by blending an initial donor dye having a preferable excitation peak and a final receptor dye having a preferable luminescence peak in polymer microparticles. In JP3442777B, it is described that a polyazaindacene dye is used as the dye.

Olivier Galangau et al., Org. Biomol. Chem., 2010, Vol. 8, pp. 4546 to 4553 discloses that a novel distyryl BODIPY® (registered trademark, abbreviation of boron-dipyrromethene) dye is designed and synthesized, and the synthesized distyryl BODIPY® dye has been analyzed for absorption and emission spectra in a chloromethane solution.

SUMMARY OF THE INVENTION

As described above, although the SPF method is known as a method capable of high-sensitive measurement by a simple measurement method, the SPF method is not sufficiently satisfactory for the measurement of a very small amount of a measurement target substance. Among the detection methods, in a competition method for measuring small molecules that cannot be sandwiched by antibodies, it has been necessary to reduce the amount of particle in the reaction system in order to raise the detection sensitivity, but in such a case, there has remained a problem that measurement in a high concentration range cannot be achieved with high precision due to the lack of fluorescence intensity. The fluorescent microparticles described in JP3442777B have a preferable effective Stokes shift, but have a problem of low quantum yield. In Olivier Galangau et al., Org. Biomol. Chem., 2010, Vol. 8, pp. 4546 to 4553, absorption and emission spectra of a dye solution are analyzed, but there is no description about incorporation of a dye into particles.

The object of the present invention is to provide a kit and a method capable of achieving high-precision measurement of a measurement target substance in a biological sample in a wide concentration range from a low concentration to a high concentration.

As a result of intensive studies to achieve the above object, the present inventors have found that, in a kit including a labeled particle having a first binding substance capable of binding to a measurement target substance and a substrate having a second binding substance capable of binding to any one of the measurement target substance or the first binding substance, by using a labeled particle having an emission maximum wavelength in a long wavelength range of 680 nm or longer and exhibiting a high quantum yield as the labeled particle, the object can be achieved. The present invention has been completed based on these findings. That is, according to the present invention, the following inventions are provided.

<1> A kit for measuring a measurement target substance in a biological sample, comprising: a labeled particle having a first binding substance capable of binding to a measurement target substance in a biological sample; and a substrate having a second binding substance capable of binding to any one of the measurement target substance or the first binding substance, in which the labeled particle is a luminescent labeled particle containing at least one kind of compound represented by Formula (1) and a particle.

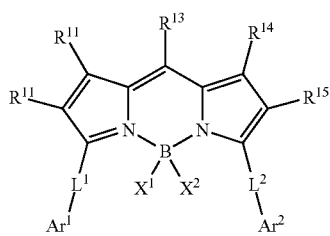
(1)

In the formulae, $R^{11}$ to $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent, and at least three of $R^{11}$, . . . , or $R^{15}$ represent atoms or groups other than hydrogen atoms. $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring. $Ar^1$ and $Ar^2$ each independently represent an aryl group or a heterocyclic group, each of which may have a substituent. $L^1$ and $L^2$ each independently represent any one of Formulae (L-1) to (L-4).

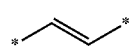
Formula (L-1)

Formula (L-2)

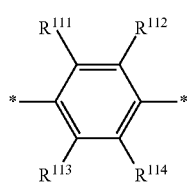
Formula (L-3)

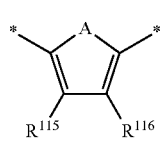
Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

<2> The kit according to <1>, in which the labeled particle is a labeled latex particle.

<3> The kit according to <1> or <2>, in which the labeled particle has a carboxyl group.

<4> The kit according to any one of <1> to <3>, in which an average particle size of the labeled particle is 70 to 500 nm.

<5> The kit according to any one of <1> to <4>, in which the compound represented by Formula (1) is a compound represented by Formula (3).

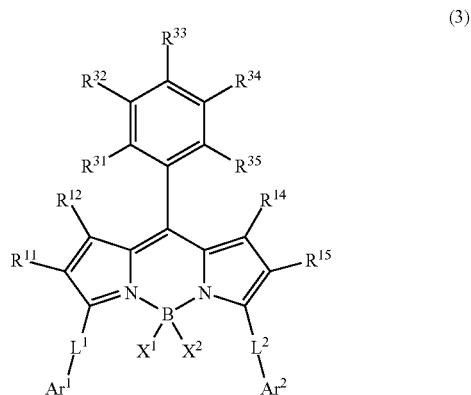
(3)

In the formula, $R^{11}$, $R^{12}$, $R^{14}$, $R^{15}$, $X^1$, $X^2$, $Ar^1$, $Ar^2$, $L^1$, and $L^2$ are as defined in Formula (1), provided that at least two of $R^{11}$, $R^{12}$, $R^{14}$, or $R^{15}$ are atoms or groups other than hydrogen atoms. $R^{31}$ to $R^{35}$ each independently represent a hydrogen atom, a halogen atom, an alkyl group, an aryl group, a heterocyclic group, an ethenyl group, an ethynyl group, an amino group, an acyl group, a cyano group, an alkoxy group, an aryloxy group, an alkylthio group, or an arylthio group, each of which may have a substituent, and any one of $R^{31}$, $R^{32}$, $R^{34}$, or $R^{35}$ is a group consisting of two or more atoms.

<6> The kit according to any one of <1> to <4>, in which the compound represented by Formula (1) is a compound represented by Formula (4).

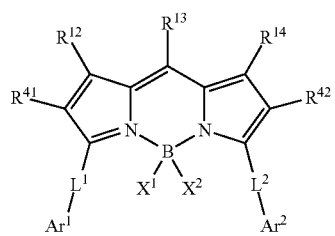
(4)

In the formula, $R^{12}$, $R^{13}$, $R^{14}$, $X^1$, $X^2$, $Ar^1$, $Ar^2$, $L^1$, and $L^2$ are as defined in Formula (1), provided that at least one of $R^{12}$, $R^{13}$, or $R^{14}$ is an atom or group other than a hydrogen atom. $R^{41}$ and $R^{42}$ each independently represent an aryl group, a heterocyclic group, an ethenyl group, or an ethynyl group, each of which may have a substituent.

<7> The kit according to any one of <1> to <4>, in which the compound represented by Formula (1) is a compound represented by Formula (5).

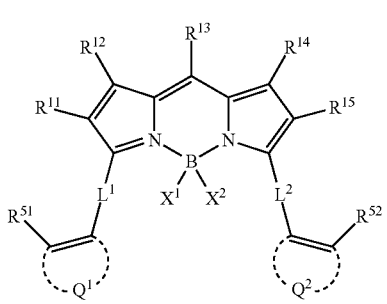

(5)

In the formula, $R^{11}$ to $R^{15}$, $X^1$, $X^2$, $L^1$, and $L^2$ are as defined in Formula (1). $R^{51}$ and $R^{52}$ each independently represent an alkyl group, an aryl group, a heteroaryl group, an amino group, an acyl group, an alkoxy group, an aryloxy group, an alkylthio group, or an arylthio group, each of which may have a substituent. $Q^1$ and $Q^2$ each independently represent an aromatic hydrocarbon ring or an aromatic heterocyclic ring, each of which may have a substituent.

<8> The kit according to any one of <1> to <7>, in which the labeled particle is a luminescent particle containing at least one kind of energy donor compound, at least one kind of energy acceptor compound, and a particle, and at least one kind of the energy donor compound or the energy acceptor compound is the compound represented by Formula (1).

<9> The kit according to <8>, in which at least one kind of compound represented by Formula (1) is contained as the energy donor compound, and at least one kind of compound represented by Formula (1) is contained as the energy acceptor compound.

<10> The kit according to <8> or <9>, in which a molar ratio of the energy donor compound to the energy acceptor compound is 1:10 to 10:1.

<11> The kit according to any one of <8> to <10>, in which a Stokes shift between the energy donor compound and the energy acceptor compound is 40 nm or more.

<12> The kit according to any one of <1> to <11>, in which the substrate includes a detection area having the second binding substance.

<13> The kit according to <12>, in which the detection area is a metal film containing gold.

<14> A method for measuring a measurement target substance in a biological sample, the method comprising: a reaction step of reacting a biological sample with a labeled particle having a first binding substance capable of binding to a measurement target substance; a capturing step of capturing the labeled particle on a substrate having a second binding substance capable of binding to any one of the measurement target substance or the first binding substance by bringing a reaction product obtained in the reaction step into contact with the substrate; and a label information acquisition step of acquiring label information related to the measurement target substance, in which the labeled particle is a luminescent labeled particle containing at least one kind of compound represented by Formula (1) and a particle.

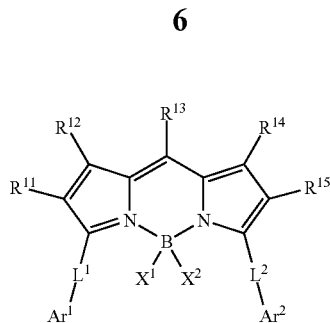

(1)

In the formula, $R^{11}$ to $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent, and at least three of $R^{11}, \ldots,$ or $R^{15}$ represent atoms or groups other than hydrogen atoms. $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring. $Ar^1$ and $Ar^2$ each independently represent an aryl group or a heterocyclic group, each of which may have a substituent. $L^1$ and $L^2$ each independently represent any one of Formulae (L-1) to (L-4).

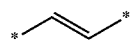

Formula (L-1)

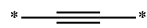

Formula (L-2)

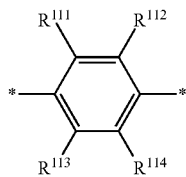

Formula (L-3)

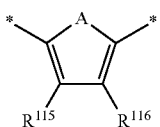

Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

<15> The method according to <14>, in which the particle is a latex particle.

<16> The method according to <14> or <15>, in which the particle has a carboxyl group.

<17> The method according to any one of <14> to <16>, in which an average particle size of the labeled particle is 70 to 500 nm.

<18> The method according to any one of <14> to <17>, in which the compound represented by Formula (1) is a compound represented by Formula (3).

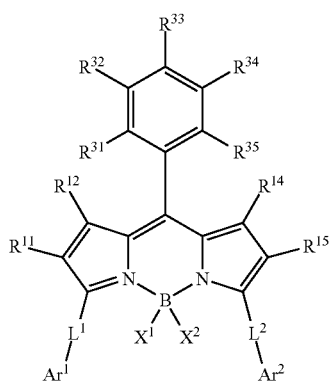

(3)

In the formula, $R^{11}$, $R^{12}$, $R^{14}$, $R^{15}$, $X^1$, $X^2$, $Ar^1$, $Ar^2$, $L^1$, and $L^2$ are as defined in Formula (1), provided that at least two of $R^{11}$, $R^{12}$, $R^{14}$, or $R^{15}$ are atoms or groups other than hydrogen atoms. $R^{31}$ to $R^{35}$ each independently represent a hydrogen atom, a halogen atom, an alkyl group, an aryl group, a heterocyclic group, an ethenyl group, an ethynyl group, an amino group, an acyl group, a cyano group, an alkoxy group, an aryloxy group, an alkylthio group, or an arylthio group, each of which may have a substituent, and any one of $R^{31}$, $R^{32}$, $R^{34}$, or $R^{35}$ is a group consisting of two or more atoms.

<19> The method according to any one of <14> to <17>, in which the compound represented by Formula (1) is a compound represented by Formula (4).

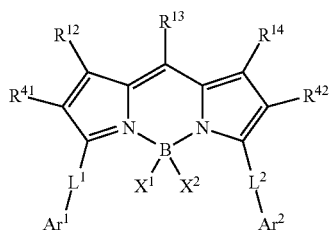

(4)

In the formula, $R^{12}$, $R^{13}$, $R^{14}$, $X^1$, $X^2$, $Ar^1$, $Ar^2$, $L^1$, and $L^2$ are as defined in Formula (1), provided that at least one of $R^{12}$, $R^{13}$, or $R^{14}$ is an atom or group other than a hydrogen atom. $R^{41}$ and $R^{42}$ each independently represent an aryl group, a heterocyclic group, an ethenyl group, or an ethynyl group, each of which may have a substituent.

<20> The method according to any one of <14> to <17>, in which the compound represented by Formula (1) is a compound represented by Formula (5).

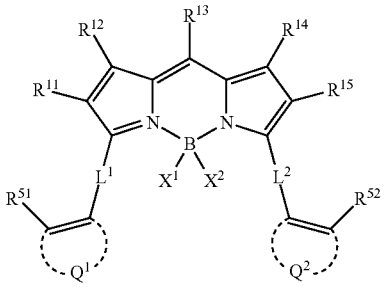

(5)

In the formula, $R^{11}$ to $R^{15}$, $X^1$, $X^2$, $L^1$, and $L^2$ are as defined in Formula (1). $R^{51}$ and $R^{52}$ each independently represent an alkyl group, an aryl group, a heteroaryl group, an amino group, an acyl group, an alkoxy group, an aryloxy group, an alkylthio group, or an arylthio group, each of which may have a substituent. $Q^1$ and $Q^2$ each independently represent an aromatic hydrocarbon ring or an aromatic heterocyclic ring, each of which may have a substituent.

<21> The method according to any one of <14> to <20>, in which the labeled particle is a luminescent particle containing at least one kind of energy donor compound, at least one kind of energy acceptor compound, and a particle, and at least one kind of the energy donor compound or the energy acceptor compound is the compound represented by Formula (1).

<22> The method according to <21>, in which at least one kind of compound represented by Formula (1) is contained as the energy donor compound, and at least one kind of compound represented by Formula (1) is contained as the energy acceptor compound.

<23> The method according to <21> or <22>, in which a molar ratio of the energy donor compound to the energy acceptor compound is 1:10 to 10:1.

<24> The method according to any one of <21> to <23>, in which a Stokes shift between the energy donor compound and the energy acceptor compound is 40 nm or more.

<25> The method according to any one of <14> to <24>, in which the substrate includes a detection area having the second binding substance.

<26> The method according to <25>, in which the detection area is a metal film containing gold.

<27> The method according to <26>, in which label information related to the measurement target substance is acquired by fluorescence detection due to surface plasmon excitation.

According to the kit and the method of the present invention, it is possible to achieve high-precision measurement of a measurement target substance in a biological sample in a wide concentration range from a low concentration to a high concentration.

DESCRIPTION OF THE PREFERRED EMBODIMENTS

Figure 1:
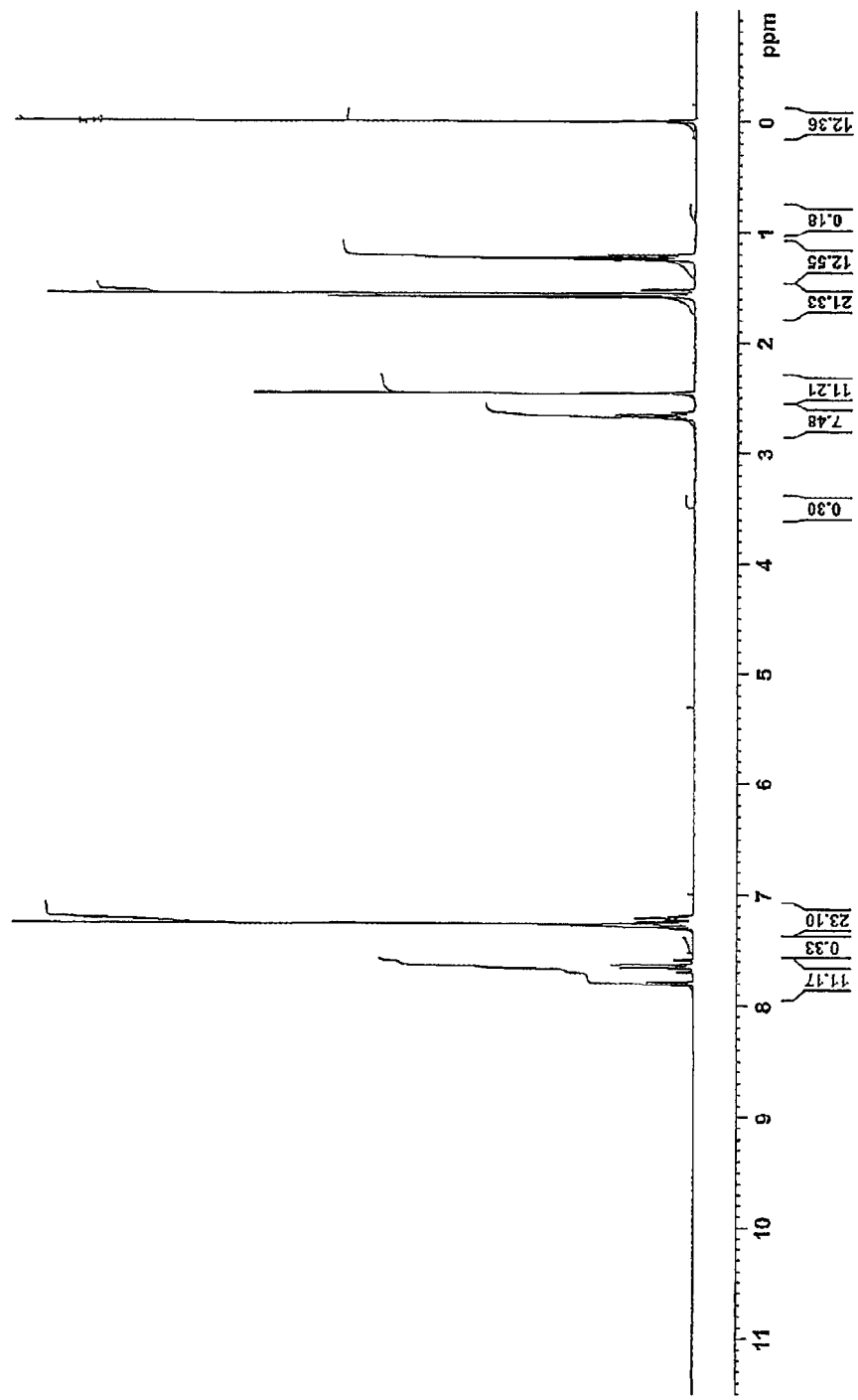
FIG. 1 shows a 400 MHz $^1$H NMR spectrum of Compound (4).

Hereinafter, embodiments of the present invention will be described in detail. In the present specification, the numerical range indicated by using "to" means a range including numerical values described before and after "to" as a minimum value and a maximum value, respectively.

[Kit for Measuring Measurement Target Substance in Biological Sample]

A kit for measuring a measurement target substance in a biological sample according to the embodiment of the present invention includes a labeled particle having a first binding substance capable of binding to a measurement target substance in a biological sample, and a substrate having a second binding substance capable of binding to any one of the measurement target substance or the first binding substance, in which the labeled particle is a luminescent labeled particle containing at least one kind of compound represented by Formula (1) and a particle.

(Biological Sample)

The biological sample is not particularly limited as long as the sample is a sample that may contain the measurement target substance. For example, biologic samples, particularly body fluids (for example, blood, serums, plasma, spinal fluid, tears, sweat, urine, pus, runny nose, or sputum) or excrements (for example, feces), organs, tissues, mucous membranes, skin, or the like of animals (for example, humans, dogs, cats, horses, or the like) can be mentioned.

(Measurement Target Substance)

The measurement target substance is not particularly limited. For example, thyroxine (T4), triiodothyronine (T3), estradiol (E2), aldosterone, symmetrical dimethyl arginine (SDMA), bile acid, cortisol, cholesterol, corticosterone, progesterone, testosterone, estrogen, vitamins, creatinine, amino acids, β-carotene, creatinine, digoxin, theophylline, folic acid, proteins such as inflammatory markers and sepsis markers, or the like can be mentioned.

Progesterone is a sex hormone that is secreted from ovaries and placenta and is involved in luteal function and pregnancy. Progesterone is used to diagnose menstrual cycle abnormality and infertility. Progesterone is also used to check the mating timing of dogs and ovarian remnants of cats.

(First Binding Substance)

The first binding substance used in the present invention is a substance capable of binding to the measurement target substance. As the first binding substance, an antigen, an antibody, or a complex thereof can be used, but the first binding substance is not limited thereto. Preferably, the first binding substance is an antibody. In the case where the first binding substance is an antibody, as antibodies capable of binding to the measurement target substance, for example, an antiserum prepared from a serum of an animal immunized with the measurement target substance, an immunoglobulin fraction purified from the antiserum, a monoclonal antibody obtained by cell fusion using spleen cells of an animal immunized with the measurement target substance, or a fragment thereof [for example, F(ab')$_2$, Fab, Fab', or Fv] can be used. Preparation of these antibodies can be performed by a conventional method. Furthermore, the antibody may be modified as in the case of a chimeric antibody or the like, or a commercially available antibody or an antibody prepared from an animal serum or culture supernatant by known methods can be used.

For example, in the case where the measurement target substance is progesterone, an anti-progesterone antibody capable of binding to progesterone (preferably, specifically recognizing progesterone) is used as the first binding substance.

A method for preparing an anti-progesterone antibody is described below as an example.

A progesterone-BSA conjugate can be prepared by mixing progesterone, bovine serum albumin (hereinafter referred to as BSA), and a condensing agent. Using the conjugate as a mouse immunization antigen, mice are subcutaneously immunized at the back several times. In this case, complete Freund's adjuvant (CFA) and/or incomplete Freund's adjuvant (IFA) can be appropriately selected and then used as a mixture with the immunization antigen. The complete Freund's adjuvant is a substance that stimulates immunity and is a mixture of paraffin and ARLACEL. The incomplete Freund's adjuvant is an adjuvant in which dead mycobacteria or dead bacteria of *Mycobacterium tuberculosis* are added to the complete Freund's adjuvant to further enhance the antigenicity. After several immunizations are performed as appropriate for several weeks, a blood sample is collected from the mice and antibody titers are measured. The antigen is administered intraperitoneally in the case where a sufficient rise in the antibody titers is observed, and the spleen is isolated several days later. By fusing the spleen cells isolated from the immunized mice with mutant myeloma cells (myeloma), it is possible to prepare fused cells having an antibody-producing ability. Only antibody-producing cells against a target antigen are selected from the fused cells, and limiting dilution is performed to proliferate only the cell line. Culture (cloning) of the cells after dilution can be performed. The fusion cell line thus obtained is injected into the abdominal cavity of a mouse, monoclonal antibodies can be produced in ascites fluid by proliferating ascites-type antibody-producing cells, and thus a target antibody can be obtained by recovering these antibodies.

(Labeled particle)

The labeled particle used in the present invention is a luminescent labeled particle containing at least one kind of compound represented by Formula (1) and a particle, and is also referred to as a fluorescent labeled particle.

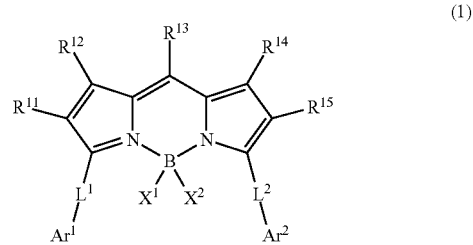

(1)

The meaning of each symbol in Formula (1) is as defined in the present specification.

It is known that an ordinary dye compound is influenced by association in the case where the amount of incorporation into particles is increased, and thus the quantum yield decreases (this is also referred to as concentration quenching). In particular, in the case of being incorporated into particles, a fluorescent dye compound having a long absorption wavelength of 650 nm or longer tends to exhibit concentration quenching, whereby it is difficult to maintain a quantum yield.

Inclusion of a conjugated substituent in the compound represented by Formula (1) used in the present invention makes it possible to emit light of long wavelength and inclusion of a plurality of substituents in the dipyrromethene skeleton makes it also possible to suppress a decrease in the quantum yield in the polymer particle. As a factor of suppressing a decrease in the quantum yield, suppression of intermolecular interaction (for example, π-π interaction) by a plurality of substituents projecting in a direction perpendicular to the dipyrromethene skeleton is considered. According to the compound represented by Formula (1), it is possible to produce a luminescent labeled particle (preferably a fluorescent particle, and more preferably a fluorescent nanoparticle) having high luminance, particularly in the long wavelength range. In the case where the labeled particle is a fluorescent particle, the luminance is the fluorescence intensity. According to the present invention, since the luminescence quantum yield is high in the region of the window of the living body (in the vicinity of 650 to 900 nm which is a near-infrared wavelength range which is easy to transmit through the living body), the sensitivity of sensing using luminescence can be improved.

In the present specification, the alkyl group may be any of linear, branched, cyclic, or a combination thereof, and the number of carbon atoms in the linear or branched alkyl group is preferably 1 to 36, more preferably 1 to 18, still more preferably 1 to 12, and particularly preferably 1 to 6. The cyclic alkyl group may be, for example, a cycloalkyl group having 3 to 8 carbon atoms. Specific examples of the alkyl group include a methyl group, an ethyl group, an n-propyl group, an isopropyl group, an n-butyl group, an iso-butyl group, a sec-butyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, and a cyclohexyl group.

In the present specification, the aryl group is preferably an aryl group having 6 to 48 carbon atoms, more preferably an aryl group having 6 to 24 carbon atoms, and still more preferably an aryl group having 6 to 14 carbon atoms, and examples thereof include a phenyl group, a naphthyl group, an anthryl group, a pyrenyl group, a phenanthrenyl group, a biphenyl group, and a fluorenyl group.

In the present specification, the heterocyclic group is preferably any of 5- to 7-membered substituted or unsubstituted, saturated or unsaturated, aromatic or non-aromatic, or monocyclic or fused heterocyclic groups. The heterocyclic group is preferably a heterocyclic group having a ring-constituting atom selected from a carbon atom, a nitrogen atom, an oxygen atom, and a sulfur atom and having at least one hetero atom selected from a nitrogen atom, an oxygen atom, or a sulfur atom, and more preferably a 5- or 6-membered aromatic heterocyclic group having 3 to 30 carbon atoms. Examples of the heterocyclic group include a furyl group, a benzofuryl group, a dibenzofuryl group, a thienyl group, a benzothienyl group, a dibenzothienyl group, a pyridyl group, a pyrimidinyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a furyl group, a thienyl group, a pyrrolyl group, an indolyl group, an imidazopyridinyl group, and a carbazolyl group.

In the present specification, the acyl group is preferably a linear or branched alkanoyl group having 2 to 15 carbon atoms, and examples thereof include an acetyl group, a propionyl group, a butyryl group, an isobutyryl group, a valeryl group, an isovaleryl group, a pivaloyl group, a hexanoyl group, a heptanoyl group, and a benzoyl group.

In the present specification, the alkoxy group is preferably an alkoxy group having 1 to 20 carbon atoms, and examples thereof include a methoxy group, an ethoxy group, a propoxy group, an n-butoxy group, a pentyloxy group, a hexyloxy group, and a heptyloxy group.

In the present specification, the aryloxy group is preferably an aryloxy group having 6 to 14 carbon atoms, and examples thereof include a phenoxy group, a naphthoxy group, and an anthryloxy group.

The alkylthio group is preferably an alkylthio group having 1 to 30 carbon atoms, and examples thereof include a methylthio group, an ethylthio group, and an n-hexadecylthio group.

The arylthio group is preferably an arylthio group having 6 to 30 carbon atoms, and examples thereof include a phenylthio group, a p-chlorophenylthio group, and an m-methoxyphenylthio group.

In the present specification, examples of the halogen atom include a fluorine atom, a chlorine atom, a bromine atom, and an iodine atom.

In the present specification, examples of the aromatic ring include aromatic hydrocarbon rings such as a benzene ring, a naphthalene ring, an anthracene ring, a phenanthrene ring, a pyrene ring, a perylene ring, and a terylene ring; aromatic heterocyclic rings such as an indene ring, an azulene ring, a pyridine ring, a pyrazine ring, a pyrimidine ring, a pyrazole ring, a pyrazolidine ring, a thiazolidine ring, an oxazolidine ring, a pyran ring, a chromene ring, a pyrrole ring, a pyrrolidine ring, a benzimidazole ring, an imidazoline ring, an imidazolidine ring, an imidazole ring, a pyrazole ring, a triazole ring, a triazine ring, a diazole ring, an indoline ring, a thiophene ring, a thienothiophene ring, a furan ring, an oxazole ring, an oxadiazole ring, a thiazine ring, a thiazole ring, an indole ring, a benzothiazole ring, a benzothiadiazole ring, a naphthothiazole ring, a benzoxazole ring, a naphthoxazole ring, an indolenine ring, a benzindolenine ring, a pyrazine ring, a quinoline ring, and a quinazoline ring; and fused aromatic rings such as a fluorene ring and a carbazole ring; among which aromatic rings having 5 to 16 carbon atoms (aromatic rings and fused rings containing aromatic rings) are preferable.

In addition, the aromatic ring may have a substituent, and the term "aromatic ring" means both an aromatic ring having a substituent and an aromatic ring having no substituent. As the substituent of the aromatic ring, the substituents described in Substituent group A to be mentioned later can be mentioned.

In the present specification, examples of the amino group include an amino group; an alkyl-substituted amino group such as a mono- or dimethylamino group, a mono- or diethylamino group, or a mono or di(n-propyl)amino group; an amino group substituted with an aromatic residue such as a mono- or diphenylamino group or a mono- or a dinaphthylamino group; an amino group substituted with one alkyl group and one aromatic residue, such as a monoalkylmonophenylamino group; a benzylamino group, an acetylamino group, and a phenylacetylamino group. Here, the aromatic residue means a group in which one hydrogen atom is removed from an aromatic ring, and the aromatic ring is as described above in the present specification.

The alkyl group, aryl group, heterocyclic group, ethenyl group, ethynyl group, amino group, acyl group, alkoxy group, aryloxy group, alkylthio group, or arylthio group represented by $R^{11}$ to $R^{15}$ may have a substituent. Examples of the substituent include the substituents described in Substituent group A below.

Substituent Group A:

a sulfamoyl group, a cyano group, an isocyano group, a thiocyanato group, an isothiocyanato group, a nitro group, a nitrosyl group, a halogen atom, a hydroxy group, an amino group, a mercapto group, an amido group, an alkoxy group, an aryloxy group, an alkylthio group, an arylthio group, a carbamoyl group, an acyl group, an aldehyde group, a carbonyl group, an aryl group, an alkyl group, an alkyl group substituted with a halogen atom, an ethenyl group, an ethynyl group, a silyl group, and a trialkylsilyl group (such as a trimethylsilyl group).

The alkyl group, aryl group, heterocyclic group, hydroxy group, alkoxy group, aryloxy group, alkylthio group, arylthio group, ethenyl group, or ethynyl group represented by $X^1$ and $X^2$ may have a substituent. Examples of the substituent include the substituents described in Substituent group A.

The aryl group or heterocyclic group represented by $Ar^1$ and $Ar^2$ may have a substituent. Examples of the substituent include the substituents described in Substituent group A.

The alkyl group, aryl group, heterocyclic group, ethenyl group, ethynyl group, amino group, acyl group, alkoxy group, aryloxy group, alkylthio group, or arylthio group represented by $R^{111}$ to $R^{116}$ may have a substituent. Examples of the substituent include the substituents described in Substituent group A.

<Compound Represented by Formula (1)>

In Formula (1), $R^{11}$ to $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. At least three of $R^{11}, \ldots$, or $R^{15}$ represent atoms or groups other than hydrogen atoms, preferably at least four of $R^{11}, \ldots$, or $R^{15}$ represent atoms or groups other than hydrogen atoms, and more preferably all of $R^{11}$ to $R^{15}$ represent atoms or groups other than hydrogen atoms.

$R^{11}$ and $R^{15}$ may be the same or different atoms or groups, but are preferably the same atoms or groups. $R^{12}$ and $R^{14}$ may be the same or different atoms or groups, but are preferably the same atoms or groups.

$R^{11}$ and $R^{15}$ preferably represent a hydrogen atom, a halogen atom, an alkyl group, an aryl group, a heterocyclic group, an ethenyl group or an ethynyl group, each of which may have a substituent.

$R^{12}$ and $R^{14}$ preferably represent an alkyl group which may have a substituent.

$R^{13}$ preferably represents an aryl group which may have a substituent.

In Formula (1), $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring.

$X^1$ and $X^2$ preferably represent a halogen atom or an alkoxy group. $X^1$ and $X^2$ are more preferably a fluorine atom, a methoxy group, an ethoxy group, an isopropyloxy group, or a t-butyloxy group, each of which is also preferably substituted with a fluorine atom or an alkoxy group.

In Formula (1), $Ar^1$ and $Ar^2$ each independently represent an aryl group or a heterocyclic group, each of which may have a substituent.

In Formula (1), $L^1$ and $L^2$ each independently represent any one of Formulae (L-1) to (L-4).

Formula (L-1)

Formula (L-2)

Formula (L-3)

Formula (L-4)

In the formulae, $R^{11}$ to $R^{16}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

$L^1$ and $L^2$ preferably represent any one of Formula (L-1) or Formula (L-2).

$R^{111}$ to $R^{116}$ are preferably hydrogen atoms.

<As to Compound Represented by Formula (2)>

A preferred example of the compound represented by Formula (1) is a compound represented by Formula (2).

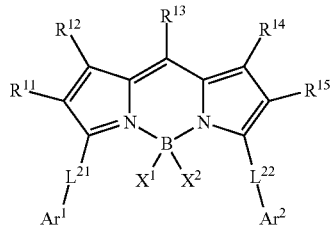

(2)

In the formula, $R^{11}$ to $R^{15}$, $X^1$, $X^2$, $Ar^1$, and $Ar^2$ are as defined in Formula (1), and the preferred ranges thereof are also the same as the preferred ranges in Formula (1). $L^{21}$ and $L^{22}$ each independently represent a group represented by Formula (L-1) or Formula (L-2).

Formula (L-1)

Formula (L-2)

<As to Compound Represented by Formula (3)>
A preferred example of the compound represented by Formula (1) is a compound represented by Formula (3).

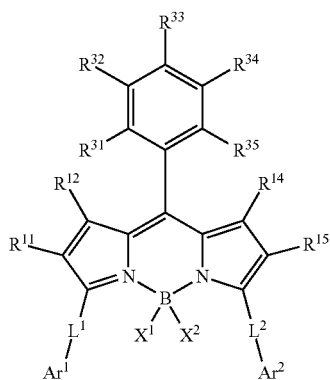

(3)

In Formula (3), $R^{11}$, $R^{12}$, $R^{14}$, $R^{15}$, $X^1$, $X^2$, $Ar^1$, $Ar^2$, $L^1$, and $L^2$ are as defined in Formula (1), and preferred ranges thereof are also the same as the preferred ranges in Formula (1). Provided that at least two of $R^{11}$, $R^{12}$, $R^{14}$, or $R^{15}$ are atoms or groups other than hydrogen atoms, preferably at least three of $R^{11}$, $R^{12}$, $R^{14}$, or $R^{15}$ are atoms or groups other than hydrogen atoms, and more preferably $R^{11}$, $R^{12}$, $R^{14}$, and $R^{15}$ are atoms or groups other than hydrogen atoms.

In Formula (3), $R^{31}$ to $R^{35}$ each independently represent a hydrogen atom, a halogen atom, an alkyl group, an aryl group, a heterocyclic group, an ethenyl group, an ethynyl group, an amino group, a cyano group, an acyl group, an alkoxy group, an aryloxy group, an alkylthio group, or an arylthio group, each of which may have a substituent (examples of the substituent include the substituents described in Substituent group A), and any one of $R^{31}$, $R^{32}$, $R^{34}$, or $R^{35}$ is a group consisting of two or more atoms. The group consisting of two or more atoms is preferably an alkyl group, an aryl group, an ethenyl group, an ethynyl group, an amino group, a cyano group, or an alkoxy group and more preferably an alkyl group. Among the alkyl groups, an alkyl group consisting only of carbon atoms and hydrogen atoms or an alkyl group substituted with a halogen atom is preferable; an alkyl group consisting only of 1 to 6 carbon atoms and hydrogen atoms or an alkyl group substituted with a fluorine atom is more preferable; a methyl group, an isopropyl group, a t-butyl group, or a trifluoromethyl group is still more preferable; and a methyl group is particularly preferable.

<As to Compound Represented by Formula (4)>
A preferred example of the compound represented by Formula (1) is a compound represented by Formula (4).

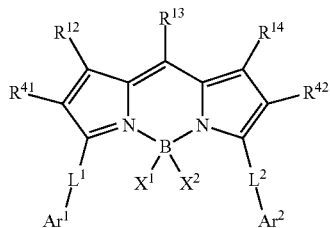

(4)

In Formula (4), $R^{12}$, $R^{13}$, $R^{14}$, $X^1$, $X^2$, $Ar^1$, $Ar^2$, $L^1$, and $L^2$ are as defined in Formula (1), and the preferred ranges thereof are also the same as the preferred ranges in Formula (1). Provided that at least one of $R^{12}$, $R^{13}$, or $R^{14}$ is an atom or group other than a hydrogen atom, preferably at least two of $R^{12}$, $R^{13}$, or $R^{14}$ are atoms or groups other than hydrogen atoms, and more preferably $R^{12}$, $R^{13}$, and $R^{14}$ are atoms or groups other than hydrogen atoms.

In Formula (4), $R^{41}$ and $R^{42}$ each independently represent an aryl group, a heterocyclic group, an ethenyl group, or an ethynyl group, each of which may have a substituent. Examples of the substituent include the substituents described in Substituent group A. $R^{41}$ and $R^{42}$ are each independently preferably an aryl group, an ethenyl group, or an ethynyl group, from the viewpoint of improving a quantum yield, an aryl group is preferable, and from the viewpoint of increasing a wavelength, an ethenyl group or an ethynyl group is preferable. In the case of being an aryl group, it is preferred to have at least one substituent at the ortho or meta position of the aryl group, and it is more preferred to have at least one substituent at the ortho position of the aryl group. The number of the substituent substituting for the aryl group is preferably 1 to 3 and more preferably 2 or 3. The substituent substituting for the aryl group is preferably an alkyl group, more preferably a methyl group, an isopropyl group, or a t-butyl group, and still more preferably a methyl group.

<As to Compound Represented by Formula (5)>
A preferred example of the compound represented by Formula (1) is a compound represented by Formula (5).

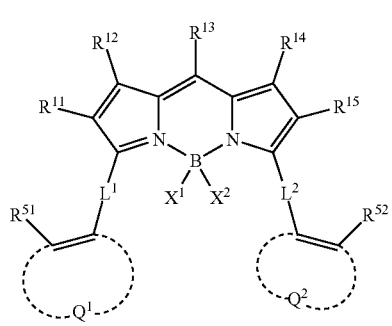

(5)

In Formula (5), $R^{11}$ to $R^{15}$, $X^1$, $X^2$, $L^1$, and $L^2$ are as defined in Formula (1), and the preferred ranges thereof are also the same as the preferred ranges in Formula (1).

In Formula (5), $R^{51}$ and $R^{52}$ each independently represent an alkyl group, an aryl group, a heteroaryl group, an amino group, an acyl group, an alkoxy group, an aryloxy group, an alkylthio group, or an arylthio group, each of which may have a substituent. Examples of the substituent include the substituents described in Substituent group A. $R^{51}$ and $R^{52}$ each independently are preferably an alkyl group or an alkoxy group, and from the viewpoint of improving a quantum yield, more preferably an alkyl group, still more preferably a methyl group, an ethyl group, an isopropyl group, or a t-butyl group, and particularly preferably a methyl group. From the viewpoint of increasing a wavelength, $R^{51}$ and $R^{52}$ each independently are more preferably an alkoxy group, still more preferably a methoxy group, an ethoxy group, an isopropyloxy group, or a t-butyloxy group, and particularly preferably a methoxy group.

$Q^1$ and $Q^2$ each independently represent an aromatic hydrocarbon ring or an aromatic heterocyclic ring, each of which may have a substituent. Examples of the substituent include the substituents described in Substituent group A. $Q^1$ and $Q^2$ are each preferably an aromatic hydrocarbon ring, more preferably a benzene ring, a naphthalene ring, an anthracene ring, a phenanthrene ring, or a pyrene ring, still more preferably a benzene ring or a naphthalene ring, and particularly preferably a benzene ring. As the group containing $R^{51}$ and forming $Q^1$ and the group containing $R^{52}$ and forming $Q^1$, a tolyl group, a xylyl group, or a mesityl group is preferable; a xylyl group or a mesityl group is more preferable; a xylyl group having methyl groups at both ends of the ortho position relative to the bonding position with $L^1$ or $L^2$, or a mesityl group having methyl groups at both ends of the ortho position and at the para position relative to the bonding position with $L^1$ or $L^2$ is still more preferable; and a mesityl group having methyl groups at both ends of the ortho position and at the para position relative to the bonding position with $L^1$ or $L^2$ is particularly preferable.

<As to Compound Represented by Formula (6)>

The compound represented by Formula (5) is more preferably a compound represented by Formula (6).

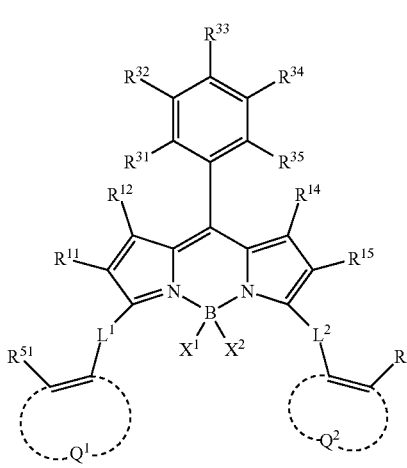

(6)

In the formula, $R^{11}$, $R^{12}$, $R^{14}$, and $R^{15}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent, and at least two of $R^{11}$, $R^{12}$, $R^{14}$, or $R^{15}$ are atoms or groups other than hydrogen atoms. $X^1$ and $X^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $X^1$ and $X^2$ may be linked to each other to form a ring. $R^{31}$ to $R^{35}$ each independently represent a hydrogen atom, a halogen atom, an alkyl group, an aryl group, a heterocyclic group, an ethenyl group, an ethynyl group, an amino group, an acyl group, a cyano group, an alkoxy group, an aryloxy group, an alkylthio group, or an arylthio group, each of which may have a substituent, and any one of $R^{31}$, ..., or $R^{35}$ is a hydrogen atom. $R^{51}$ and $R^{52}$ each independently represent an alkyl group, an aryl group, a heteroaryl group, an amino group, an acyl group, an alkoxy group, an aryloxy group, an alkylthio group, or an arylthio group, each of which may have a substituent. $Q^1$ and $Q^2$ each independently represent an aromatic hydrocarbon ring or an aromatic heterocyclic ring, each of which may have a substituent.

$L^1$ and $L^2$ each independently represent any one of Formulae (L-1) to (L-4).

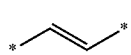

Formula (L-1)

Formula (L-2)

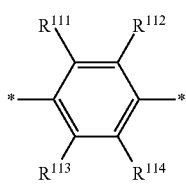

Formula (L-3)

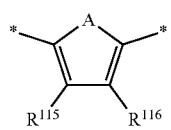

Formula (L-4)

In the formulae, $R^{111}$ to $R^{116}$ each independently represent a hydrogen atom, a halogen atom, an alkyl group, an aryl group, a heterocyclic group, an ethenyl group, an ethynyl group, an amino group, an acyl group, an alkoxy group, an aryloxy group, an alkylthio group, or an arylthio group, each of which may have a substituent. A represents —O—, —S—, or —NH—.

$R^{11}$ and $R^{15}$ are each independently preferably an alkyl group, an aryl group, a heterocyclic group, an ethenyl group, an ethynyl group, or an amino group, more preferably that as defined in $R^{41}$ and $R^{42}$, that is, an aryl group, a heterocyclic group, an ethenyl group, or an ethynyl group, and still more preferably an aryl group, an ethenyl group, or an ethynyl group. From the viewpoint of improving a quantum yield, an aryl group is more preferable, and from the viewpoint of increasing a wavelength, an ethenyl group or an ethynyl group is more preferable. In the case of being an aryl group, it is preferred to have at least one substituent at the ortho or meta position of the aryl group, and it is more preferred to have at least one substituent at the ortho position of the aryl group. The number of the substituent substituting for the aryl group is preferably 1 to 3 and more preferably 2 or 3. The substituent substituting for the aryl group is preferably an alkyl group, more preferably a methyl group, an isopropyl group, or a t-butyl group, and still more preferably a methyl group.

<Specific Examples of Compounds Represented by Formulae (1) to (6)>

Specific examples of the compounds represented by Formulae (1) to (6) are shown below. Me represents a methyl group, Et represents an ethyl group, and iPr represents an isopropyl group.

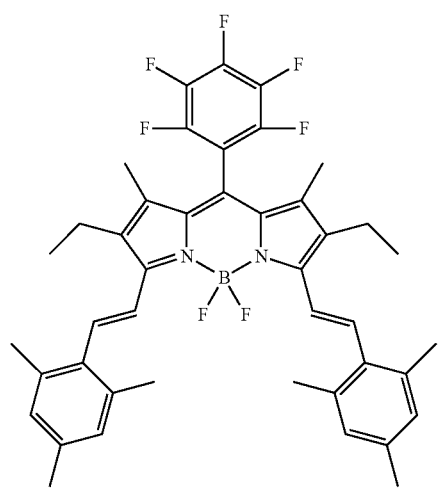
F-1
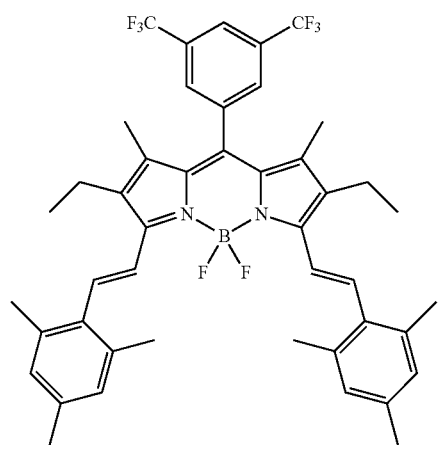
F-2
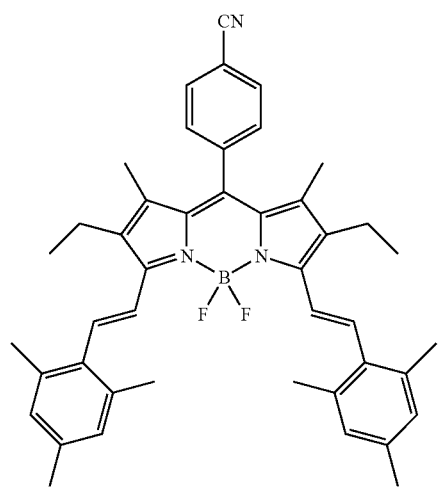
F-3
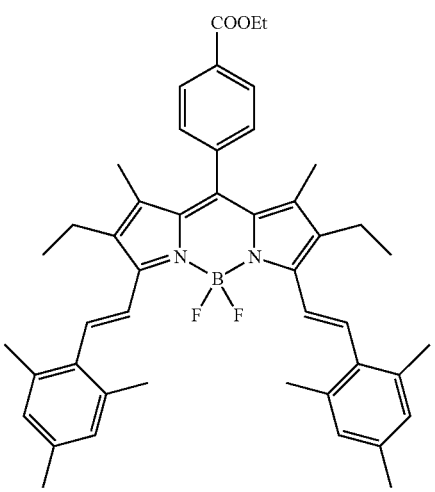
F-4
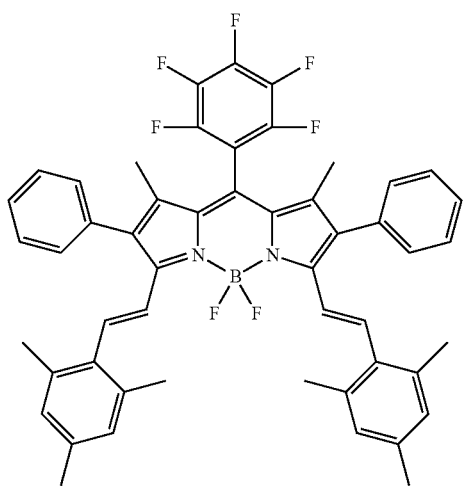
F-5
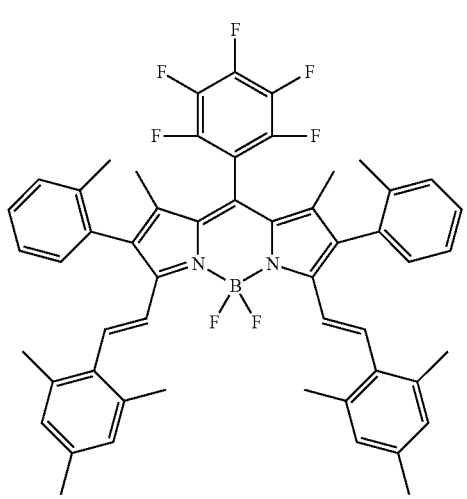
F-6

-continued
F-7
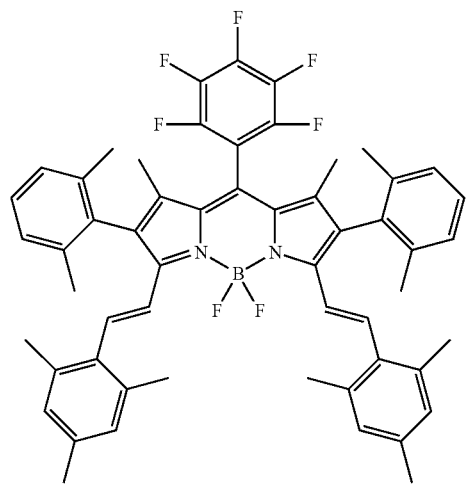
F-8
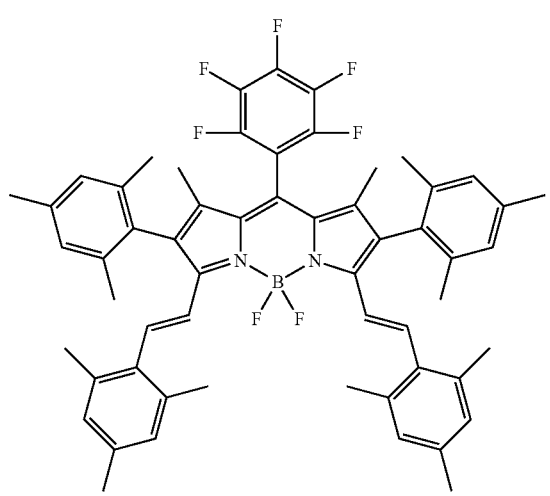
F-9
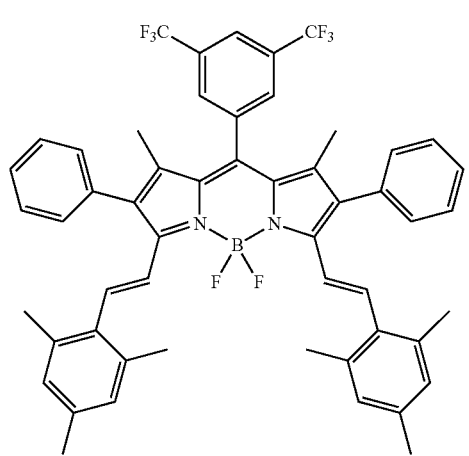
F-10
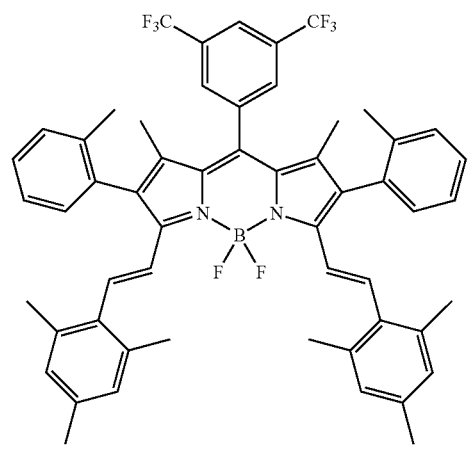
F-11
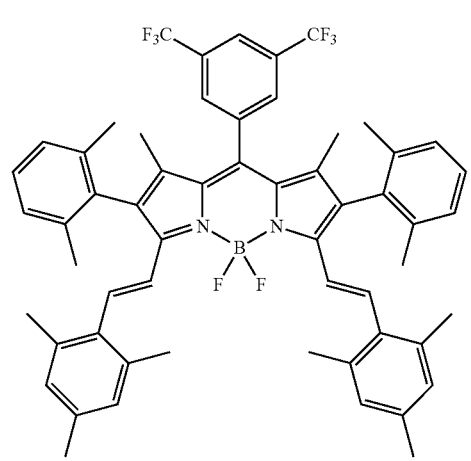
F-12
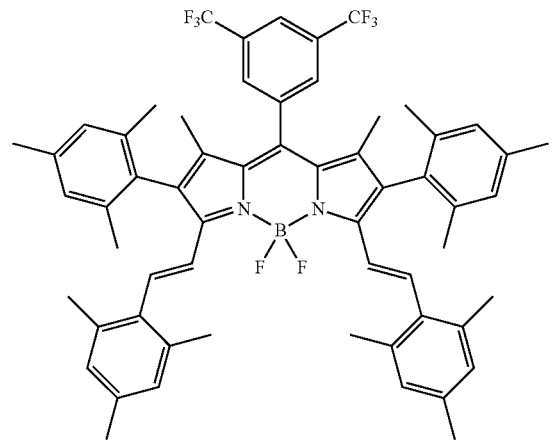

-continued
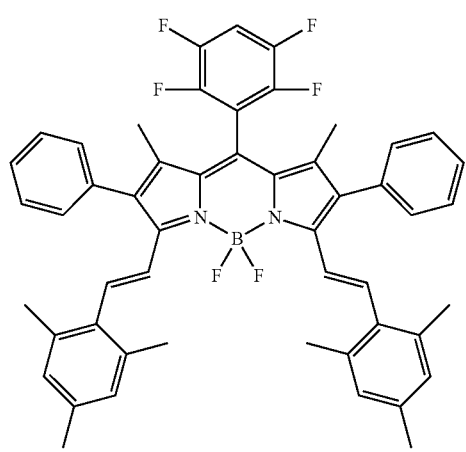
F-13
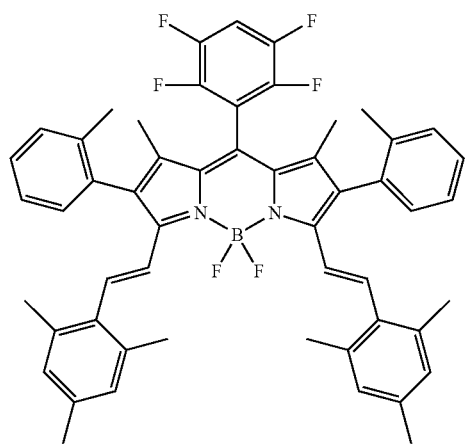
F-14
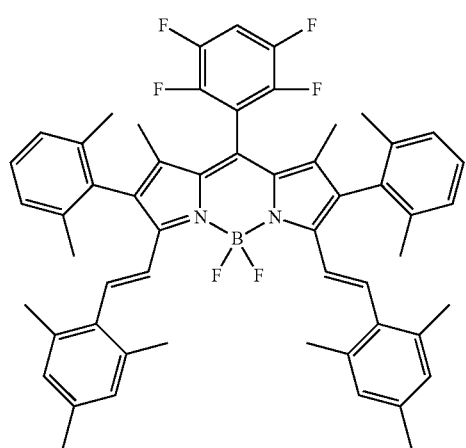
F-15
-continued
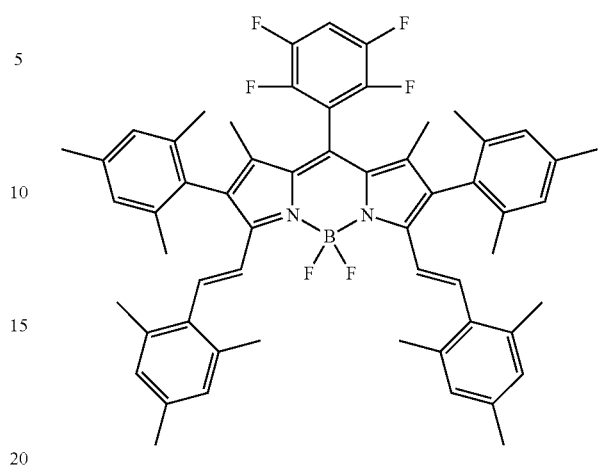
F-16
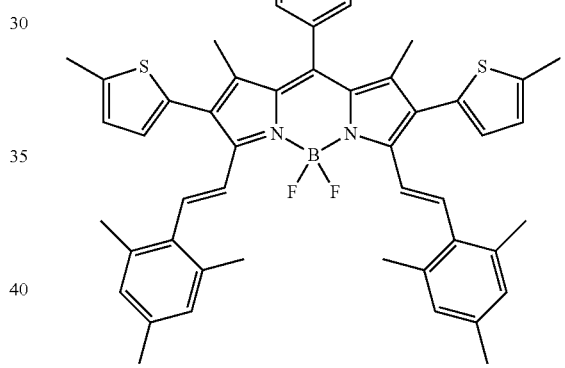
F-17
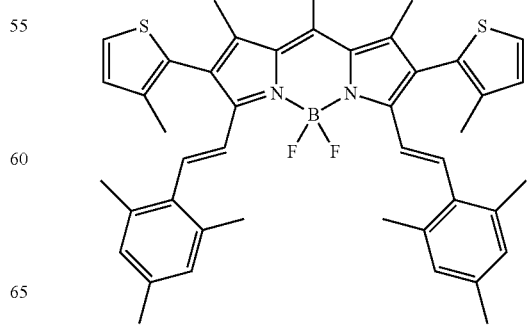
F-18

-continued
F-19
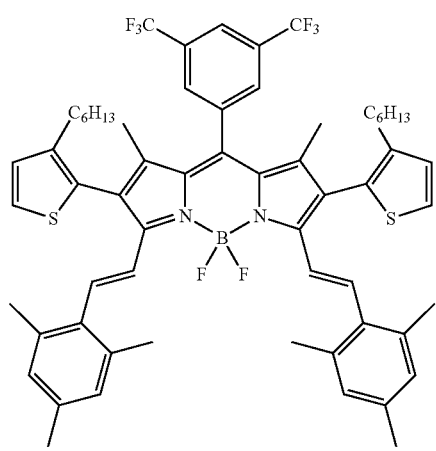
F-20
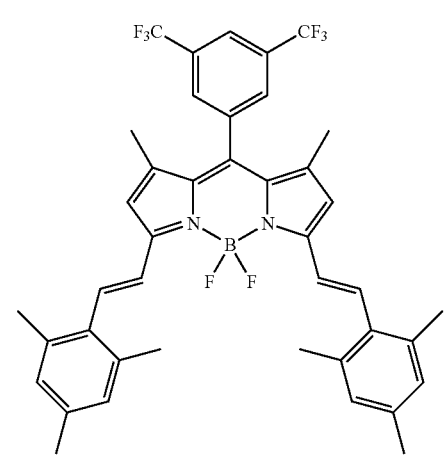
F-21
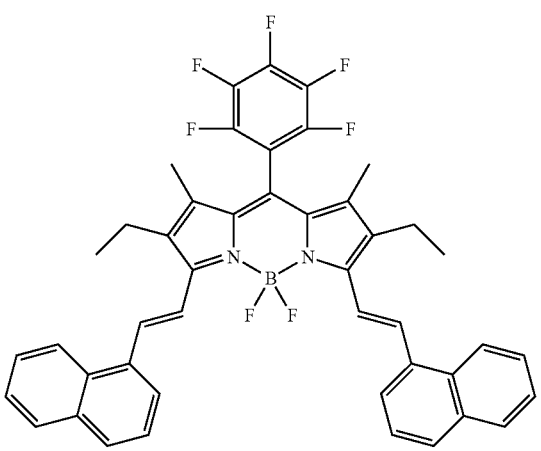
-continued
F-22
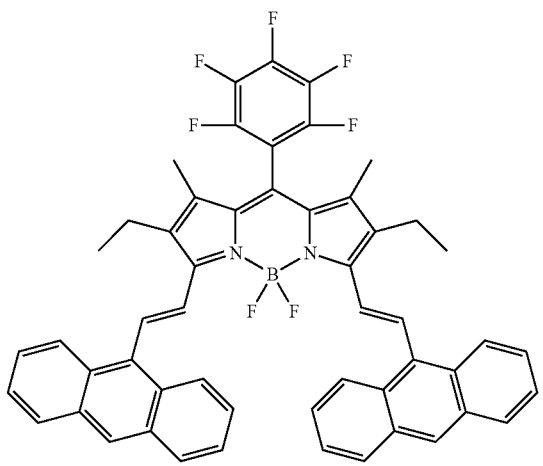
F-23
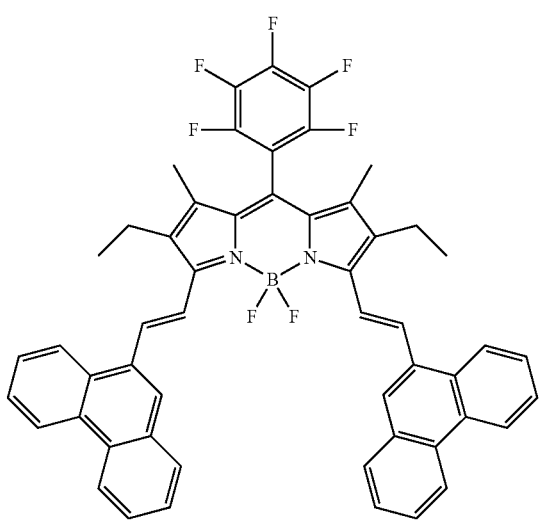
F-24
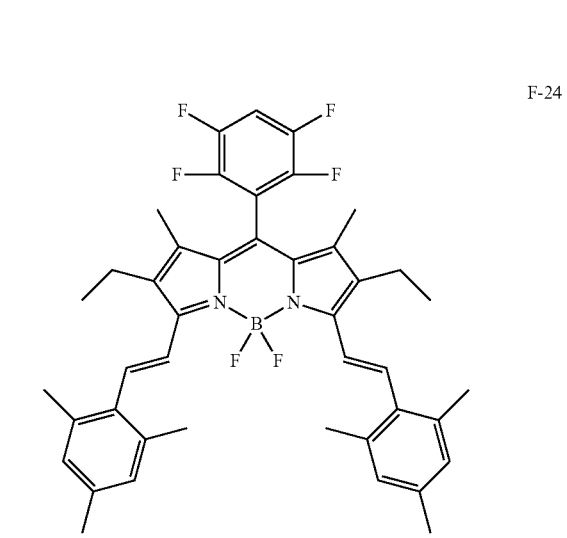

F-25
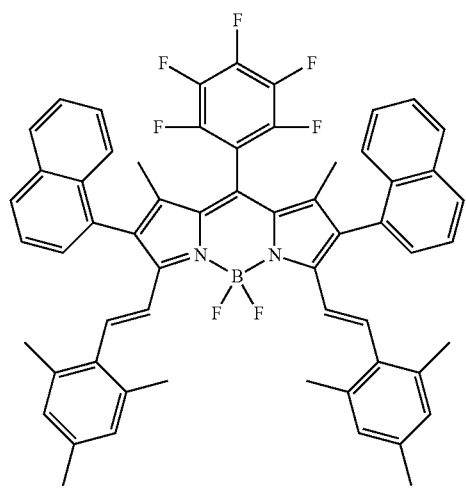
F-26
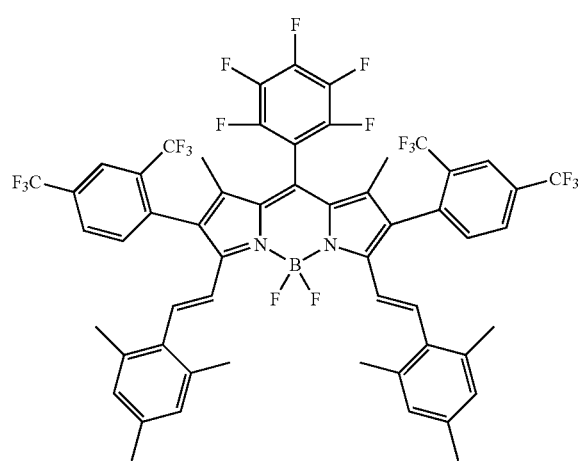
F-27
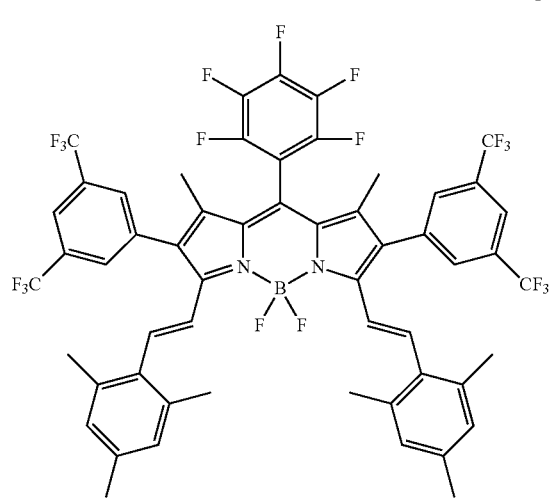
F-28
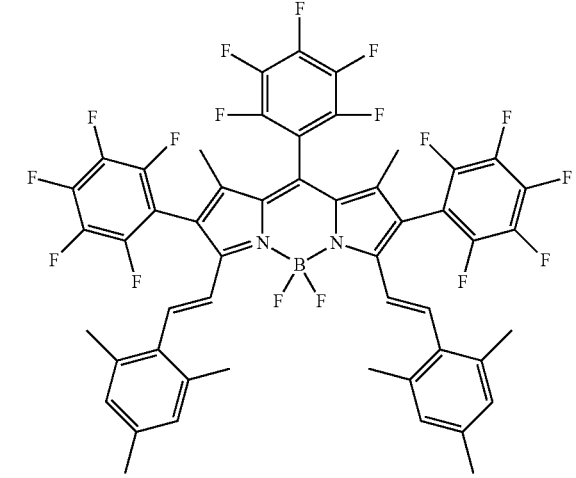
F-29
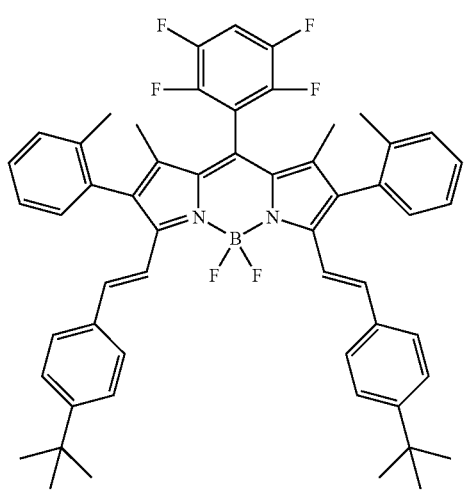
F-30
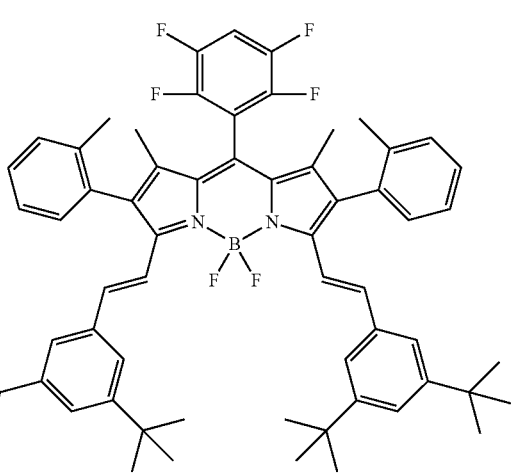

-continued
F-31
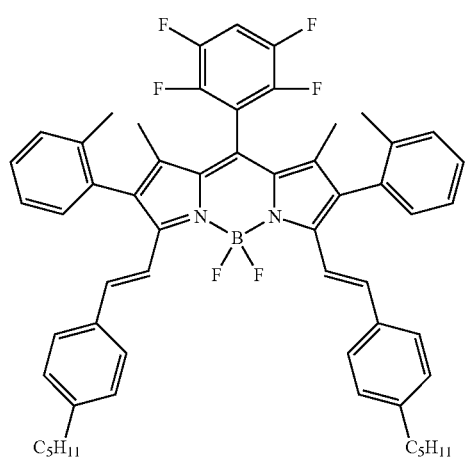
F-32
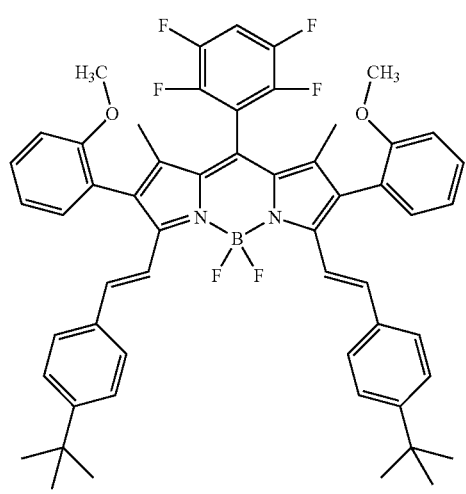
F-33
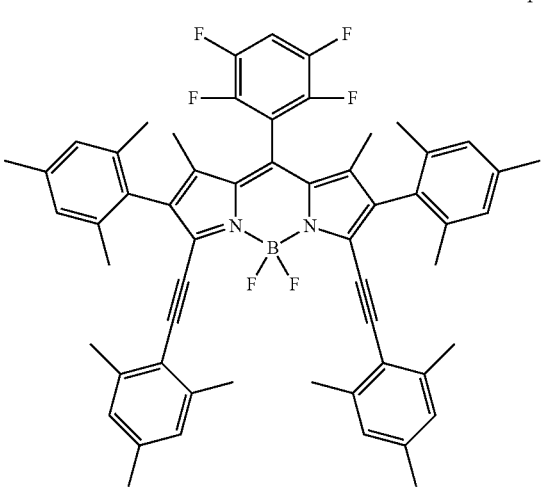
F-34
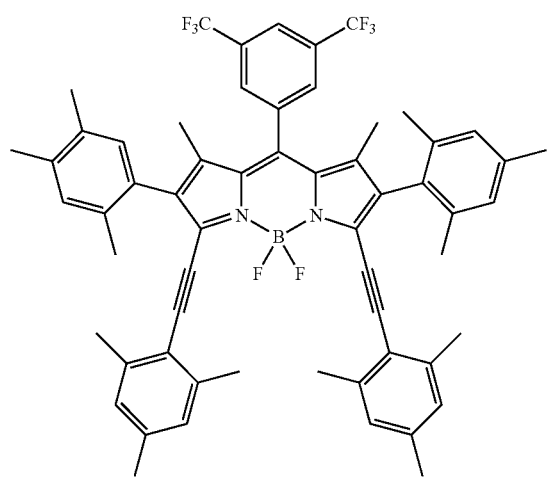
F-35
F-36
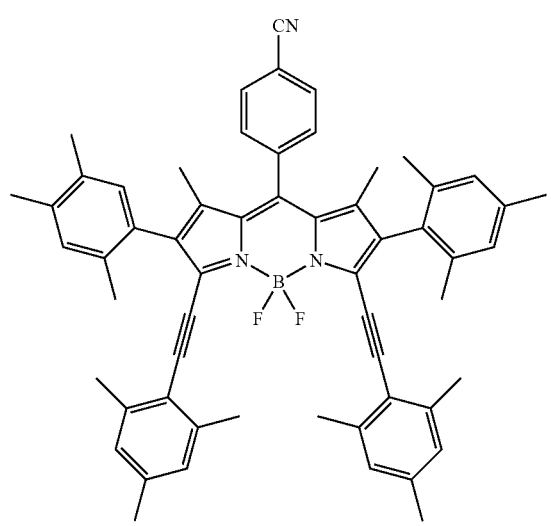

-continued
F-37
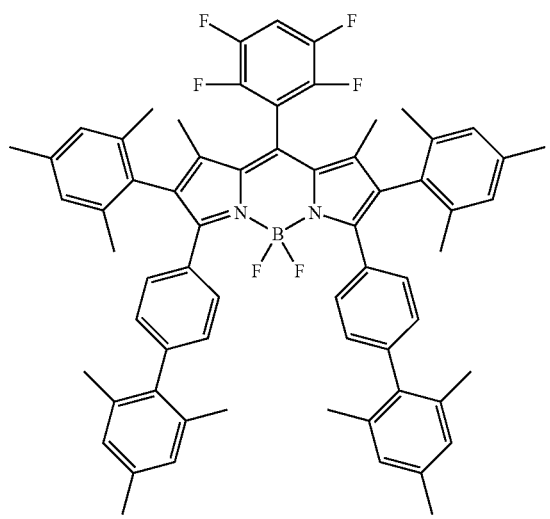
F-38
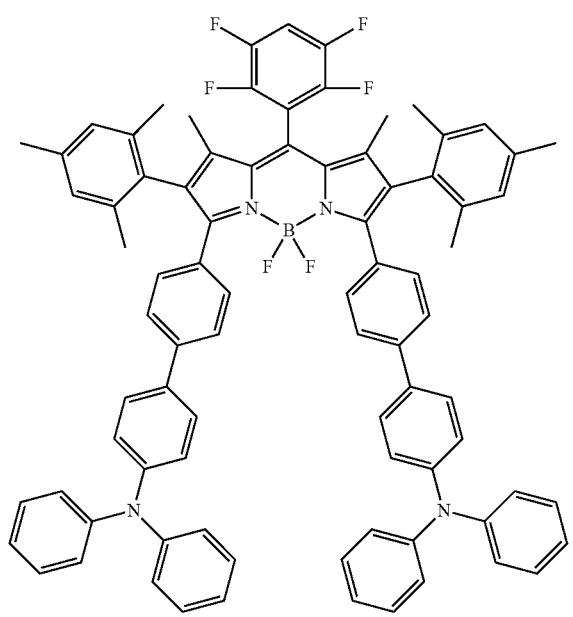
F-39
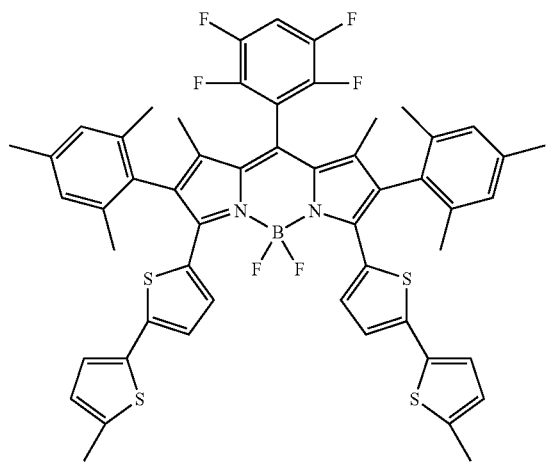
-continued
F-40
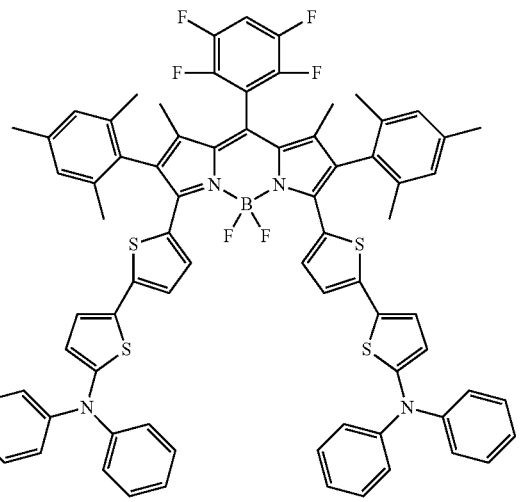
F-41
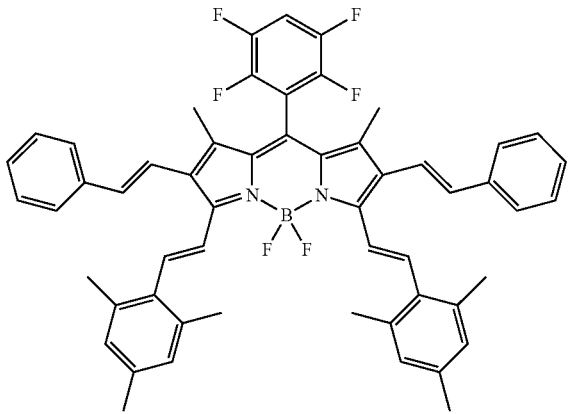
F-42
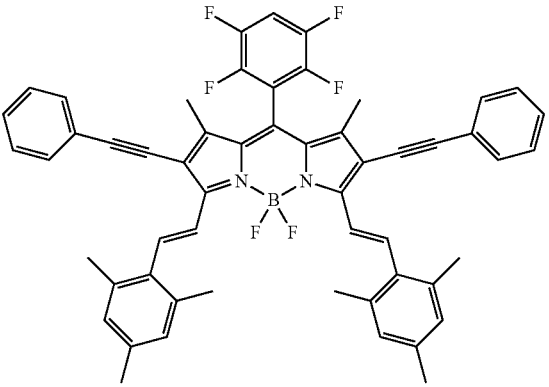

F-43
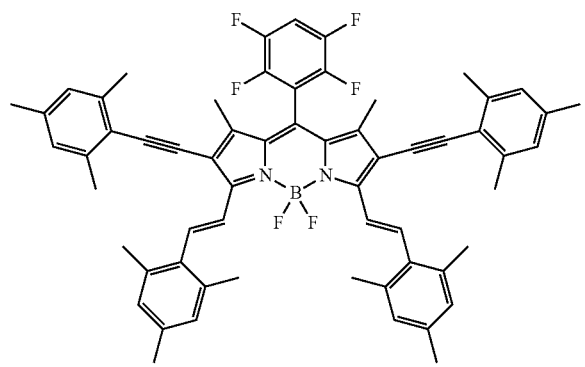
F-44
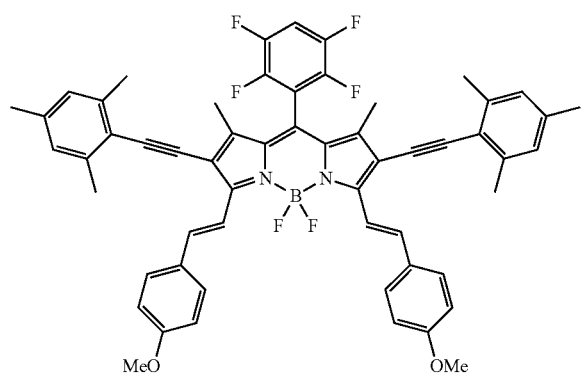
F-45
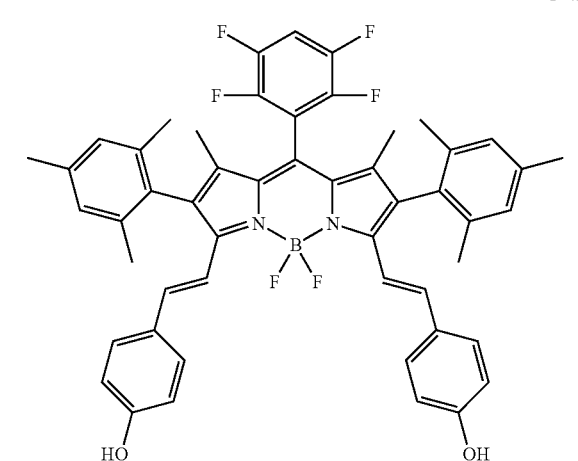
F-46
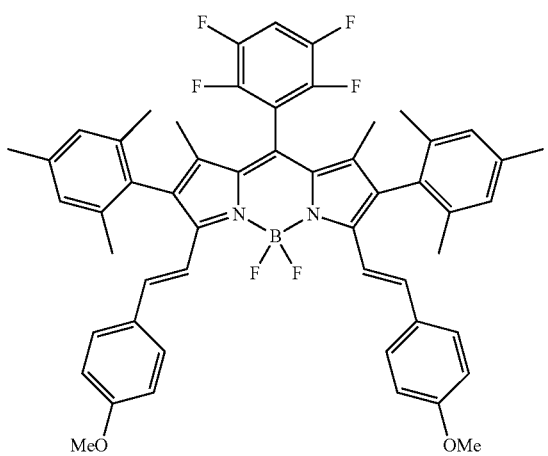
F-47
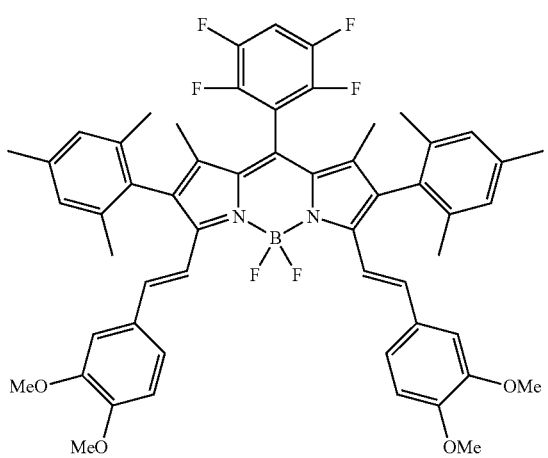
F-48
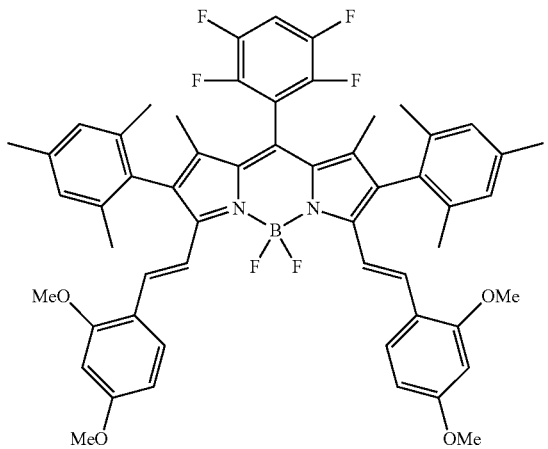

-continued
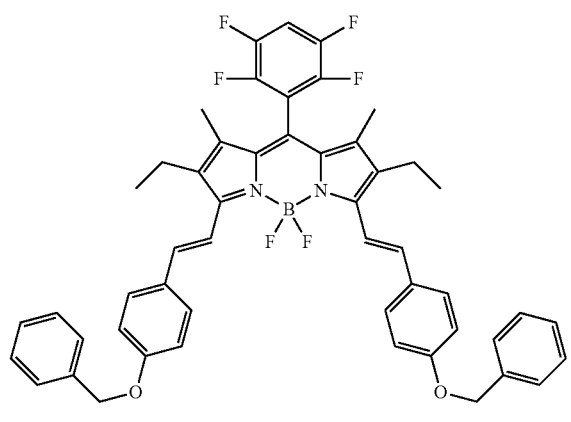
F-49
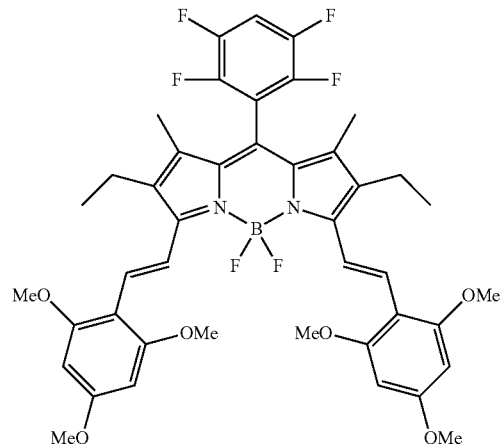
F-52
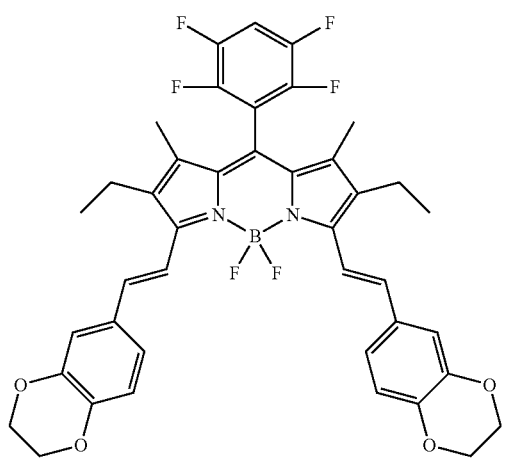
F-50
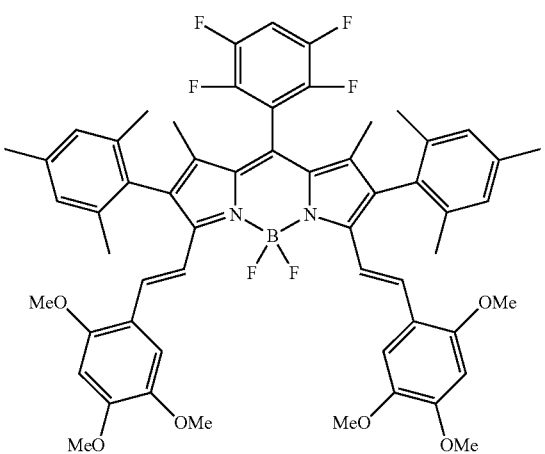
F-53
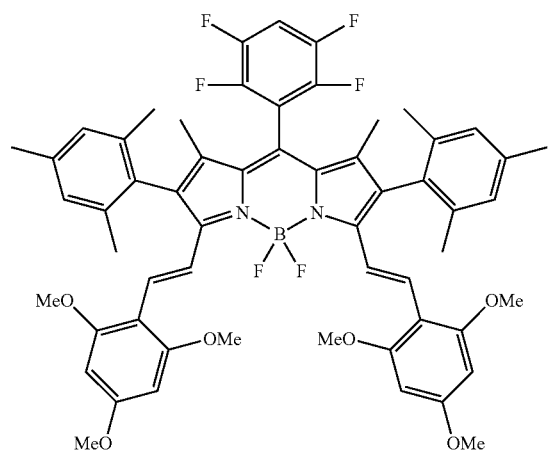
F-51
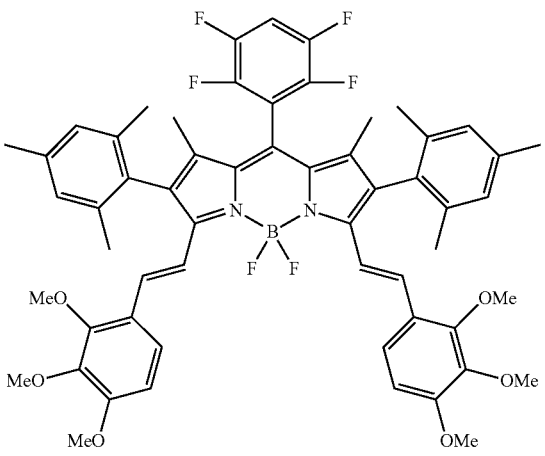
F-54

-continued
F-55
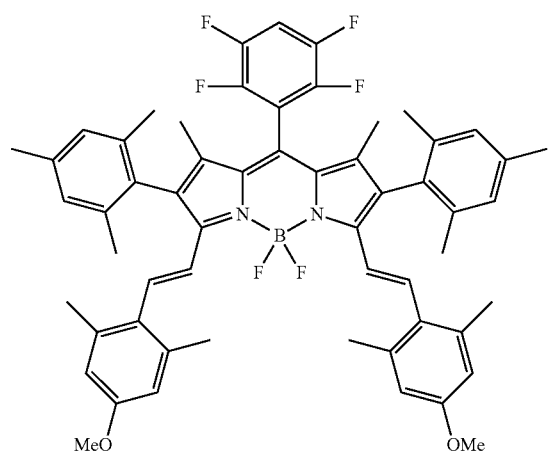
F-58
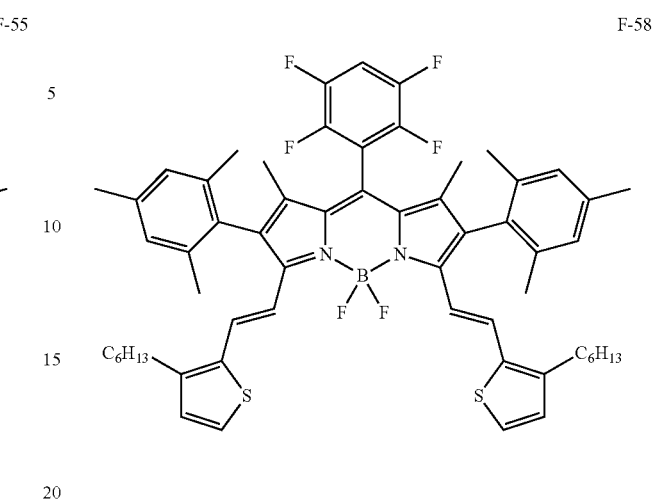
F-56
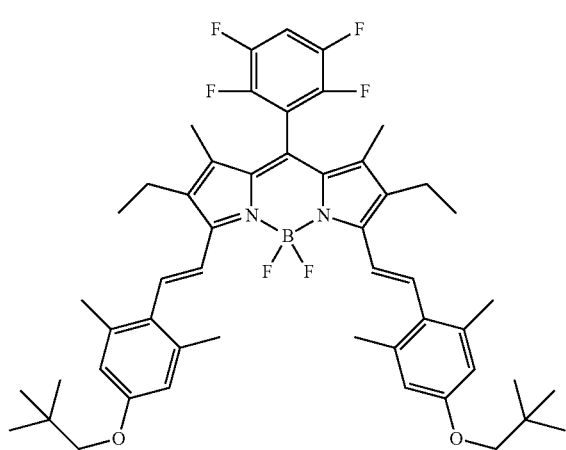
F-59
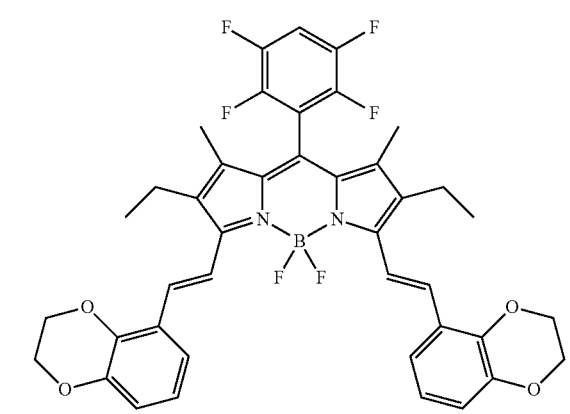
F-57
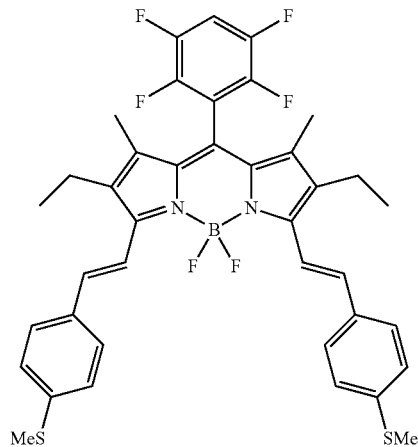
F-60
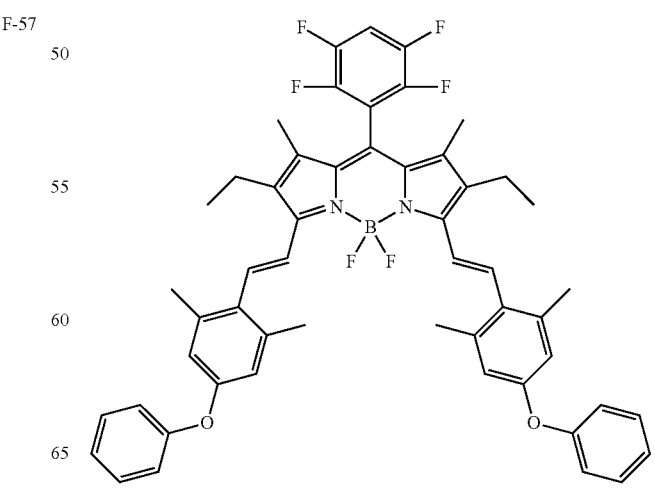

-continued
F-61
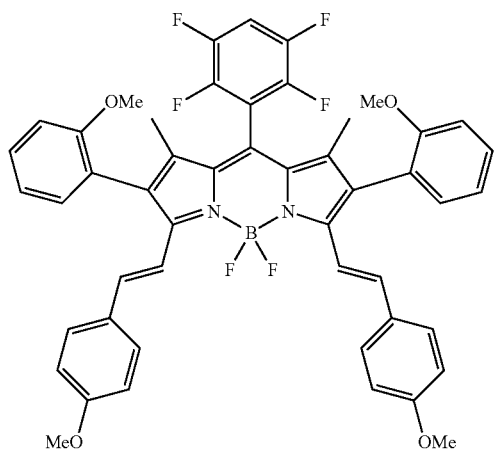
F-62
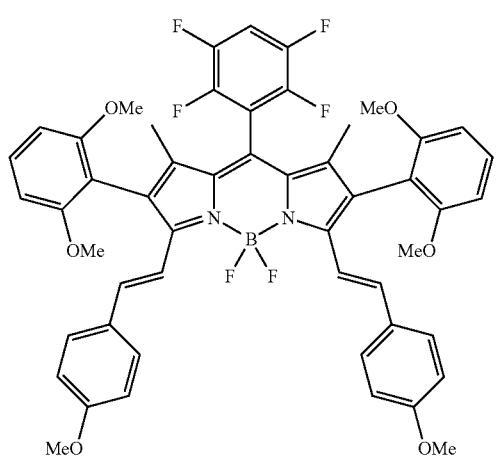
F-63
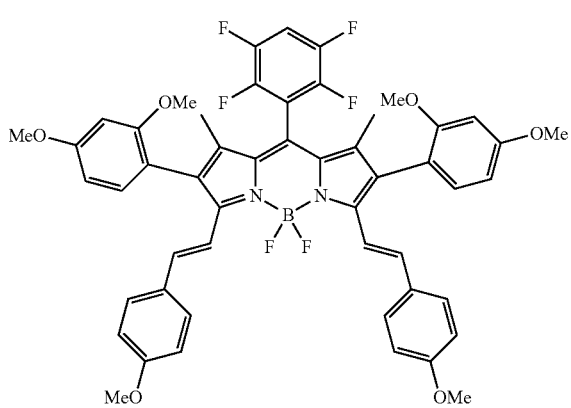
-continued
F-64
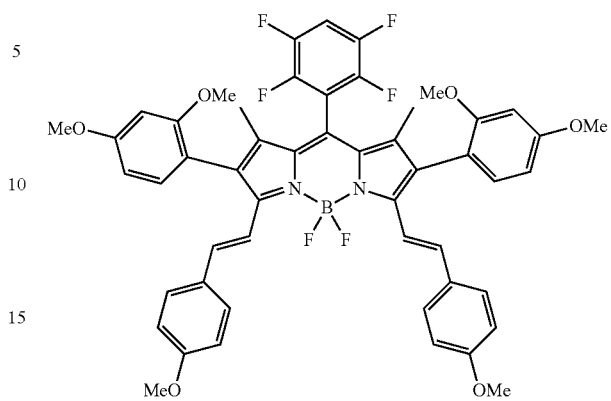
F-65
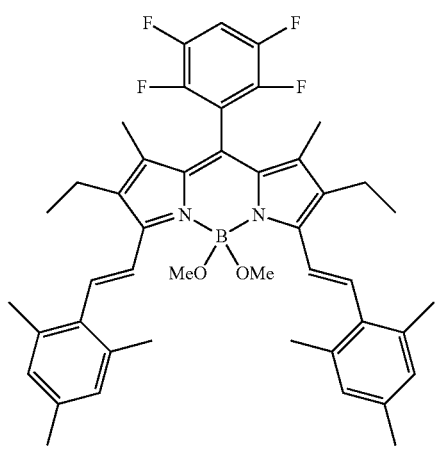
F-66
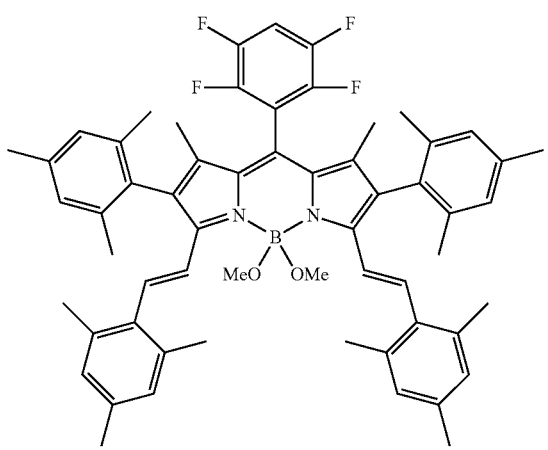

-continued
F-67
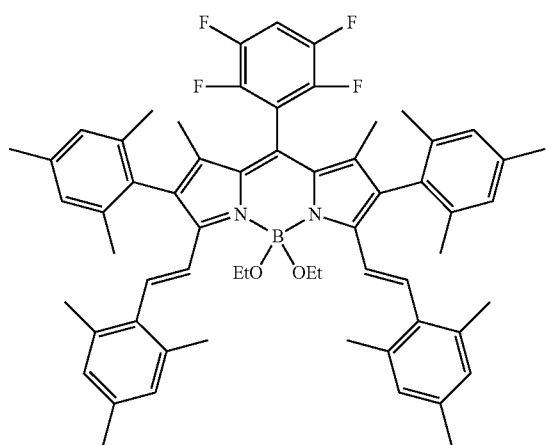
F-68
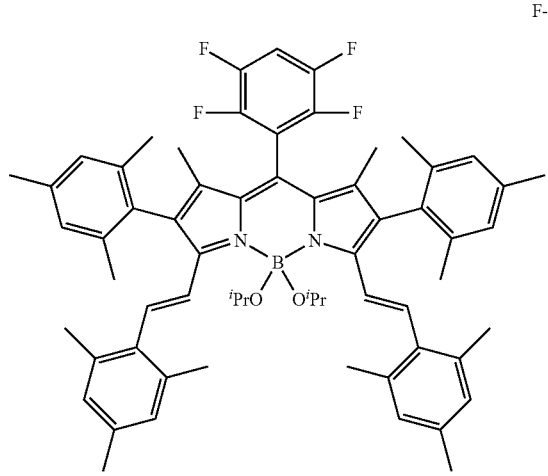
F-69
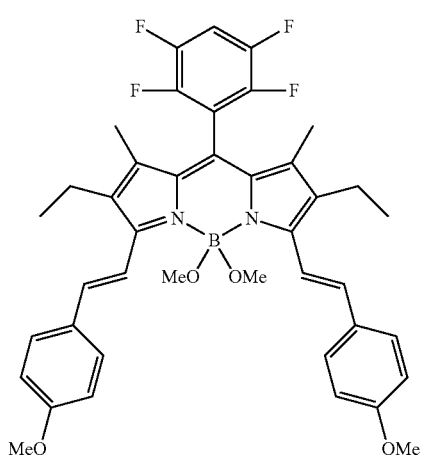
-continued
F-70
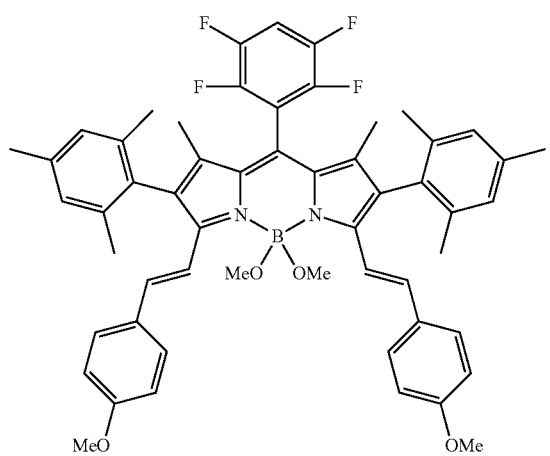
F-71
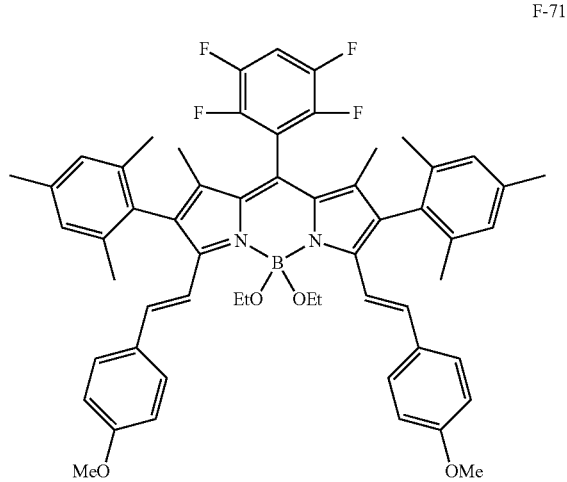
F-72
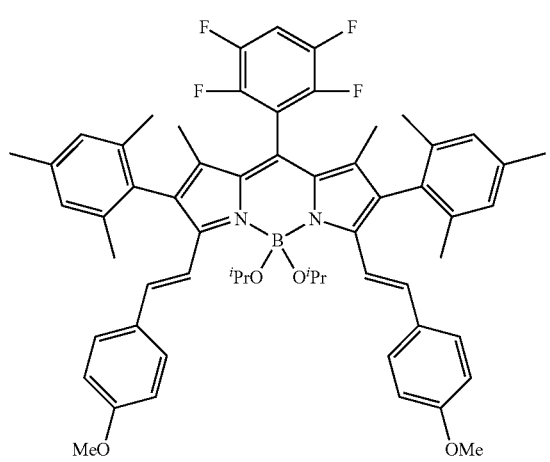

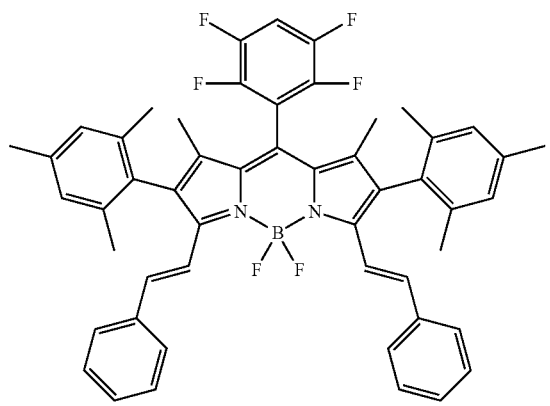
F-73
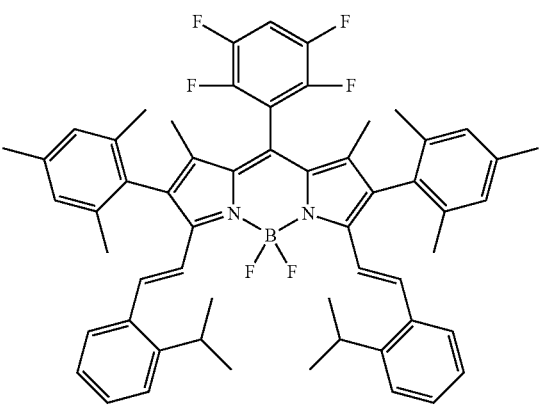
F-73
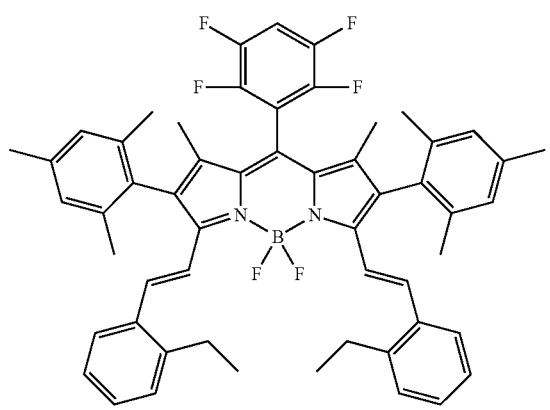
F-73
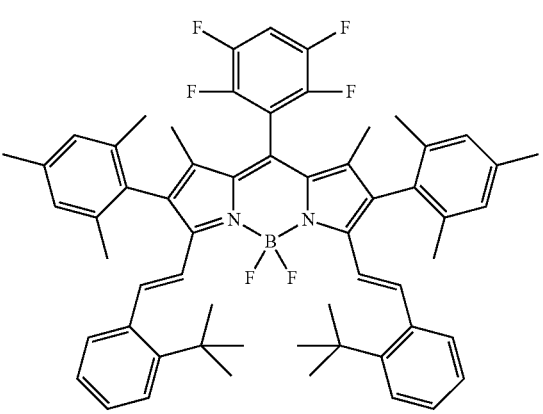
F-74
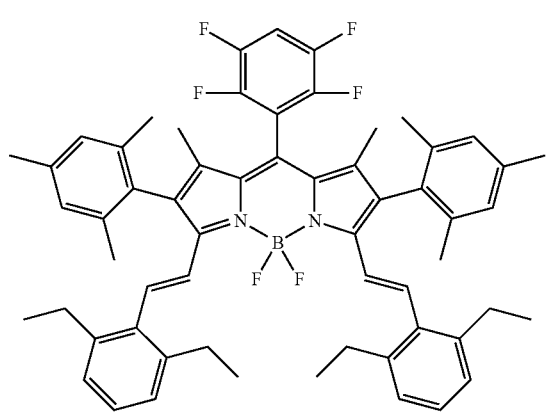
F-73
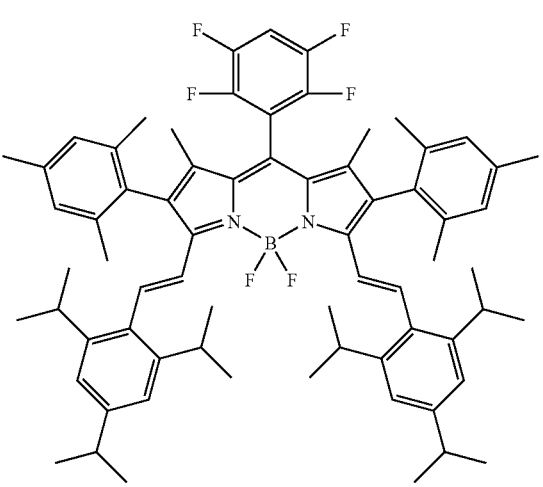
F-75

F-76
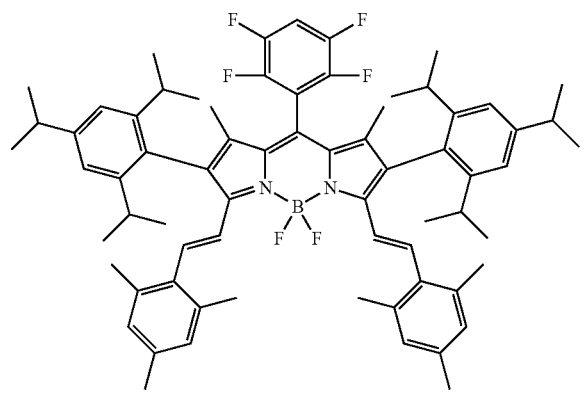
F-77
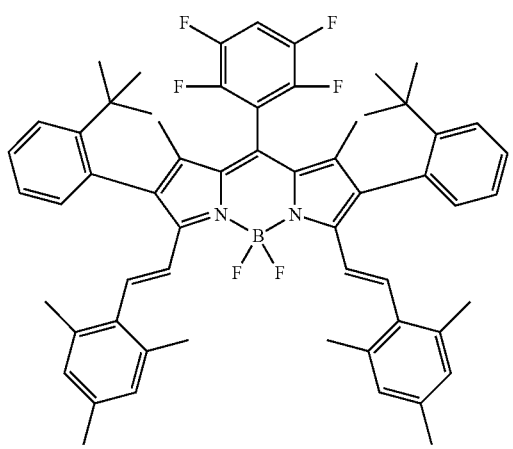
F-78
F-79
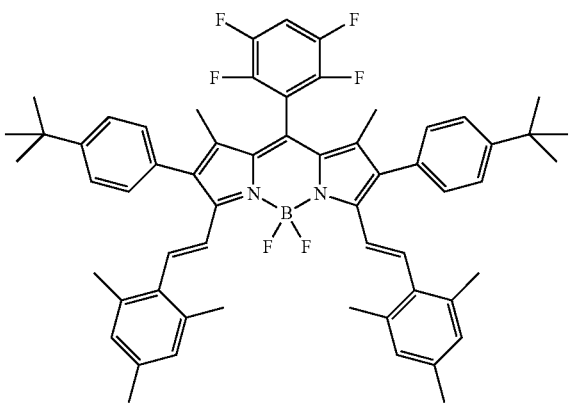
F-80
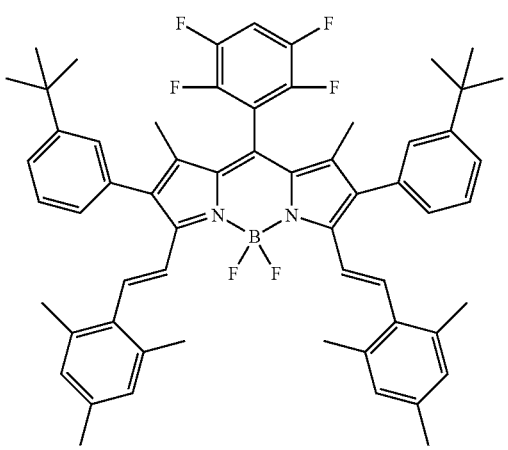
F-81
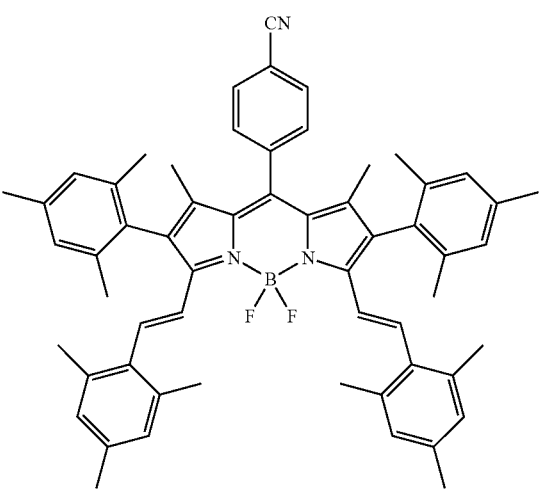

F-82
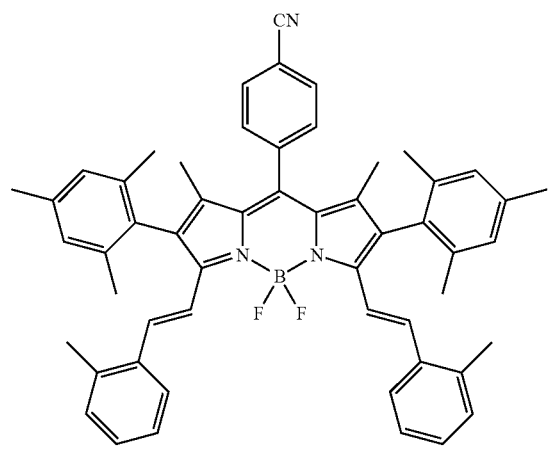
F-85
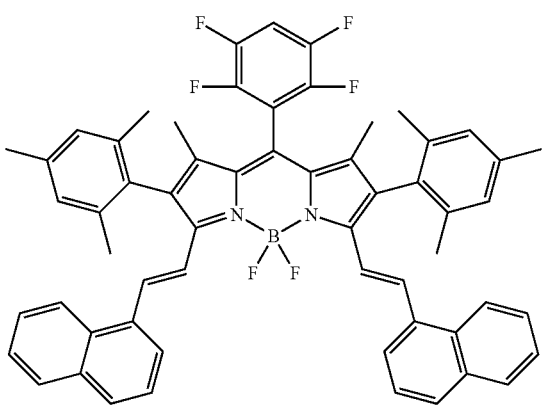
F-83
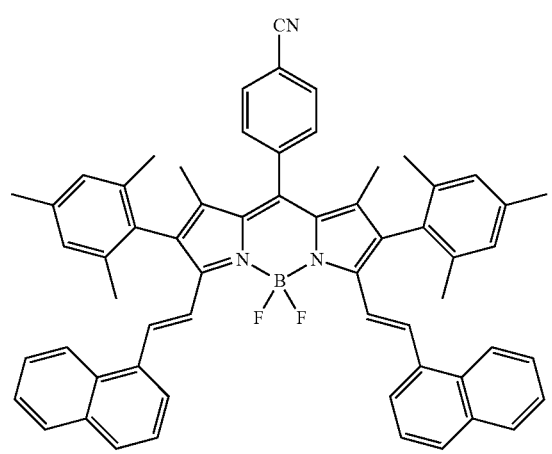
F-86
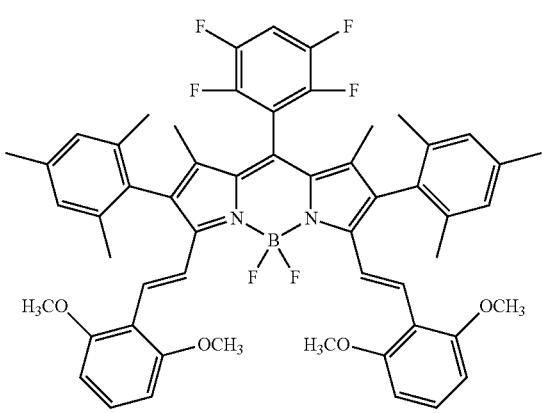
F-84
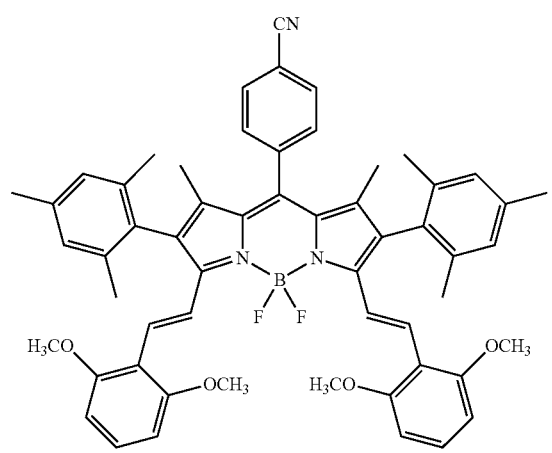
F-87
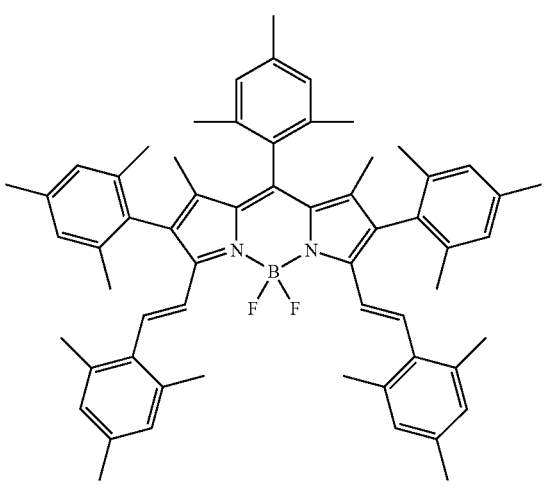

F-88

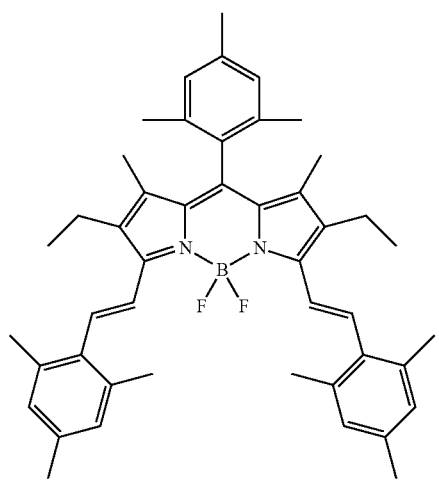

F-91

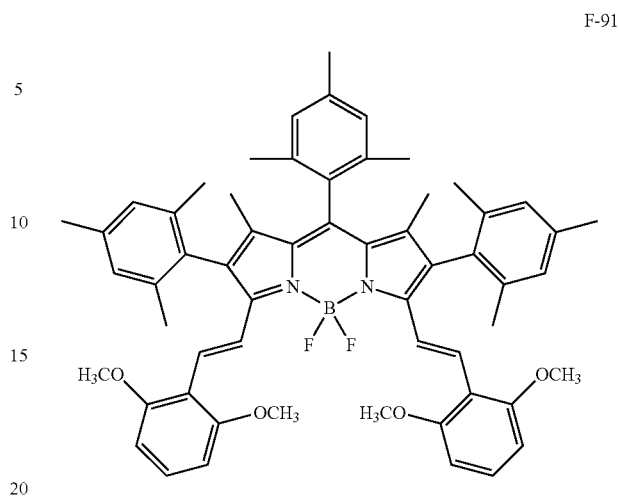

F-89

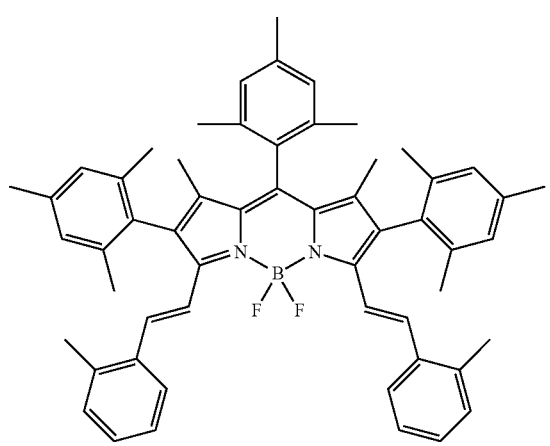

F-92

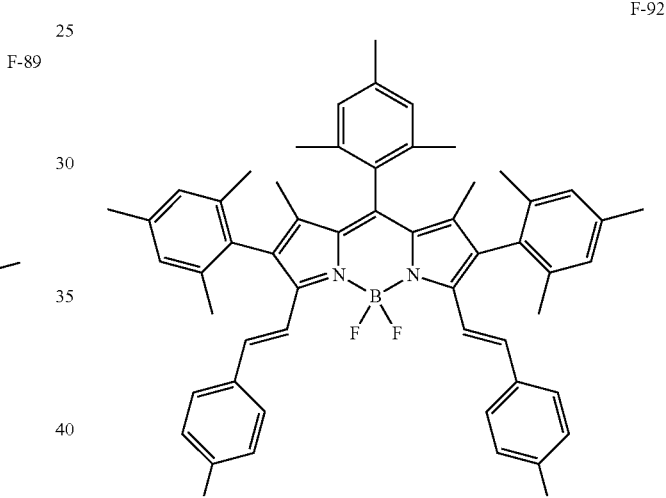

F-90

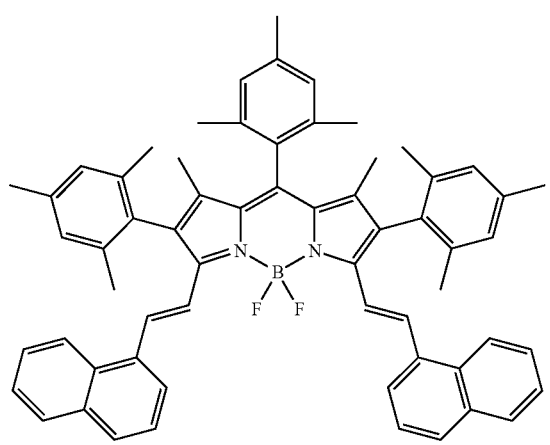

A labeled particle may be a labeled particle containing at least one kind of energy donor compound, at least one kind of energy acceptor compound, and a particle, and in such a case, at least one kind of the energy donor compound or the energy acceptor compound may be the compound represented by Formula (1).

In another example of the present invention, a luminescent labeled particle contains the compound represented by Formula (1) as one of an energy donor compound or an energy acceptor compound, and a compound represented by Formula (10) as the other of an energy donor compound or an energy acceptor compound. That is, the luminescent labeled particle may be a luminescent labeled particle containing the compound represented by Formula (1) as the energy donor compound and the compound represented by Formula (10) as the energy acceptor compound, or may be a luminescent labeled particle containing the compound represented by Formula (1) as the energy acceptor compound and the compound represented by Formula (10) as the energy donor compound.

<Compound Represented by Formula (10)>

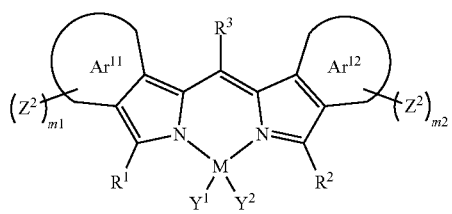

(10)

In Formula (10), m1 and m2 each independently represent an integer of 0 to 4, and any one of m1 or m2 is at least one. M represents a metalloid atom or a metal atom. $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, each of which may have a substituent. $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $Y^1$ and $Y^2$ may be linked to each other to form a ring. $Ar^{11}$ and $Ar^{12}$ each independently represent an aromatic ring which may have a substituent. $Z^1$ and $Z^2$ each independently represent an aryl group, a heterocyclic group, or an amino group, each of which may have a substituent. In the case where m1 is two or more, a plurality of $Z^1$'s may be the same group or different groups, and in the case where m2 is two or more, a plurality of $Z^2$'s may be the same group or different groups.

In Formula (10), m1 and m2 each independently represent an integer of 0 to 4, and preferably both m1 and m2 are one or more. m1 and m2 may be the same integer or different integers, and are preferably the same integer. Preferably, m1 and m2 are each independently one or two, more preferably, both m1 and m2 are one or two, and particularly preferably both m1 and m2 are one.

In Formula (10), M represents a metalloid atom or a metal atom, preferably a metalloid atom, and particularly preferably a boron atom.

In Formula (10), $R^1$, $R^2$, and $R^3$ each independently represent a hydrogen atom, an alkyl group, an aryl group, a heterocyclic group, an ethenyl group, an ethynyl group, an acyl group, an alkoxy group, an aryloxy group, an alkylthio group, or an arylthio group, each of which may have a substituent.

Preferably, $R^1$ and $R^2$ each independently represent an aryl group or a heterocyclic group, each of which may have a substituent.

$R^1$ and $R^2$ may be the same as or different from each other, and are preferably the same as each other.

$R^1$ and $R^2$ are not linked to each other to form a ring.

Preferably, $R^3$ represents a hydrogen atom, an alkyl group, an aryl group, or a heterocyclic group, each of which may have a substituent. More preferably, $R^3$ is a hydrogen atom.

In Formula (10), $Y^1$ and $Y^2$ each independently represent a halogen atom, an alkyl group, an aryl group, a heterocyclic group, a hydroxy group, an alkoxy group, an aryloxy group, an alkylthio group, an arylthio group, an ethenyl group, or an ethynyl group, each of which may have a substituent, and $Y^1$ and $Y^2$ may be linked to each other to form a ring.

Preferably, $Y^1$ and $Y^2$ each independently represent a halogen atom, an alkyl group, an aryl group, a hydroxy group, an alkoxy group, or an aryloxy group, each of which may have a substituent, and $Y^1$ and $Y^2$ may be linked to each other to form a ring.

More preferably, $Y^1$ and $Y^2$ are each independently halogen atoms.

Still more preferably, $Y^1$ and $Y^2$ are fluorine atoms.

$Y^1$ and $Y^2$ may be the same as or different from each other, and are preferably the same as each other.

In Formula (10), $Ar^1$ and $Ar^2$ each independently represent an aromatic ring which may have a substituent.

Preferably, $Ar^1$ and $Ar^2$ each represent a benzene ring.

In Formula (10), $Z^1$ to $Z^2$ each independently represent a halogen atom, an alkyl group, an aryl group, a heterocyclic group, an ethenyl group, an ethynyl group, an acyl group, an alkoxy group, an aryloxy group, an alkylthio group, an arylthio group, or an amino group, each of which may have a substituent. In the case where m1 is two or more, a plurality of $Z^1$'s may be the same group or different groups, and in the case where m2 is two or more, a plurality of $Z^2$'s may be the same group or different groups.

Preferably, $Z^1$ and $Z^2$ each independently represent an aryl group which may have a substituent.

More preferably, $Z^1$ and $Z^2$ each independently represent a phenyl group, a naphthyl group, or an anthryl group, each of which may have a substituent.

Preferably, in the case where m1 is two or more, a plurality of $Z^1$'s are the same group.

Preferably, in the case where m2 is two or more, a plurality of $Z^2$'s are the same group.

It is preferred that the compound represented by Formula (2) does not have acidic groups, such as a carboxylic acid group, a phosphoric acid group, and a sulfonic acid group, in a molecule.

<As to Compound Represented by Formula (10A)>

A preferred example of the compound represented by Formula (10) is a compound represented by Formula (10A).

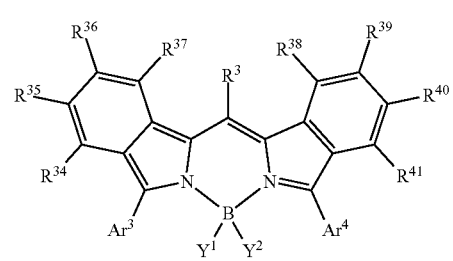

(10A)

In Formula (10A), $Y^1$ to $Y^2$ each independently represent a halogen atom, an alkyl group, an aryl group, a heterocyclic group, a hydroxy group, an alkoxy group, an aryloxy group, an alkylthio group, or an arylthio group, an ethenyl group, or an ethynyl group, each of which may have a substituent. Examples of the substituent include the substituents described in Substituent group A.

Preferably, $Y^1$ and $Y^2$ each independently represent halogen atoms.

Particularly preferably, $Y^1$ and $Y^2$ are fluorine atoms.

In Formula (10A), $R^3$ represents a hydrogen atom, an alkyl group, an aryl group, a heterocyclic group, an ethenyl group, an ethynyl group, or an acyl group, each of which may have a substituent.

Preferably, $R^3$ represents a hydrogen atom, an alkyl group, an aryl group, or a heterocyclic group, each of which may have a substituent.

More preferably, R³ is a hydrogen atom.

In Formula (10A), Ar³ and Ar⁴ each independently represent an aryl group or a heterocyclic group, each of which may have a substituent. Examples of the substituent include the substituents described in Substituent group A.

In Formula (10A), $R^{34}$ to $R^{41}$ each independently represent a hydrogen atom, a halogen atom, an alkyl group, an aryl group, a heterocyclic group, an ethenyl group, an ethynyl group, an acyl group, an alkoxy group, an aryloxy group, an alkylthio group, an arylthio group, or an amino group, each of which may have a substituent. Examples of the substituent include the substituents described in Substituent group A.

In Formula (10A), at least one of $R^{34}$, ..., or $R^{41}$ is preferably an aryl group which may have a substituent.

More preferably, at least one of $R^{34}$, ..., or $R^{37}$ is an aryl group which may have a substituent, and at least one of $R^{38}$, ..., or $R^{41}$ is an aryl group which may have a substituent.

More preferably, at least one of $R^{34}$, ..., or $R^{41}$ is a group represented by Formula (11). Still more preferably, at least one of $R^{34}$, ..., or $R^{37}$ is a group represented by Formula (11), and at least one of $R^{38}$, ..., or $R^{41}$ is a group represented by Formula (11).

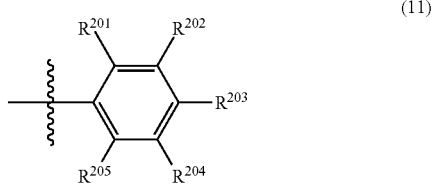

(11)

In Formula (11), $R^{201}$ to $R^{205}$ are each a hydrogen atom, a halogen atom, an alkyl group, an aryl group, a heterocyclic group, an ethenyl group, an ethynyl group, an acyl group, an alkoxy group, an aryloxy group, an alkylthio group, an arylthio group, or an amino group, and at least one of $R^{201}$, ..., or $R^{205}$, is an atom or group other than a hydrogen atom. $R^{201}$ and $R^{202}$ may be linked to each other to form a ring, $R^{202}$ and $R^{203}$ may be linked to each other to form a ring, $R^{203}$ and $R^{204}$ may be linked to each other to form a ring, and $R^{204}$ and $R^{205}$ may be linked to each other to form a ring.

According to another preferred aspect, at least one of $R^{34}$, ..., or $R^{41}$ is a group represented by Formula (12). More preferably, at least one of $R^{34}$, ..., or $R^{37}$ is a group represented by Formula (12), and at least one of $R^{38}$, ..., or $R^{41}$ is a group represented by Formula (12).

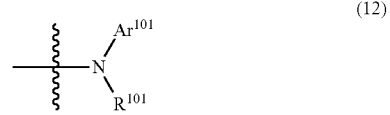

(12)

In Formula (12), $R^{101}$ represents a hydrogen atom, an alkyl group, an aryl group, a heterocyclic group, an ethenyl group, an ethynyl group, or an acyl group, each of which may have a substituent. Examples of the substituent include the substituents described in Substituent group A. $Ar^{101}$ represents an aryl group or a heterocyclic group, each of which may have a substituent. Examples of the substituent include the substituents described in Substituent group A. $Ar^{101}$ and $R^{101}$ may be linked to each other to form a ring.

It is preferred that the compound represented by Formula (10) does not have acidic groups, such as a carboxylic acid group, a phosphoric acid group, and a sulfonic acid group, in a molecule.

<Specific Examples of Compound Represented by Formula (10) or Formula (10A)>

Specific examples of the compound represented by Formula (10) or Formula (10A) are shown below. Me represents a methyl group, Bu represents an n-butyl group, and Ph represents a phenyl group.

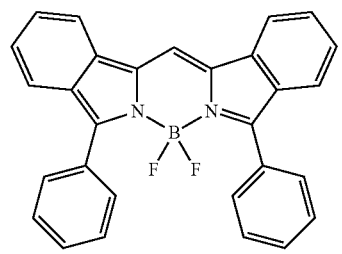

E-1

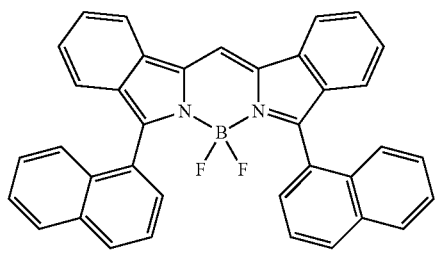

E-2

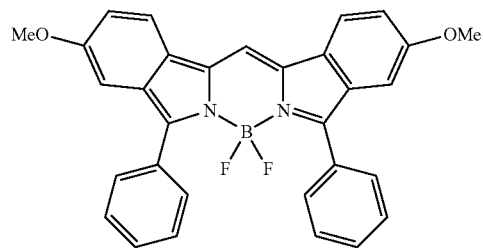

E-3

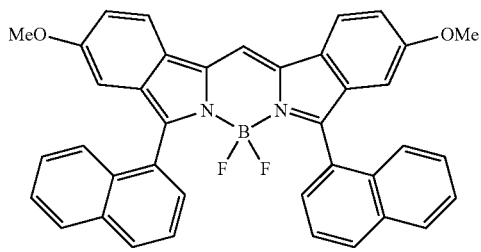

E-4

-continued
E-5 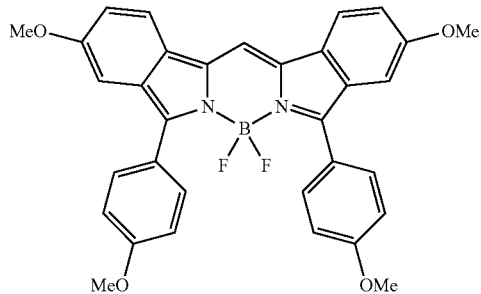
E-6 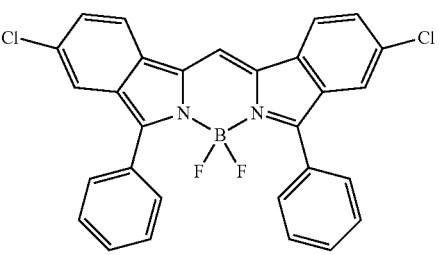
E-7 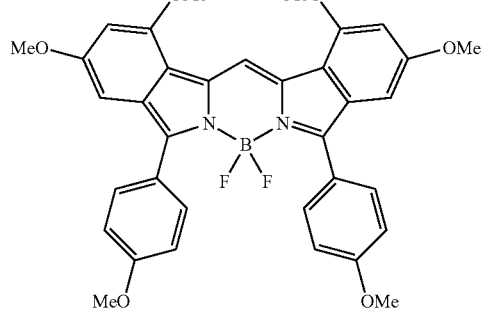
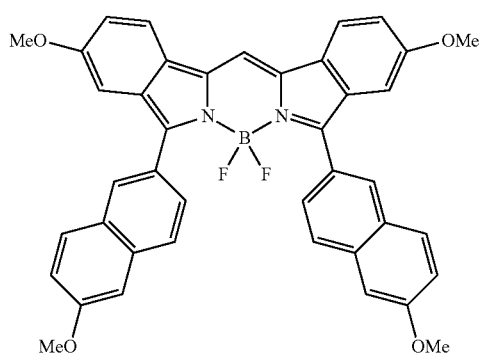
E-9
E-8 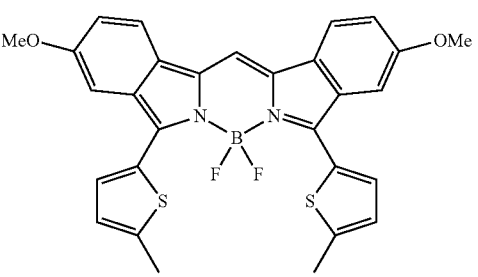
E-10
E-11 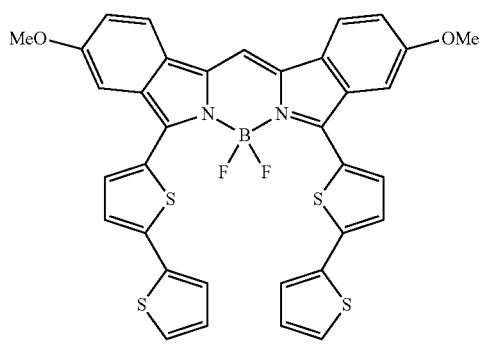
E-12 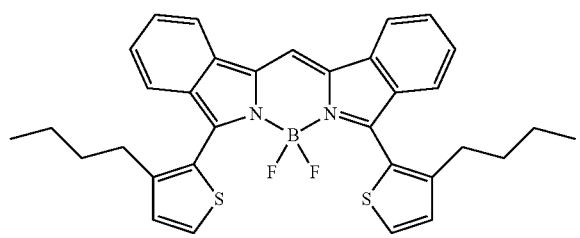
E-13 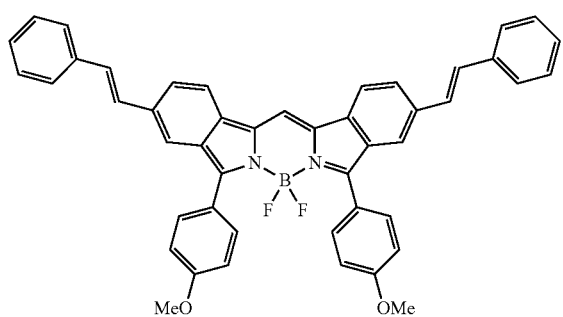
E-14 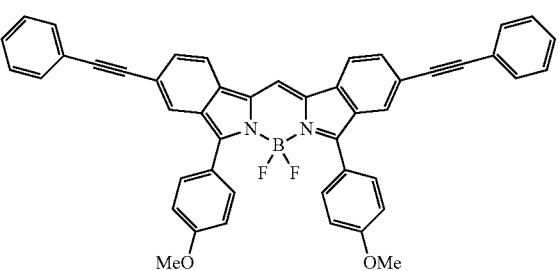

-continued
E-15
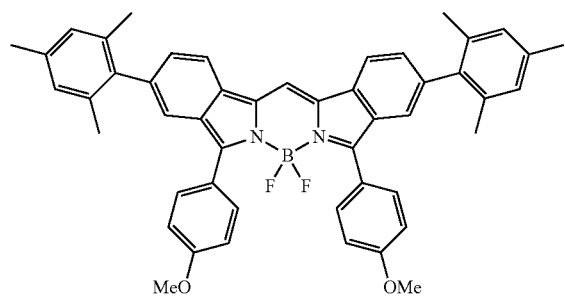
E-16
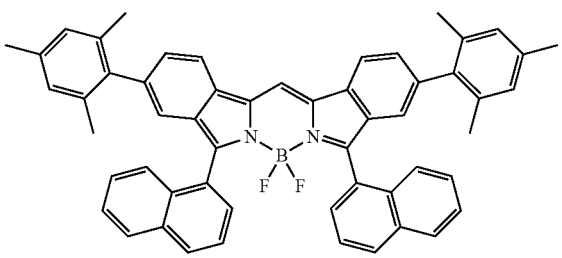
E-17
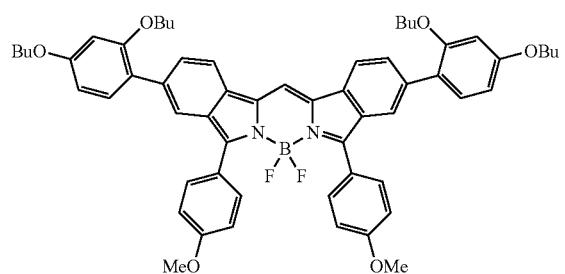
E-18
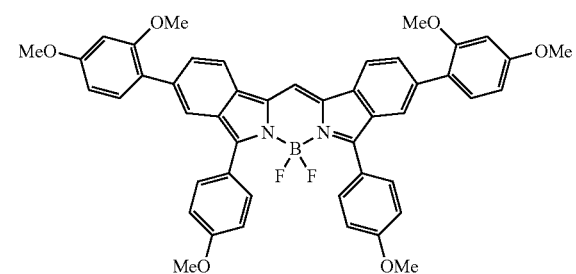
E-19
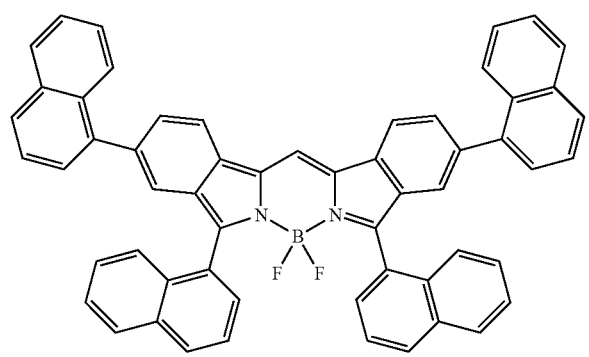
E-20
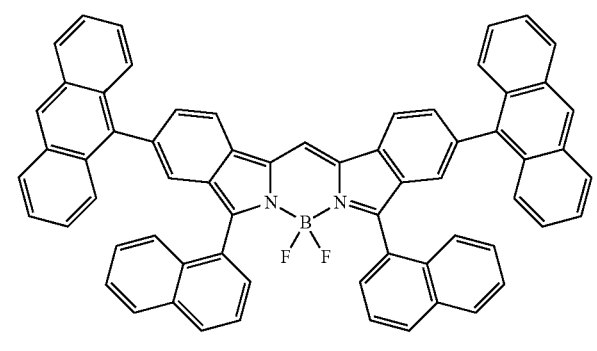
E-21
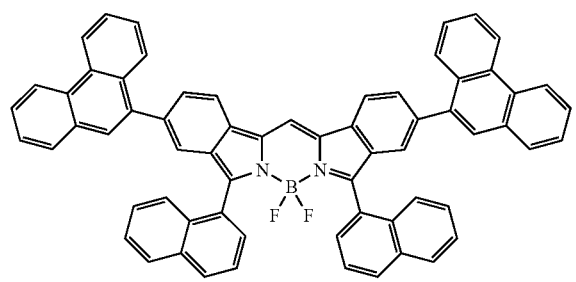
E-22
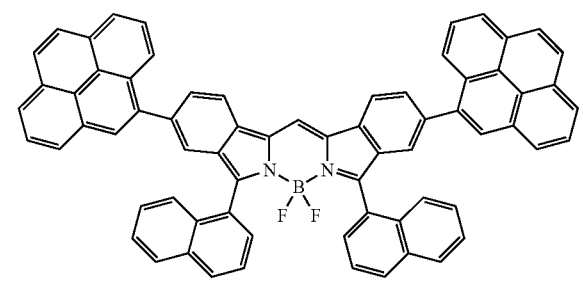

-continued
E-23
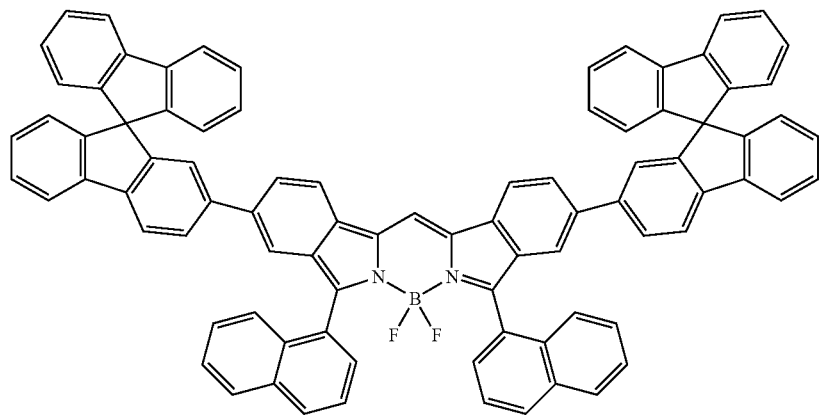
E-24
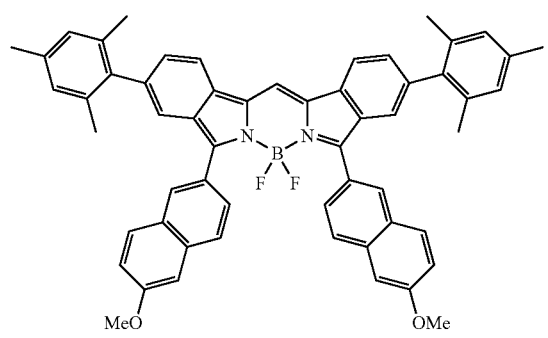
E-25
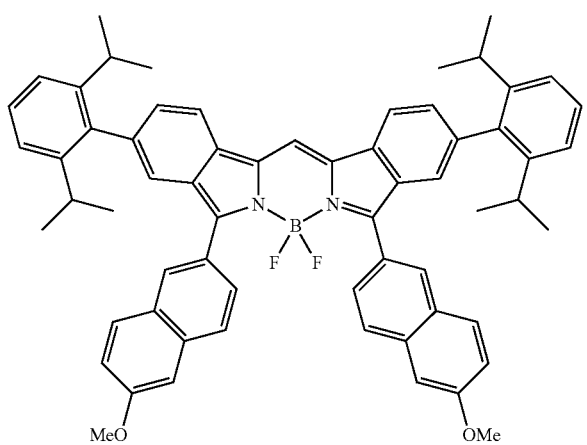
E-26
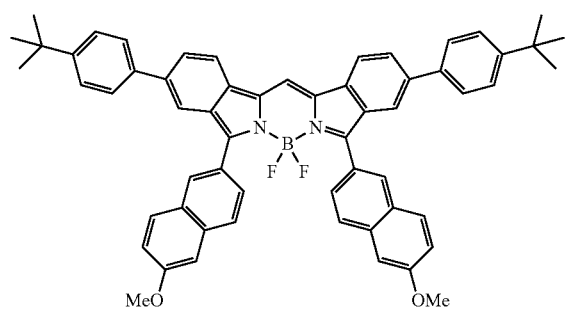
E-27
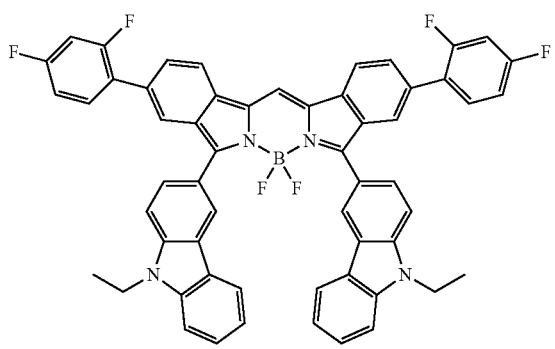
E-28
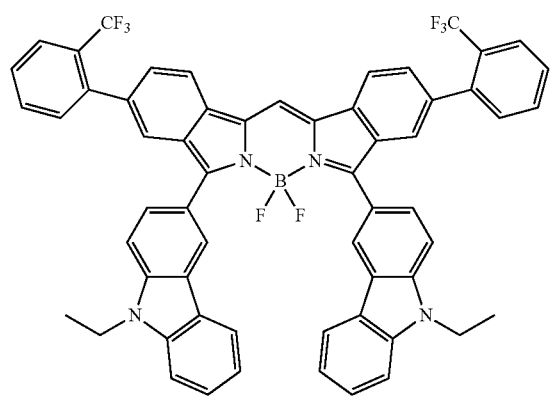
E-29
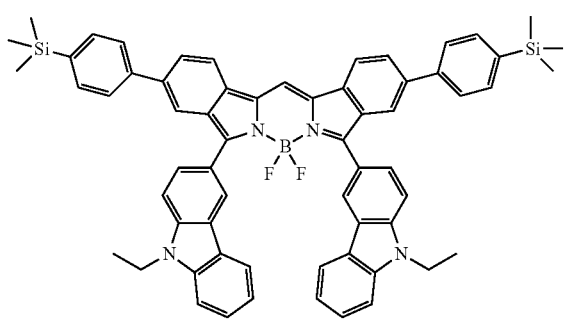

-continued
E-30
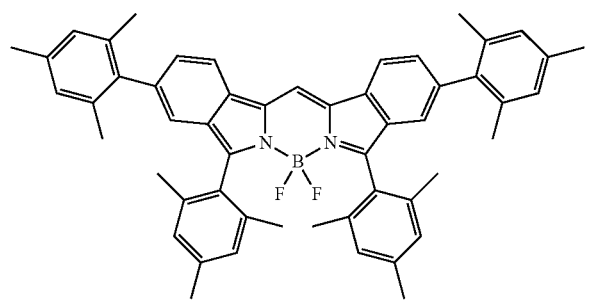
E-31
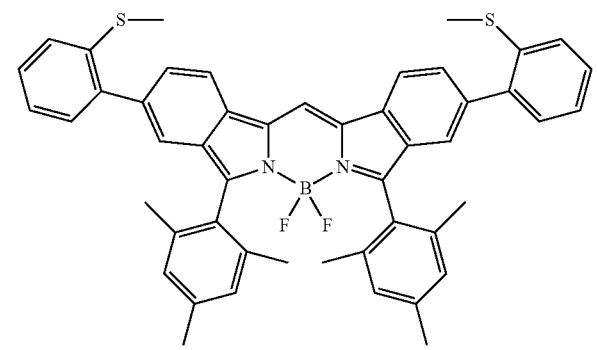
E-32
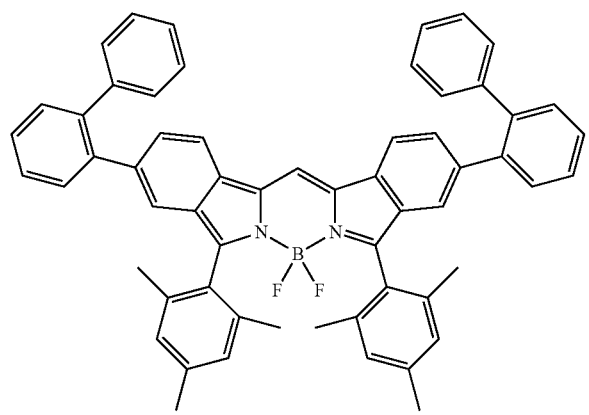
E-33
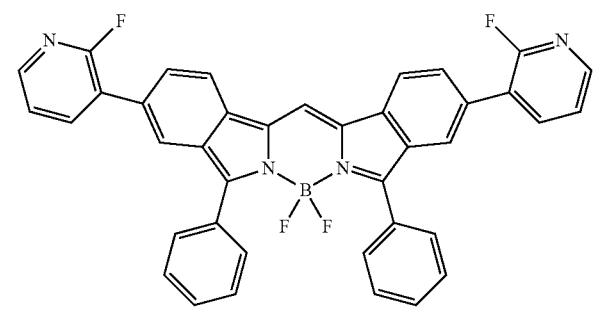
E-34
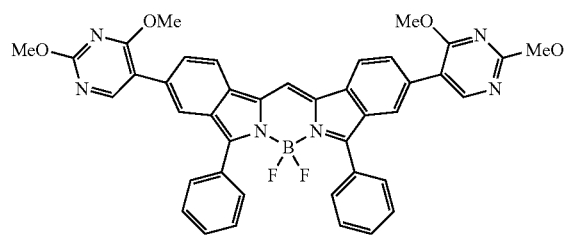
E-35
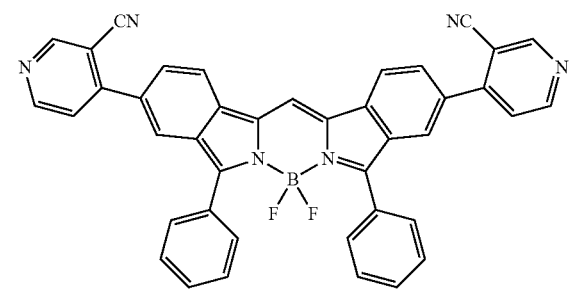
E-36
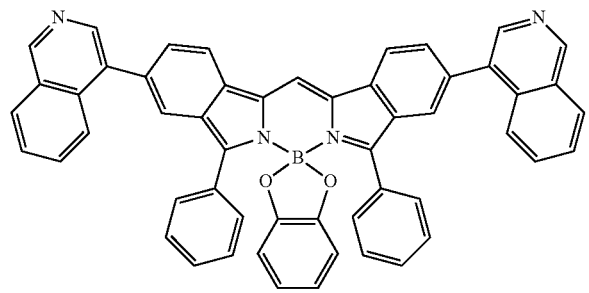
E-37
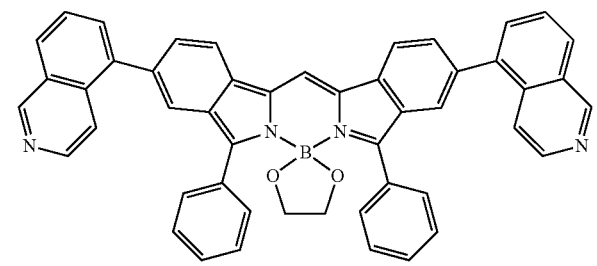

-continued
E-38
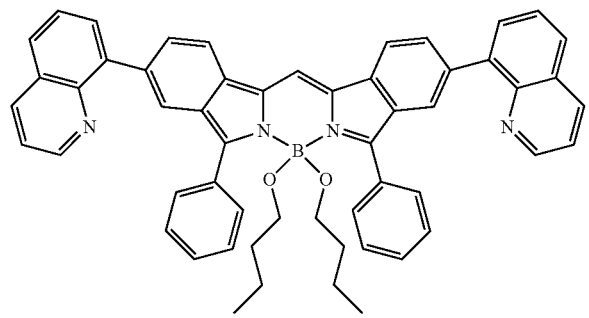
E-39
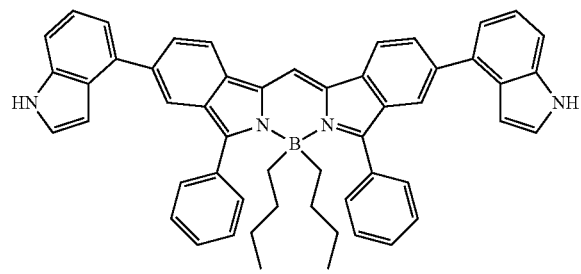
E-40
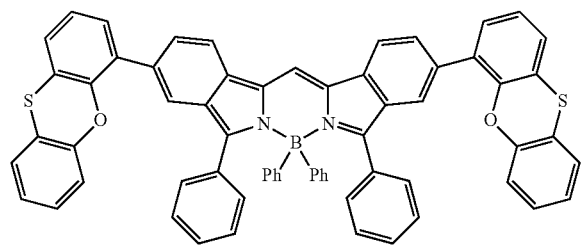
E-41
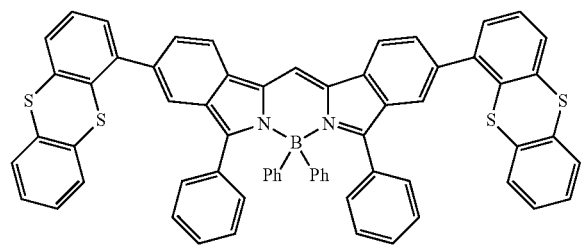
E-42
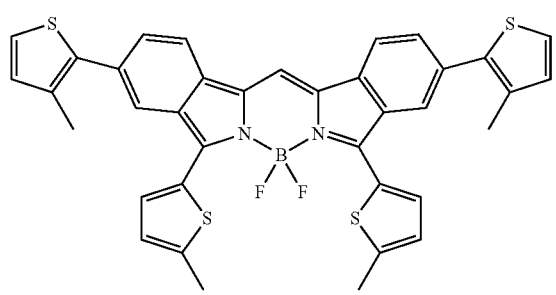
E-43
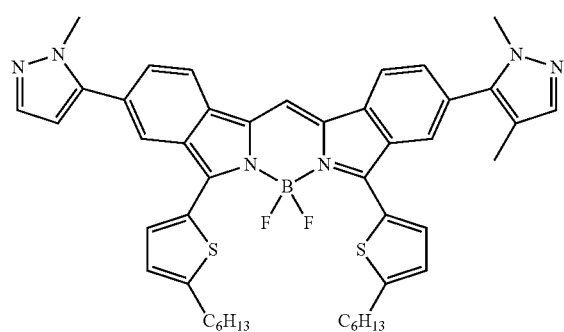
E-44
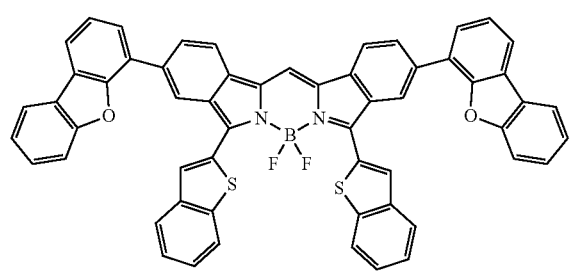
E-45
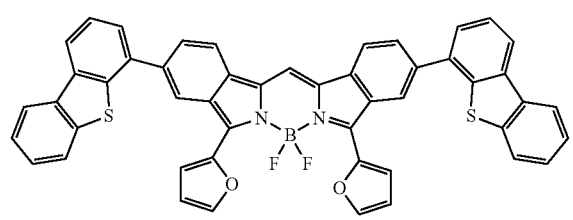
E-46
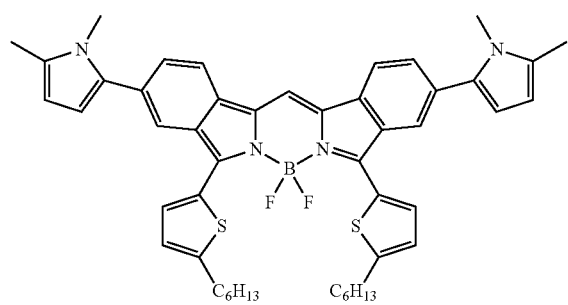
E-47
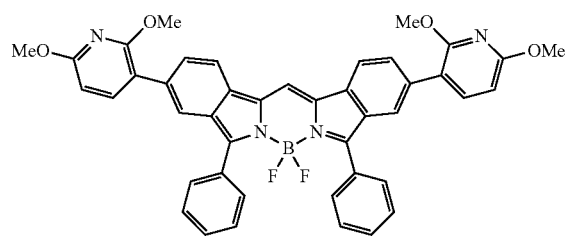

-continued
E-48
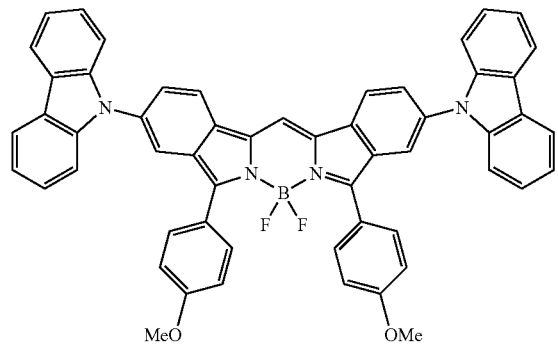
E-49
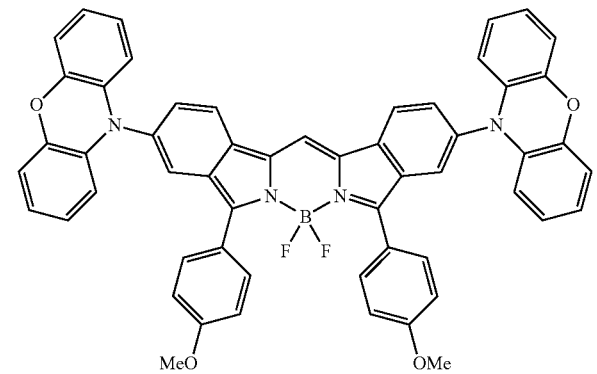
E-50
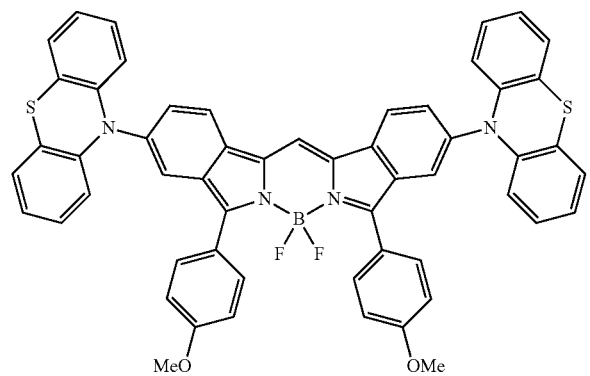
E-51
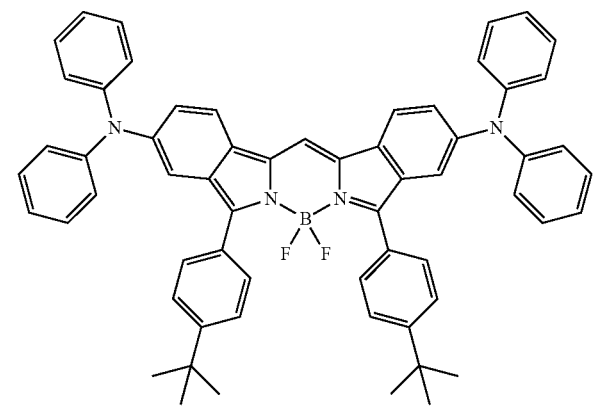
E-52
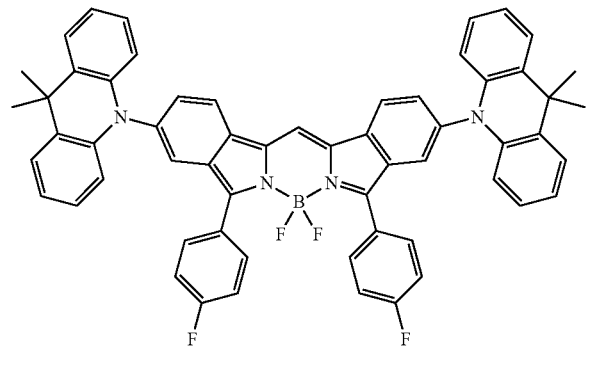
E-53
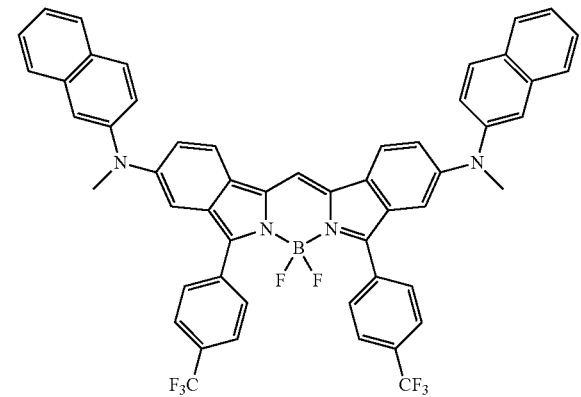
E-54
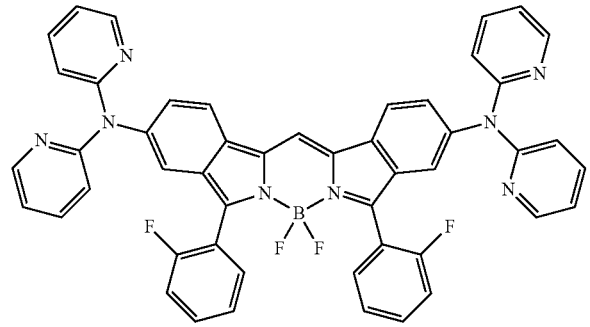
E-55
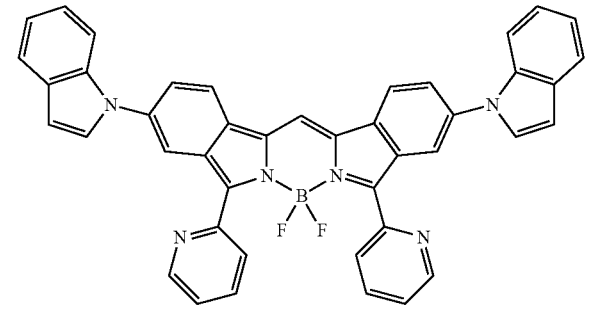

-continued
E-56
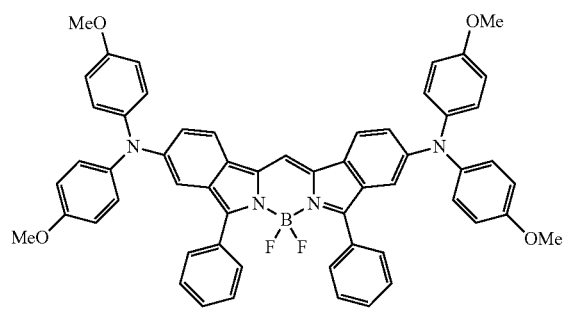
E-57
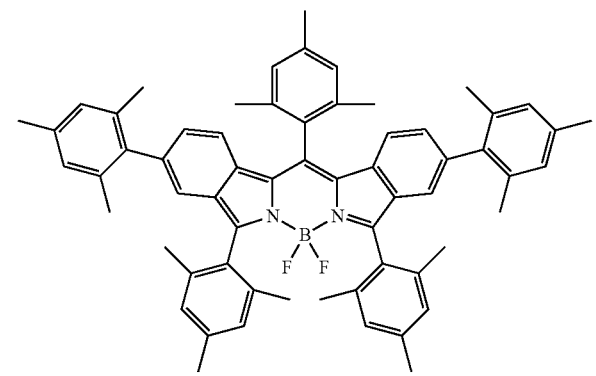
E-58
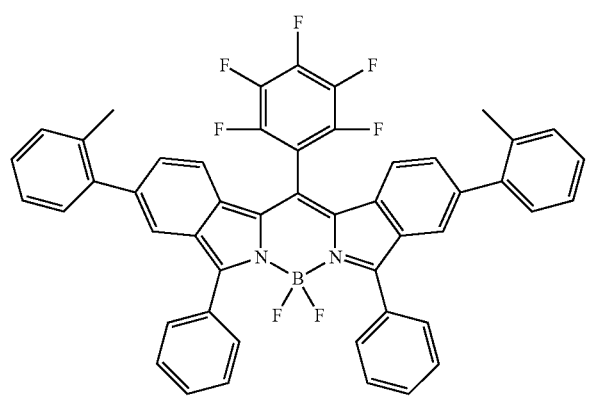
E-59
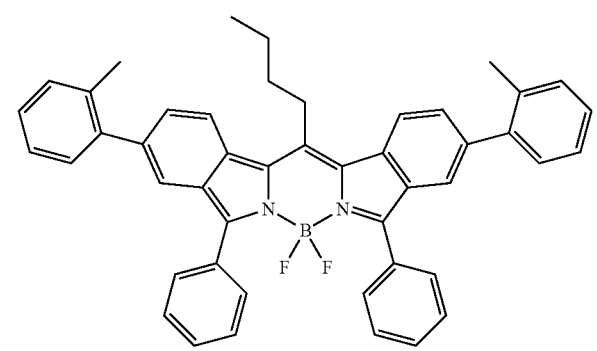
E-60
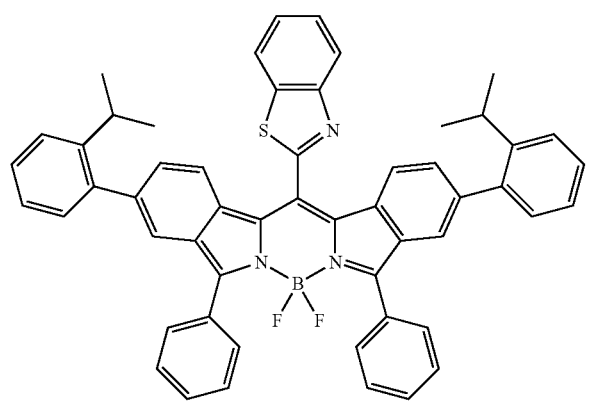
E-61
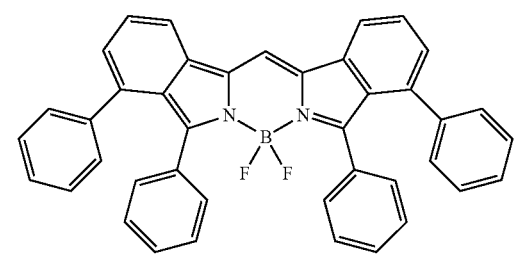
E-62
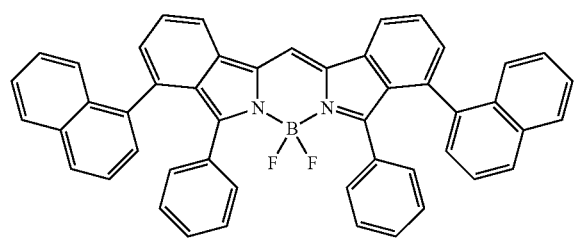
E-63
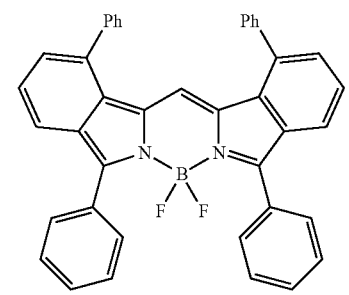

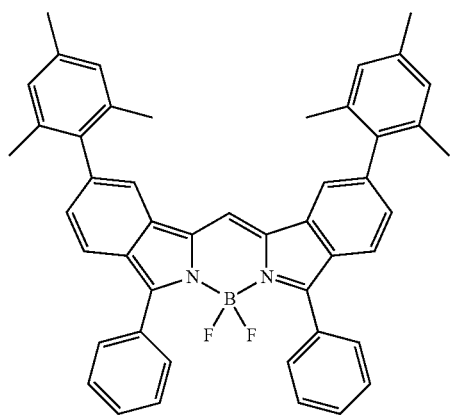

E-64

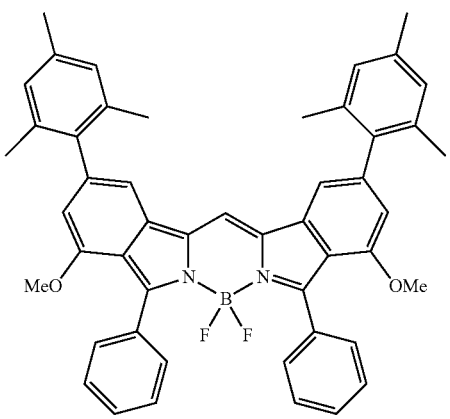

E-65

<As to Specific Examples of Combination of Energy Donor Compound and Energy Acceptor Compound>

Specific examples of a combination of an energy donor compound and an energy acceptor compound are shown below.

TABLE 1

| Donor | Acceptor | Donor | Acceptor | Donor | Acceptor |
|---|---|---|---|---|---|
| F-2 | F-43 | F-16 | F-64 | F-37 | F-43 |
| F-2 | F-44 | F-16 | F-69 | F-37 | F-44 |
| F-2 | F-46 | F-16 | F-70 | F-37 | F-46 |
| F-2 | F-51 | F-16 | F-71 | F-37 | F-51 |
| F-2 | F-55 | F-16 | F-72 | F-37 | F-55 |
| F-2 | F-69 | F-24 | F-43 | F-65 | F-43 |
| F-16 | F-38 | F-24 | F-44 | F-65 | F-44 |
| F-16 | F-39 | F-24 | F-46 | F-65 | F-46 |
| F-16 | F-41 | F-24 | F-51 | F-65 | F-51 |
| F-16 | F-42 | F-24 | F-55 | F-65 | F-55 |
| F-16 | F-43 | F-24 | F-69 | F-65 | F-69 |
| F-16 | F-45 | F-27 | F-43 | F-66 | F-43 |
| F-16 | F-46 | F-27 | F-44 | F-66 | F-44 |
| F-16 | F-48 | F-27 | F-46 | F-66 | F-46 |
| F-16 | F-49 | F-27 | F-51 | F-66 | F-51 |
| F-16 | F-50 | F-27 | F-55 | F-66 | F-55 |
| F-16 | F-51 | F-27 | F-69 | F-66 | F-69 |
| F-16 | F-52 | F-29 | F-43 | F-67 | F-43 |
| F-16 | F-53 | F-29 | F-44 | F-67 | F-44 |
| F-16 | F-54 | F-29 | F-46 | F-67 | F-46 |
| F-16 | F-55 | F-29 | F-51 | F-67 | F-51 |
| F-16 | F-56 | F-29 | F-55 | F-67 | F-55 |
| F-16 | F-57 | F-29 | F-69 | F-67 | F-69 |
| F-16 | F-58 | F-33 | F-43 | F-68 | F-43 |
| F-16 | F-59 | F-33 | F-44 | F-68 | F-44 |
| F-16 | F-60 | F-33 | F-46 | F-68 | F-46 |
| F-16 | F-61 | F-33 | F-51 | F-68 | F-51 |
| F-16 | F-62 | F-33 | F-55 | F-68 | F-55 |
| F-16 | F-63 | F-33 | F-69 | F-68 | F-69 |

TABLE 2

| Donor | Acceptor | Donor | Acceptor | Donor | Acceptor |
|---|---|---|---|---|---|
| E-4 | F-43 | E-16 | F-64 | F-16 | E-24 |
| E-4 | F-44 | E-16 | F-69 | F-19 | E-24 |
| E-4 | F-46 | E-16 | F-70 | F-20 | E-24 |
| E-4 | F-51 | E-16 | F-71 | F-21 | E-24 |
| E-4 | F-55 | E-16 | F-72 | F-23 | E-24 |
| E-4 | F-69 | E-20 | F-43 | F-24 | E-24 |
| E-16 | F-38 | E-20 | F-44 | F-25 | E-24 |
| E-16 | F-39 | E-20 | F-46 | F-26 | E-24 |
| E-16 | F-41 | E-20 | F-51 | F-27 | E-24 |
| E-16 | F-42 | E-20 | F-55 | F-28 | E-24 |
| E-16 | F-43 | E-20 | F-69 | F-29 | E-24 |
| E-16 | F-45 | E-57 | F-43 | F-30 | E-24 |
| E-16 | F-46 | E-57 | F-44 | F-31 | E-24 |
| E-16 | F-48 | E-57 | F-46 | F-32 | E-24 |
| E-16 | F-49 | E-57 | F-51 | F-33 | E-24 |
| E-16 | F-50 | E-57 | F-55 | F-34 | E-24 |
| E-16 | F-51 | E-57 | F-69 | F-36 | E-24 |
| E-16 | F-52 | F-1 | E-24 | F-37 | E-24 |
| E-16 | F-53 | F-2 | E-24 | F-65 | E-24 |
| E-16 | F-54 | F-3 | E-24 | F-66 | E-24 |
| E-16 | F-55 | F-4 | E-24 | F-67 | E-24 |
| E-16 | F-56 | F-5 | E-24 | F-68 | E-24 |
| E-16 | F-57 | F-6 | E-24 | F-2 | E-17 |
| E-16 | F-58 | F-7 | E-24 | F-16 | E-17 |
| E-16 | F-59 | F-8 | E-24 | F-33 | E-17 |
| E-16 | F-60 | F-12 | E-24 | F-65 | E-17 |
| E-16 | F-61 | F-13 | E-24 | F-66 | E-17 |
| E-16 | F-62 | F-14 | E-24 | F-67 | E-17 |
| E-16 | F-63 | F-15 | E-24 | F-68 | E-17 |

Regarding the selection of an energy donor compound and an energy acceptor compound, a compound with absorption in a short wavelength is the energy donor compound, a compound with absorption in a long wavelength is the energy acceptor compound, and in the case where the emission of the energy donor compound and the absorption of the energy acceptor compound overlap each other even a little, the compounds may be usable in the luminescent labeled particle. It is preferred that an absorption maximum wavelength of the energy acceptor compound is on the longer wavelength side by about 10 to 100 nm than an absorption wavelength of the energy donor compound. It is more preferred that an absorption maximum wavelength of the energy acceptor compound is on the longer wavelength side by about 10 to 70 nm than an absorption wavelength of the energy donor compound.

How longer the emission wavelength of the energy donor compound is than absorption wavelength (the size of the Stokes shift) varies depending on compounds, and thus it is difficult to be defined uniformly. However, since the compound represented by Formula (1) has maximum emission in a wavelength which is longer than the absorption maximum wavelength by about 30 nm, and has an emission spectrum in a range of the wavelength to a wavelength longer than the wavelength by about 100 nm, it is assumed that an energy transfer system can be realized by combined use of an acceptor compound with absorption in the vicinity of the emission spectrum.

The absorption wavelength of each compound not only can be measured after synthesizing the compounds, but also can be predicted from calculation by Gaussian or the like. Additionally, it is possible to estimate a combination of the energy donor compound and the energy acceptor compound from the relationship between the calculated values.

In the present invention, the size of the Stokes shift is preferably 25 nm or more, more preferably 30 nm or more, still more preferably 35 nm or more, even more preferably 40 nm or more, even still more preferably 45 nm or more, particularly preferably 50 nm or more, and most preferably 60 nm or more. An upper limit of the size of the Stokes shift is not particularly limited, but is generally 150 nm or less.

<Amount of Use of Compounds Represented by Formulae (1) to (6)>

There is no particular limitation on the content of the compound represented by Formula (1) for the particles used in the present invention (that is, the particles before addition of the compound represented by Formula (1)) as long as the effect of the present invention is not impaired, but the content is preferably 0.5 μmol/g to 400 μmol/g, more preferably 1 μmol/g to 300 μmol/g, still more preferably 2 μmol/g to 200 μmol/g, and particularly preferably 3 μmol/g to 100 μmol/g.

There is no particular limitation on the content of the compounds represented by Formulae (1) to (6) for the particles used in the present invention (that is, the particles before addition of the compounds represented by Formulae (1) to (6)) as long as the effect of the present invention is not impaired, but the content is preferably 0.1% by mass to 30% by mass, more preferably 0.2% by mass to 20% by mass, still more preferably 0.3% by mass to 10% by mass, and particularly preferably 0.4% by mass to 8% by mass.

In the luminescent labeled particle, at least one kind of compound represented by Formulae (1) to (6) is used, but two or more kinds of compounds represented by Formulae (1) to (6) may be used. In the case where two or more kinds of compounds represented by Formulae (1) to (6) are used, it is preferred that the total amount of the compounds falls within the above range.

In the case of using the combination of the energy donor compound and the energy acceptor compound, the molar ratio of the energy donor compound to the energy acceptor compound is preferably 1:10 to 20:1, more preferably 1:10 to 10:1, and still more preferably 1:5 to 10:1.

In the case where at least one kind of compound represented by Formula (1) is used as the energy donor compound and at least one kind of compound represented by Formula (1) is used as the energy acceptor compound, two or more kinds of compounds represented by Formula (1) may be used as the energy donor compound, and two or more kinds of compounds represented by Formula (1) may be used as the energy acceptor compound. In the above case, it is preferred that the total amount of the compounds represented by Formula (1) to be used falls within the above range.

<Method for Producing Compounds Represented by Formulae (1) to (6)>

The compounds represented by Formulae (1) to (6) can be produced, for example, according to a synthesis scheme shown in Examples which will be described later.

As an example, the synthesis of Compound (1) is outlined below. 3-Ethyl-2,4-dimethylpyrrole and trifluoroacetic acid are added to a mixture of 3,5-bis(trifluoromethyl)benzaldehyde and dichloromethane while cooling with water, followed by stirring at room temperature, chloranil is added while cooling with water, followed by stirring at room temperature, and diisopropylethylamine is added dropwise while cooling with water, followed by stirring at room temperature. Subsequently, a boron trifluoride-diethyl ether complex is added dropwise while cooling with water, and the reaction is carried out by stirring the mixture at room temperature, whereby Compound (1-A) can be synthesized. Subsequently, Compound (1-A), 115 mg of 2,4,6-trimethylbenzaldehyde, and dehydrated toluene are mixed and stirred at room temperature. Piperidine and one piece of p-toluenesulfonic acid monohydrate are added, and the mixture is stirred while distilling off the solvent. After allowing to cool, dehydrated toluene is added and the reaction is carried out by stirring the mixture while distilling off the solvent, whereby Compound (1) can be produced.

As another example, Compound (3) can be produced through Compound (3-A), Compound (3-B), and Compound (3-C) from 3,5-bis(trifluoromethyl)benzaldehyde and 2,4-dimethylpyrrole as starting compounds according to the synthesis scheme of <Synthesis Example 2> in Examples which will be described later.

Compound (1) and Compound (3) are within the definition of the compound represented by Formula (1). The compound represented by Formula (1) other than Compound (1) and Compound (3) can also be produced by substituting the compound used in the reaction with a compound having a substituent corresponding to a desired target compound represented by Formula (1).

<Method for Producing Compound Represented by Formula (10)>

The compound represented by Formula (10) can be produced, for example, according to the following synthesis scheme.

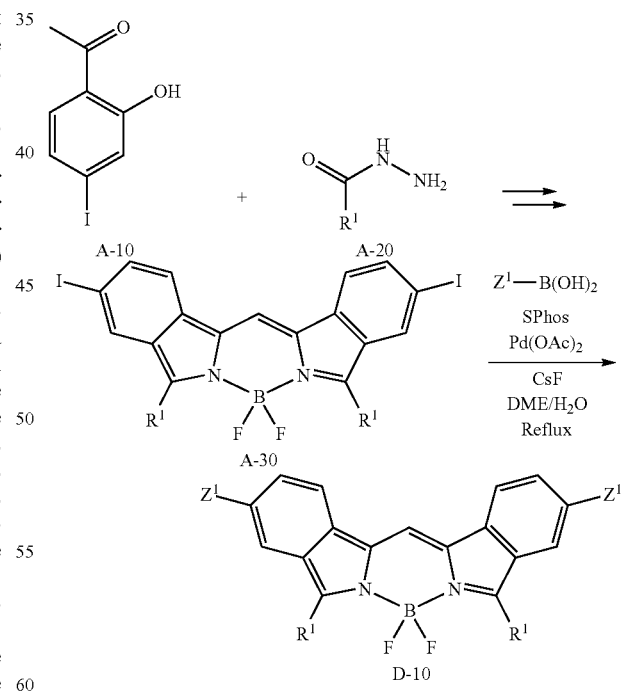

The definitions of $R^1$ and $Z^1$ in the above synthesis scheme are the same as the definitions of $R^1$ and $Z^1$ in formula (10).

Compound A-30 can be synthesized by reacting Compound A-10 with Compound A-20 according to the method described in Macromolecules 2010, 43, 193 to 200. Then, Compound A-30, a compound represented by a formula of $Z^1$—$B(OH)_2$, and cesium fluoride (CsF) are added to a mixed solution of dimethoxyethane (DME) and water, and vacuum drawing and nitrogen substitution are repeated for degassing. Compound D-10 can be produced by adding palladium acetate ($Pd(OAc)_2$) and 2-dicyclohexylphosphino-2',6'-dimethoxybiphenyl (SPhos) thereto, raising the temperature, and performing the reaction under reflux for a predetermined time (for example, 2 to 24 hours).

Compound D-10 is within the definition of the compound represented by Formula (10). The compound represented by Formula (10) other than Compound D-10 can also be produced by substituting any one or more of Compound A-10, Compound A-20, or the compound represented by a formula of $Z^1$—$B(OH)_2$ with corresponding compounds.

<Particle>

Labeled particles include particles. The material and form of the particles are not particularly limited, and for example, organic polymer particles such as polystyrene beads or inorganic particles such as glass beads can be used. Specific examples of the material of the particles include a homopolymer obtained by polymerizing a monomer such as styrene, methacrylic acid, glycidyl (meth)acrylate, butadiene, vinyl chloride, vinyl acetate acrylate, methyl methacrylate, ethyl methacrylate, phenyl methacrylate, or butyl methacrylate, and a copolymer obtained by polymerizing two or more monomers. A latex in which the homopolymer or the copolymer is uniformly suspended may also be used. Examples of the particles include other organic polymer powders, inorganic substance powders, microorganisms, blood cells, cell membrane fragments, liposomes, and microcapsules. Latex particles are preferable as particles.

In the case where latex particles are used, specific examples of the material of the latex include polystyrene, a styrene-acrylic acid copolymer, a styrene-methacrylic acid copolymer, a styrene-glycidyl (meth)acrylate copolymer, a styrene-styrene sulfonate copolymer, a methacrylic acid polymer, an acrylic acid polymer, an acrylonitrile-butadiene-styrene copolymer, a vinyl chloride-acrylic acid ester copolymer, and polyvinyl acetate acrylate. As the latex, a copolymer containing at least styrene as a monomer is preferable, and a copolymer of styrene and acrylic acid or methacrylic acid is particularly preferable. The method for preparing the latex is not particularly limited, and the latex can be prepared by any polymerization method. However, in the case where the luminescent labeled particle is used by labeling with an antibody, the presence of a surfactant makes it difficult to immobilize the antibody. Therefore, for the preparation of a latex, emulsifier-free emulsion polymerization, that is, emulsion polymerization without using an emulsifier such as a surfactant is preferable.

<Luminescent Labeled Particle>

By including the compound represented by Formula (1), the luminescent labeled particle in the present invention has an emission maximum wavelength in the long wavelength range of 680 nm or longer and exhibits a high quantum yield.

The emission maximum wavelength refers to a wavelength at which the absorbance becomes the largest in the absorption spectrum.

The emission maximum wavelength of the luminescent labeled particle is preferably 680 nm or longer, more preferably 700 nm or longer, and particularly preferably 720 nm or longer. An upper limit of the emission maximum wavelength of the luminescent labeled particle of the present invention is not particularly limited, but is preferably 900 nm or shorter and more preferably 800 nm or shorter.

The emission maximum wavelength of the luminescent labeled particle can be measured using a commercially available fluorescence spectrophotometer, and for example, can be measured using a fluorescence spectrophotometer RF-5300PC manufactured by Shimadzu Corporation.

The quantum yield of the luminescent labeled particles is the ratio of the number of photons emitted as fluorescence to the number of photons absorbed by luminescent labeled particles.

The quantum yield of the luminescent labeled particles is preferably 0.25 or more, more preferably 0.4 or more, still more preferably 0.5 or more, even more preferably 0.6 or more, and particularly preferably 0.7 or more. An upper limit of the quantum yield is not particularly limited, but generally is 1.0 or less.

The quantum yield of the luminescent labeled particles can be measured using a commercially available quantum yield measuring apparatus, and for example, can be measured using an absolute PL quantum yield spectrometer C9920-02 manufactured by Hamamatsu Photonics K.K.

(Method for Measuring Average Particle Diameter (Average Particle Size) of Luminescent Labeled Particles)

The average particle diameter of the luminescent labeled particles varies depending on the material of the particles, the concentration range for measuring the test substance, the measuring device, and the like, but is preferably in the range of 0.001 to 10 μm (more preferably 0.01 to 1 μm), more preferably in the range of 30 to 500 nm, still more preferably in the range of 50 to 300 nm, particularly preferably in the range of 80 to 200 nm, and most preferably in the range of 100 to 150 nm. The average particle diameter of the luminescent labeled particles that can be used in the present invention can be measured with a commercially available particle size distribution meter or the like. As a method for measuring the particle size distribution, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and apparatuses corresponding to the respective principles are commercially available. Among these measurement methods, it is preferred to measure the average particle diameter of the luminescent labeled particles using a dynamic light scattering method from the viewpoint of the particle size range and ease of measurement. Examples of commercially available measuring apparatuses using dynamic light scattering include NANOTRAC UPA (Nikkiso Co., Ltd.), dynamic light-scattering particle size analyzer LB-550 (HORIBA, Ltd.), fiber-optics particle analyzer FPAR-1000 (Otsuka Electronics Co., Ltd.), and the like. In the present invention, the average particle diameter is obtained as a median diameter (d=50) measured at 25° C. under the conditions of a viscosity of 0.8872 CP and a refractive index of water of 1.330.

<Method for Producing Luminescent Labeled Particles>

The method for producing the luminescent labeled particles is not particularly limited, but the luminescent particles can be produced by mixing particles with at least one kind of compound represented by Formula (1). For example, the luminescent labeled particles can be prepared by adding the compound represented by Formula (1) to particles such as latex particles. More specifically, the luminescent labeled particles can be produced by adding a solution containing the compound represented by Formula (1) to a dispersion liquid of particles containing at least one of water or a water-soluble organic solvent (tetrahydrofuran, methanol, or the like) and stirring the mixture.

In the present invention, a dispersion liquid containing the above-described luminescent labeled particle of the present invention may be prepared.

The dispersion liquid can be produced by dispersing the luminescent labeled particles of the present invention in a dispersion medium. Examples of the dispersion medium include water, an organic solvent, and a mixture of water and an organic solvent. An alcohol such as methanol, ethanol, or isopropanol, an ether-based solvent such as tetrahydrofuran, or the like can be used as the organic solvent.

The concentration of the solid content of the luminescent labeled particles in the dispersion liquid is not particularly limited, but is generally 0.1% to 20% by mass, preferably 0.5% to 10% by mass, and more preferably 1% to 5% by mass.

(Modification of Luminescent Labeled Particle by First Binding Substance)

The method for immobilizing the first binding substance on the luminescent labeled particle is described, for example, in JP2000-206115A or the protocol attached to FluoSpheres (registered trademark) polystyrene microsphere F8813 of Thermo Fisher Scientific Inc., and any known method for preparing a reagent for an immunoagglutination reaction can be used. In addition, as a principle of immobilizing an antibody as a binding substance on particles, any principle of physical adsorption or a chemical bond by a covalent bond can be adopted. As a blocking agent (that is, the first blocking agent) covering a particle surface which is not coated with the antibody after immobilizing the antibody on the particle, for example, albumin (such as BSA), skim milk, casein, a soybean-derived component, a fish-derived component, polyethylene glycol, or the like, and commercially available blocking agents for an immune reaction or the like containing the substances as well as substances having the same property as that of the substances can be used. These blocking agents can be subjected to pretreatment such as partial modification with heat, acid, alkali, or the like, as necessary. Furthermore, as the first blocking agent, an antibody (globulin) which is not capable of binding to the measurement target substance or a protein (Protein A and Protein G) which is not used in a test area can be used.

A specific method for immobilizing an antibody on particles is exemplified below. An antibody solution of which concentration is adjusted to 0.01 to 20 mg/mL is added to a liquid in which the particles are dispersed such that the concentration of the solid content of the particles becomes 0.1% to 10% by mass, and mixing is performed. Stirring is continued for 5 minutes to 48 hours under a condition of a temperature of 4° C. to 50° C. Next, the particle and the solution are separated by centrifugation or other methods to sufficiently remove antibodies not bound to the particle contained in the solution. Then, an operation of washing the particle with a buffer solution is repeated 0 to 10 times. It is preferred that after carrying out an operation of mixing the particle and the antibody and binding the antibody to the particle, a portion of the particle surface to which the antibody is not bound is protected using a blocking agent such as the components which do not participate in the antigen-antibody reaction, preferably protein, and more preferably globulin, albumin, BLOCKACE (registered trademark), skim milk, and casein.

In the case where the antigen, the antibody, or the like is immobilized on the particle, a stabilizer can be added, as necessary. The stabilizer is not particularly limited as long as the stabilizer stabilizes an antigen or an antibody, like a synthetic polymer or a natural polymer, such as polysaccharides or sucrose, and commercially available stabilizers such as Immunoassay Stabilizer (Advanced Biotechnologies Inc.) can also be used.

The labeled particle having the first binding substance is contained in the kit according to the embodiment of the present invention, and an aspect in which the labeled particle is contained in a container, for example, a cup, which is a part of the kit is preferable. In this case, the measurement target substance in the biological sample can be bound to the first binding substance by injecting the biological sample into a container containing the labeled particle, and mixing and stirring components.

(Substrate)

In the present invention, in order to achieve high-sensitive measurement, it is preferred to adopt a measurement method for performing surface plasmon fluorescence (SPF) detection described later. As a substrate in this case, it is preferred to use a substrate having a metal film on a surface. A metal constituting the metal film is not particularly limited as long as the metal can cause surface plasmon resonance. Preferably, free-electron metals such as gold, silver, copper, aluminum, or platinum can be mentioned, and gold is particularly preferable. In the case where gold is used, the detection area described later is on the gold film. The metals can be used alone or in a combination thereof. Further, in consideration of the adhesiveness to the substrate, an intervening layer including chromium or the like may be provided between the substrate and the layer including metal. Thickness of the metal film is randomly determined, but for example, is preferably 1 nm or more and 500 nm or less, and particularly preferably 10 nm or more and 200 nm or less. In the case where the thickness exceeds 500 nm, a surface plasmon phenomenon of a medium cannot be detected sufficiently. Moreover, in the case of providing an intervening layer which includes chromium or the like, it is preferred that thickness of the intervening layer is 0.1 nm or more and 10 nm or less.

The formation of the metal film may be carried out by a conventional method, and can be carried out, for example, by a sputtering method, a vapor deposition method, an ion plating method, an electroplating method, a non-electrolytic plating method, or the like. In order to provide a mixed layer of a substrate material and a metal film and improve the adhesiveness of the metal film, it is preferred to prepare the metal film by the sputtering method. In this case, thickness of the mixed layer of the substrate material and the metal film is not particularly limited as long as sufficient adhesiveness can be ensured, and 10 nm or less is preferable.

The metal film is preferably disposed on the substrate. Herein, "disposed on the substrate" includes a case where the metal film is disposed to be in direct contact with the substrate, and a case where the metal film is disposed not in direct contact with the substrate but in contact with the substrate through other layers. The material of the substrate that can be used in the present invention is, for example, optical glass such as BK7 (borosilicate glass), which is a type of general optical glass, or synthetic resin, specifically a substance formed of a material transparent to laser light, such as polymethyl methacrylate, polyethylene terephthalate, polycarbonate, or a cycloolefin polymer can be used. Such a substrate is preferably a material that does not exhibit anisotropy with respect to polarization and has excellent processability.

As a preferred aspect of the substrate for SPF detection, a substrate in which a gold film is vapor-deposited on polymethyl methacrylate (PMMA) can be mentioned.

The substrate comprises a detection area having a second binding substance that is capable of binding to any one of the measurement target substance or the first binding substance.

(Second Binding Substance)

A second binding substance is a substance capable of binding to the measurement target substance or a substance capable of binding to the first binding substance. In the case where quantification is performed by a sandwich assay method, a substance capable of binding to the measurement target substance can be used as the second binding substance. In the case where quantification is performed by a competition method, a substance capable of binding to the first binding substance can be used as the second binding substance. In the present invention, quantification is preferably performed by a competition method, and it is preferred to use a substance capable of binding to the first binding substance as the second binding substance.

The second binding substance is not particularly limited, but preferred examples thereof include an antigen, an antibody, or a complex thereof, an antigen is preferable, and particularly preferably a measurement target substance (this is a substance capable of binding to the first binding substance) is used as the second binding substance.

In the case where the measurement target substance is used as the second binding substance, the second binding substance is preferably a conjugate of the measurement target substance and a carrier. The carrier means a substance to which a plurality of molecules of the measurement target substance can be bound. As an example of a preferred carrier, proteins or the like are mentioned, and among them, specifically, bovine serum albumin or the like can be mentioned.

In the case where the measurement target substance is bile acid, the second binding substance particularly preferably includes cholic acid and/or a cholic acid-albumin conjugate, deoxycholic acid and/or a deoxycholic acid-albumin conjugate, and chenodeoxycholic acid and/or a chenodeoxycholic acid-albumin conjugate. In the case where the measurement target substance is progesterone, the second binding substance is preferably a progesterone-albumin conjugate.

(Method for Immobilizing Second Binding Substance on Substrate)

A method for immobilizing a second binding substance on a substrate is described in, for example, Tech Notes Vols. 2 to 12 provided by Nunc Corporation and all known methods for preparing a general Enzyme-linked immunosorbent assay (ELISA) reagent can be used. In addition, surface modification may be performed by placing a self-assembled monolayer (SAM) or the like on a substrate, and as a method for immobilizing the second binding substance on the substrate, any method using physical adsorption or a chemical bond by a covalent bond can be adopted. As a blocking agent (second blocking agent) covering the substance surface which is not coated with the second binding substance after immobilizing the second binding substance on the substrate, known substances, for example, BSA, globulin, skim milk, casein, a soybean-derived component, a fish-derived component, polyethylene glycol, or the like, and commercially available blocking agents for an immune reaction or the like containing the substances as well as substances having the same property as that of the substances can be used. These blocking agents can be subjected to pretreatment such as partial modification with heat, acid, alkali, or the like, as necessary.

(Detection Area <Test Area>)

In the present invention, a test area can be provided on the substrate to detect the presence or absence of the measurement target substance in the biological sample. In this test area, for example, an antigen can be quantified by capturing an antigen which is a measurement target substance and detecting and quantifying the amount of labels bound to the antigen. Alternatively, the antigen can be quantified by a method in which only the labels bound to the antigen is caused not to be bound, only labels not bound to the antigen is captured, and the amount of labels bound to the antigen is calculated. This detection method is referred to as a competition method and herein, the substrate relating to the competition method will be described.

It is preferred that the test area of the substrate has a site for reacting with the binding substance (for example, antibody) present on the labeled particle. As a preferred aspect of the present invention, an aspect in which the antigen present in the biological sample is on the test area of the substrate is preferable. In this case, the antigen and BSA are reacted in the presence of a condensing agent to prepare an antigen-BSA conjugate, and a test area can be prepared by adsorbing the conjugate onto the test area. The antigen-BSA conjugate which is the measurement target substance can be bound to the test area on a substrate by a method in which the conjugate is dissolved in a buffer solution, and the resultant is spotted on the substrate and allowed to stand for a predetermined time, the supernatant is sucked, and drying is performed.

(Reference Area <Control Area>)

In the present invention, in order to minimize influence of the measurement environment, particularly the measurement temperature, as much as possible, a control area is provided on the substrate, and the information on the test area is standardized by the information on the control area, thereby enabling the environmental dependency to be suppressed extremely low. The control area is preferably designed to be capable of binding to all the labels regardless of the amount of the measurement target substance present in the biological sample to be used. It is preferred to provide an antibody that interacts with all the antibodies present on the labeled particle. By designing in this manner to standardize the information on the test area by the information on the control area, for example, even in the case where the flow of the biological sample or the reaction rate is affected in the low temperature environment, such influence can be cancelled by the standardization, and thus it becomes possible to obtain a result that is always precise and not affected by the measurement environment.

An antibody to be present in the control area preferably has a function of recognizing a binding substance (for example, antibody) present on the labeled particle, in the case where the antibody is derived from a mouse, an anti-mouse antibody is preferable, and in the case where the antibody on the labeled particle is derived from a goat, an anti-goat antibody is preferable. These antibodies on the control area can be bound to a substrate by a method in which the antibodies are dissolved in a buffer solution, and the resultant is spotted on the substrate and allowed to stand for a predetermined time, the supernatant is sucked, and drying is performed.

(Blocking Agent)

For example, in a competition method, not only a negative biological sample which does not contain a measurement target substance but also a biological sample which becomes negative by reacting to even a positive biological sample which contains a measurement target substance are present, and the solution to the problem of deviation at a high value is recognized as an issue. The cause of the false negative is not clear, but it is considered that the presence of labeled particles which are originally not desired to bind due to nonspecific interaction between the labeled particle surface not covered with the antibody and the detection area (test area) is one of the causes. Moreover, in the case where the same substance as the substance present on the test area is present on the surface of the labeled particle, and a free antibody or the like is present in the biological sample, even in the measurement of a positive biological sample containing the measurement target substance, the antibody may be detected as negative by binding to both the substances present on the test area and the substance on the surface of the labeled particle.

In general, blocking with BSA is used to suppress nonspecific adsorption onto a solid phase surface (for example, a labeled particle surface, and a gold film surface of a substrate).

As an immunoglobulin other than the immunoglobulin capable of binding to the measurement target substance, specifically, an antiserum prepared from a serum of an animal immunized with an antigen different from the measurement target substance, an immunoglobulin fraction purified from the antiserum, a monoclonal antibody obtained by cell fusion using spleen cells of an animal immunized with the measurement target substance, or a fragment thereof [for example, F(ab')$_2$, Fab, Fab', or Fv] can be used. Preparation of these antibodies can be performed by a conventional method. Furthermore, the antibody may be modified as in the case of a chimeric antibody or the like, or a commercially available antibody or an antibody prepared from an animal serum or culture supernatant by known methods can be used.

(Antibody)

In the present invention, antibodies can be used regardless of animal species or subclasses thereof. For example, an antibody that can be used in the present invention is an antibody derived from an organism in which an immune reaction can occur, such as mice, rats, hamsters, goats, rabbits, sheep, cows, or chickens, specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, chicken IgY, and the like, and either polyclonal or monoclonal antibody can be used. A fragmented antibody is a molecule derived from a complete antibody, having at least one antigen binding site, and is specifically Fab, F(ab')$_2$, or the like. These fragmented antibodies are molecules obtained by an enzyme or chemical treatment or by using genetic engineering techniques.

(Other Elements of Kit)

The kit according to the embodiment of the present invention is used in a method for measuring a measurement target substance, in the case where the measurement target substance is bile acid, the kit is a kit for bile acid measurement and diagnosis, and in the case where the measurement target substance is progesterone, the kit is a kit for progesterone measurement and diagnosis. In the present invention, in the case of performing measurement of a measurement target substance, the kit includes a substrate on which a second binding substance is immobilized, and a sensor chip including a member holding labeled particles such as fluorescent particles, but may include various instruments or apparatuses used in measurement of a measurement target substance, such as a surface plasmon excitation apparatus and a fluorescence measurement device. Furthermore, a sample containing a known amount of the measurement target substance, an instruction manual, or the like may be included as an element of the kit.

[Method for Measuring Measurement Target Substance in Biological Sample]

The method for measuring a measurement target substance in a biological sample according to the embodiment of the present invention is a method including a reaction step of reacting a biological sample with a labeled particle having a first binding substance capable of binding to a measurement target substance, a capturing step of capturing the labeled particle on a substrate having a second binding substance capable of binding to any one of the measurement target substance or the first binding substance by bringing a reaction product obtained in the reaction step into contact with the substrate, and a label information acquisition step of acquiring label information related to the measurement target substance, in which the labeled particle is a luminescent labeled particle containing at least one kind of compound represented by Formula (1) and a particle.

In the present invention, the measurement target substance is measured by the measurement target substance-related label information acquisition step of acquiring label information related to the amount of the measurement target substance.

The measurement in the present invention is interpreted as the broadest concept as long as the measurement is measurement of the amount of the measurement target substance. As a specific embodiment of the measurement method, a competition method and a sandwich method are mentioned, and the competition method is preferable.

As an example of the competition method, a case of quantifying progesterone is described below. The same can also be applied to a case of quantifying substances other than progesterone.

In the competition method, first, a progesterone immunoassay substrate on which a progesterone-albumin conjugate is immobilized is brought into contact with a biological sample containing progesterone and an anti-progesterone antibody-labeled fluorescent particle. In the case where progesterone is not present in the biological sample, an antigen-antibody reaction occurs on the substrate by the anti-progesterone antibody-labeled fluorescent particle and progesterone on the substrate (that is, progesterone in a progesterone-albumin conjugate). On the other hand, in the case where progesterone is present in the biological sample, an antigen-antibody reaction occurs between progesterone in the biological sample and the anti-progesterone antibody-labeled fluorescent particle, and an antigen-antibody reaction between the anti-progesterone antibody-labeled fluorescent particle and the progesterone on the substrate (that is, progesterone in the progesterone-albumin conjugate) is inhibited. After the above reaction is completed, anti-progesterone antibody-labeled fluorescent particles that do not bind to albumin on the substrate are removed. Then, by detecting a degree of formation of an immune complex (that is, the complex of the anti-progesterone antibody-labeled fluorescent particle and progesterone in the progesterone-albumin conjugate on the substrate) on the substrate as fluorescence intensity, the concentration of progesterone or the like in the biological sample can be measured.

The measurement form of the fluorescence in the competition method can adopt either plate reader measurement or flow measurement, and for example, measurement can be performed by the following method. In advance, a plurality of samples with known amounts of progesterone having different progesterone concentrations are prepared, and these samples and the anti-progesterone antibody-labeled fluorescent particles are mixed in advance. This liquid mixture is brought into contact with an area where the progesterone-albumin conjugate is immobilized. The fluorescence signal from the area where the progesterone-albumin conjugate is immobilized is measured as a plurality of fluorescence signals while the liquid mixture is in contact with the conjugate at specific time intervals. From the plurality of fluorescence signals, temporal change (slope) in the fluorescence amount is acquired at each progesterone concentration. The temporal change is plotted as a Y axis and the progesterone concentration is plotted as an X axis, and a relational expression of the progesterone concentration with respect to the temporal change in the fluorescence amount is acquired using an appropriate fitting method such as the least squares method. The amount of progesterone contained in the biological sample can be quantified using the result of the temporal change in the fluorescence amount using the biological sample to be tested based on the relational expression thus acquired.

It is preferred to perform this quantification of the amount of progesterone in a short time. Specifically, the quantification is preferably performed within 10 minutes, more preferably within 8 minutes, and still more preferably within 6 minutes. This quantification time preferably includes time required to convert the amount of progesterone which is contained in the biological sample, based on the result of the temporal change in the fluorescence amount acquired using the biological sample to be tested after the sample and the anti-progesterone antibody-labeled fluorescent particles are brought into contact with detection area where the progesterone-albumin conjugate is immobilized, by using the relational expression between the temporal change in the fluorescence amount and the progesterone concentration, which is acquired in advance using an appropriate fitting method such as the least squares method.

The sandwich method is not particularly limited and for example, the measurement target substance can be measured by the following procedure. A biological sample which may contain a measurement target substance and fluorescent particles having a first binding substance capable of binding to the measurement target substance are brought into contact with each other on a substrate. In the case where the measurement target substance is present in the biological sample, a binding reaction (such as an antigen-antibody reaction) occurs among the measurement target substance, the fluorescent particles, and the substrate. As a result, in the case where the measurement target substance is present in the biological sample, an immune complex including a second binding substance bound to the substrate, the measurement target substance, and the fluorescent particles having the first binding substance is formed. In the sandwich method, after a reaction among the second binding substance, the measurement target substance, and the fluorescent particles having the first binding substance is completed, fluorescent particles having a first binding substance, which do not form the above-mentioned immune complex, are removed and washing is performed. Next, the concentration of the measurement target substance or the like can be measured by detecting the degree of the formation of the immune complex as fluorescence intensity. The fluorescence intensity and the concentration of the measurement target substance have a positive correlation.

(Flow Channel)

In a preferred aspect of the present invention, a liquid mixture obtained by mixing a biological sample that may contain a measurement target substance and labeled particles having a first binding substance is applied onto a substrate and developed into a flow channel. The flow channel is not particularly limited as long as the flow channel is a passage that allows the biological sample and the labeled particles having the first binding substance to flow down to the detection area. A preferred aspect of the flow channel is a flow channel having a structure in which a spotting port for spotting a biological sample liquid containing the labeled particles having the first binding substance, a metal film as a detection area, and a flow channel beyond the metal film are provided and the biological sample can pass over the metal film. Preferably, a suction port can be provided on a side opposite to the spotting port with respect to the metal film.

(Surface Plasmon Fluorescence Measurement)

The method for detecting a label such as fluorescence in the present invention is not particularly limited. For example, it is preferred that fluorescence intensity is detected using a device capable of detecting fluorescence intensity, specifically, a microplate reader or a biosensor for performing fluorescence detection by surface plasmon excitation (SPF). Preferably, label information related to the amount of the measurement target substance can be acquired by fluorescence detection by using surface plasmon resonance.

A form of measurement of fluorescence may be plate reader measurement or flow measurement. In a fluorescence detection method by surface plasmon excitation (SPF method), the measurement can be performed with higher sensitivity than in a fluorescence detection method by epi-excitation (epi-fluorescence method).

As a surface plasmon fluorescence (SPF) biosensor, a sensor described in JP2008-249361A, comprising: an optical waveguide formed of a material which transmits excitation light of a predetermined wavelength; a metal film formed on one surface of the optical waveguide; a light source for generating a light beam; an optical system for passing the light beam through the optical waveguide and causing the light beam to be incident on an interface between the optical waveguide and the metal film at an incidence angle generating the surface plasmon; and fluorescence detection means for detecting fluorescence generated by being excited by an evanescent wave enhanced due to the surface plasmon can be used.

The fluorescence detection (SPF) system by surface plasmon excitation using the fluorescent particles of the present invention is preferably an assay method for detecting fluorescence from the fluorescent substance depending on the amount of the measurement target substance immobilized on the metal film on the substrate, and for example, is a method different from a so-called latex agglutination method in which a change in optical transparency by the progress of a reaction in a solution is detected as turbidity. In the latex agglutination method, an antibody-sensitized latex in a latex reagent and an antigen in a biological sample are bound to be agglutinated by an antibody reaction. The latex agglutination method is a method in which the agglutinate increases over time, and the antigen concentration is quantified from the change in absorbance per unit time obtained by irradiating the agglutinate with near-infrared light. In the present invention, it is possible to provide a substantially simple method for detecting a measurement target substance, as compared with the latex agglutination method.

(Standardization)

Furthermore, the method according to the embodiment of the present invention may be a method including: a labeled particle-related label information acquisition step of acquiring label information related to the amount of the labeled particle; and a standardization step of standardizing label information acquired in a measurement target substance-related label information acquisition step of acquiring label information related to the amount of the measurement target substance, by the label information acquired in the labeled particle-related label information acquisition step.

In a step of bringing a liquid mixture containing a biological sample and a labeled particle having a first binding substance capable of binding to the measurement target substance into contact with a substrate having a detection area (test area) and a reference area (control area) to generate the surface plasmon on the detection area and the reference area, and measuring intensity of emitted fluorescence, a step of measuring intensity of the fluorescence by the surface plasmon generated on the detection area is the measurement target substance-related label information acquisition step of acquiring label information related to the amount of the measurement target substance, and a step of measuring intensity of the fluorescence by the surface plasmon generated on the reference area is the labeled particle-related label information acquisition step. A step of acquiring an increase rate in the unit time of the fluorescence intensity acquired in these two steps as change rate of fluorescence signal values and dividing a change rate of signal values of the detection area by a change rate of the signal value of the reference area is a standardization step.

Hereinafter, the present invention will be described in more detail with reference to the Examples of the present invention. The materials, amounts of use, proportions, treatment contents, treatment procedures, and the like shown in the following Examples can be appropriately modified without departing from the spirit and scope of the present invention. Therefore, the scope of the present invention should not be interpreted restrictively by the following specific examples.

EXAMPLES

<1-1> Synthesis of Compound
The terms have the following meanings.
MS: mass spectrometry
ESI: electrospray ionization
NMR: nuclear magnetic resonance
Me: methyl group
Et: ethyl group
Bu: n-butyl group
PL: photoluminescence
THF: tetrahydrofuran
The structures of Compounds (1) to (12) are shown below.

Compound (1)

Compound (2)

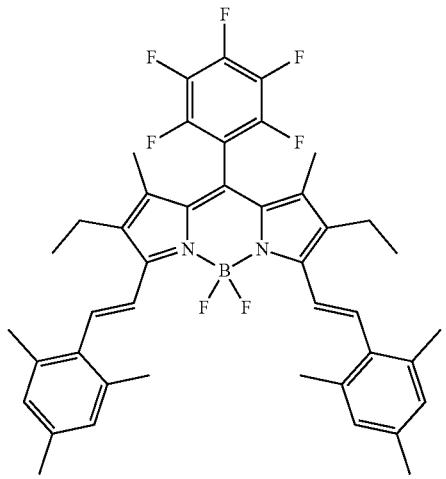

Compound (3)

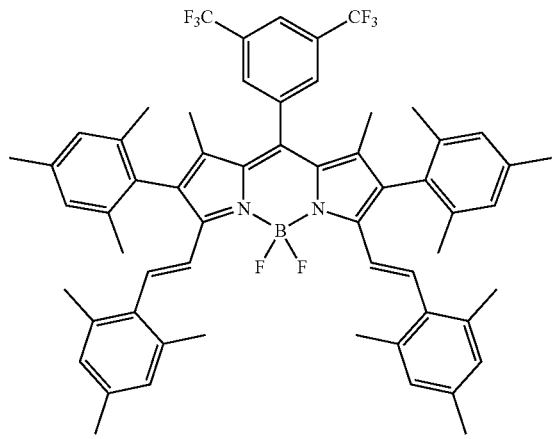

Compound (4)

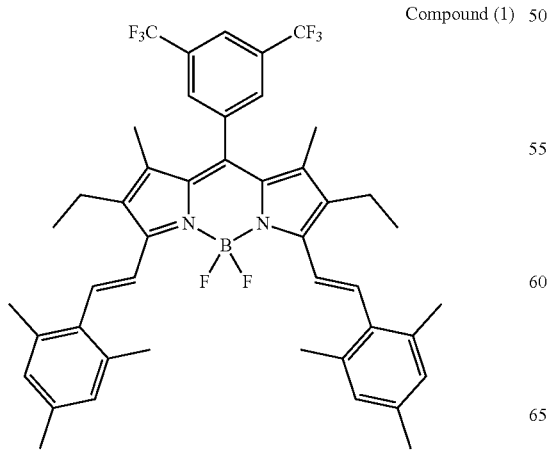

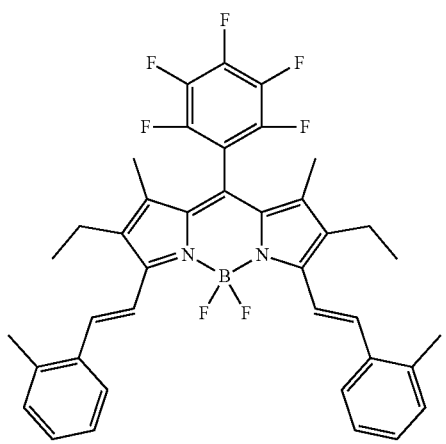

Compound (5)
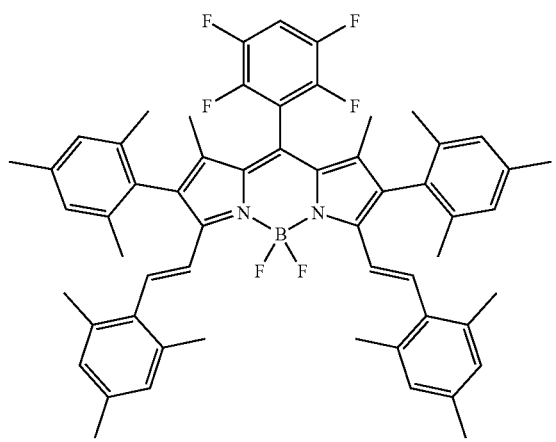
Compound (8)
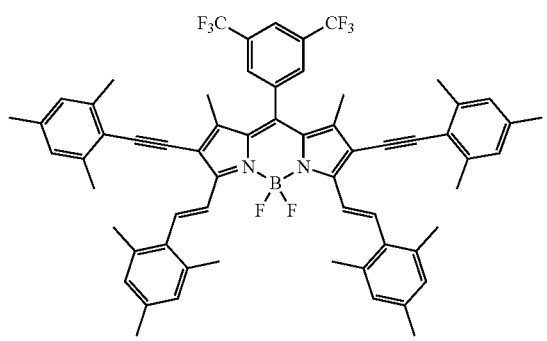
Compound (6)
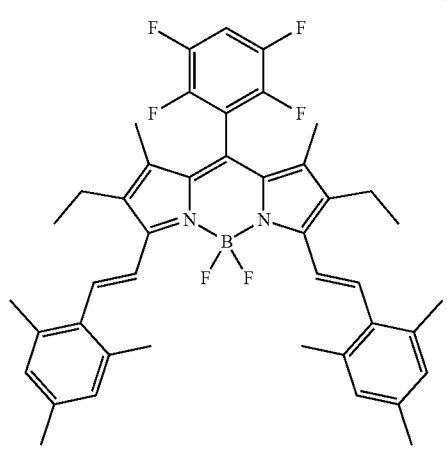
Compound (9)
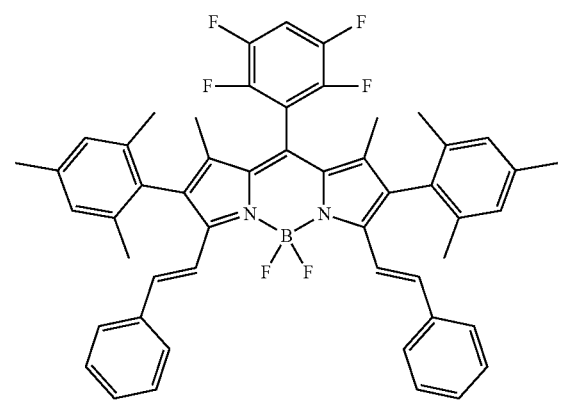
Compound (7)
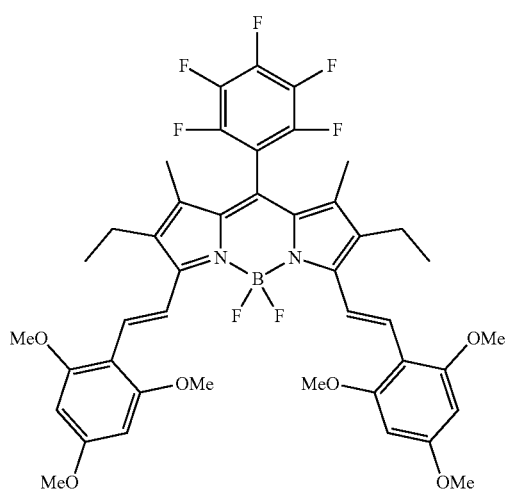
Compound (10)
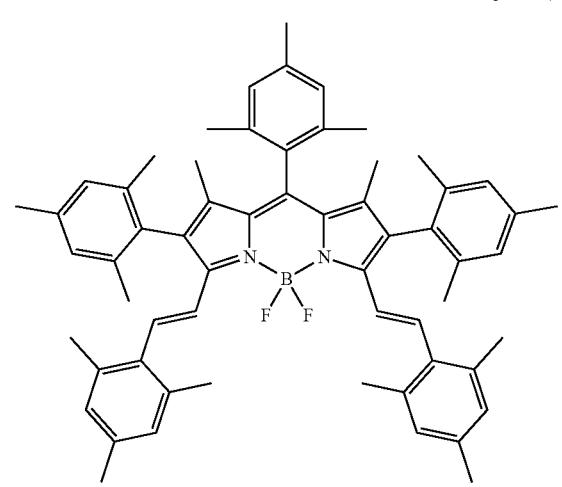

Compound (11)

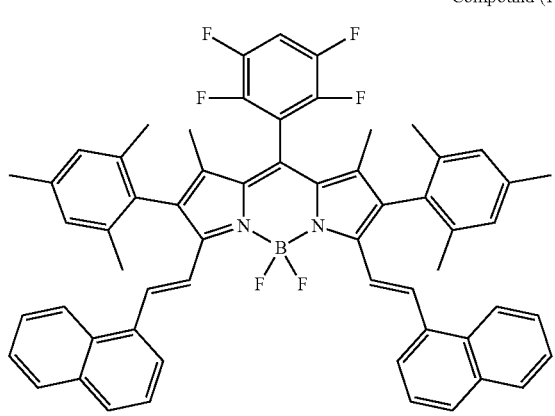

Compound (12)

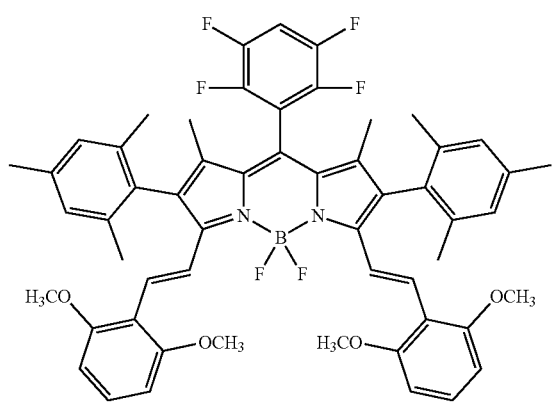

<Synthesis of Compound (1)>

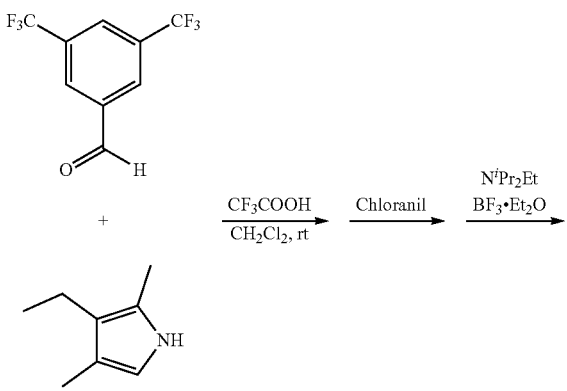

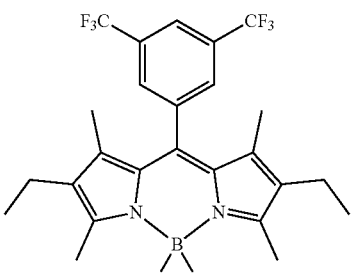

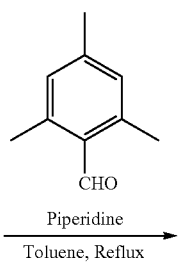

Compound (1-A)

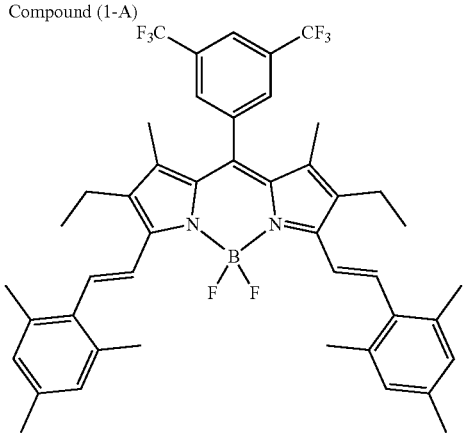

Compound (1)

Synthesis of Compound (1-A)

1.00 g of 3,5-bis(trifluoromethyl)benzaldehyde and 20 mL of dichloromethane were introduced into a 100 mL three-neck flask under a nitrogen atmosphere, followed by stirring at room temperature. While cooling with water, 0.98 g of 3-ethyl-2,4-dimethylpyrrole was added dropwise, followed by addition of two drops of trifluoroacetic acid and then stirring at room temperature for 30 minutes. 1.0 g of chloranil was added while cooling with water, followed by stirring at room temperature for 10 minutes, and then 3.67 g of diisopropylethylamine ($N^iPr_2Et$) was added dropwise while cooling with water, followed by stirring at room temperature for 15 minutes. Subsequently, 5.6 mL of a boron trifluoride-diethyl ether complex was added dropwise while cooling with water, followed by stirring at room temperature for 30 minutes. Saturated sodium hydrogen carbonate and toluene were added dropwise, and an organic layer obtained by extraction and liquid separation was preliminarily dried over anhydrous sodium sulfate and then concentrated under reduced pressure. The resulting crude product was purified by silica gel column chromatography (developing solvent: hexane/ethyl acetate) and then recrystallized from methanol to obtain 1.28 g of Compound (1-A).

$^1$H NMR (CDCl$_3$, 400 MHz): δ 8.03 (s, 1H), 7.83 (s, 2H), 2.54 (s, 6H), 2.31 (q, J=7.6 Hz, 4H), 1.21 (s, 6H), 1.00 (t, J=7.6 Hz, 6H).

Synthesis of Compound (1)

100 mg of Compound (1-A), 115 mg of 2,4,6-trimethylbenzaldehyde, and 5 mL of dehydrated toluene were introduced into a 100 mL three-neck flask, followed by stirring at room temperature. 1 mL of piperidine and one piece of p-toluenesulfonic acid monohydrate (manufactured by Wako Pure Chemical Industries, Ltd., special grade chemical) were added, followed by stirring for 1 hour while distilling off the solvent at 140° C. After allowing to cool, 5 mL of dehydrated toluene was added, followed by stirring for 1 hour while distilling off the solvent at 140° C. The crude product obtained by concentrating the reaction liquid under reduced pressure was purified by preparative TLC (developing solvent: hexane/ethyl acetate) and then recrystallized from methanol to obtain 71 mg of Compound (1). Identification of the compound was carried out by $^{1}$H-NMR and ESI-MS.

$^{1}$H NMR (CDCl$_3$, 400 MHz): δ 8.06 (s, 1H), 7.87 (s, 2H), 7.38 (d, J=17.2 Hz, 2H), 7.32 (d, J=17.2 Hz, 2H), 6.93 (s, 4H), 2.63 (q, J=7.6 Hz, 4H), 2.44 (s, 12H), 2.30 (s, 6H), 1.27 (s, 6H), 1.17 (t, J=7.6 Hz, 6H).

ESI-MS: [M−H]$^{-}$=775.8

<Synthesis of Compound (3)>

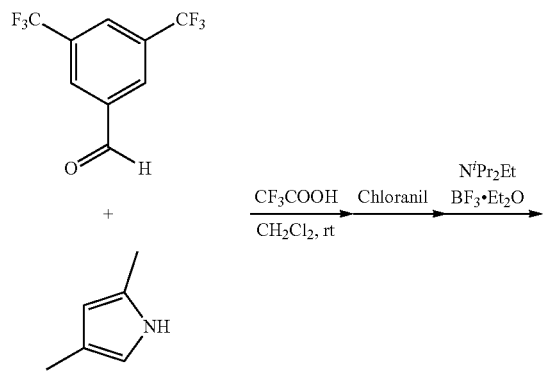

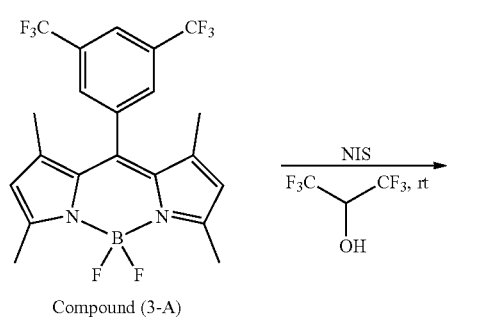

Compound (3-A)

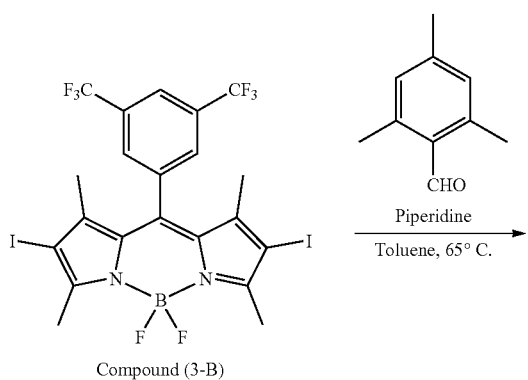

Compound (3-B)

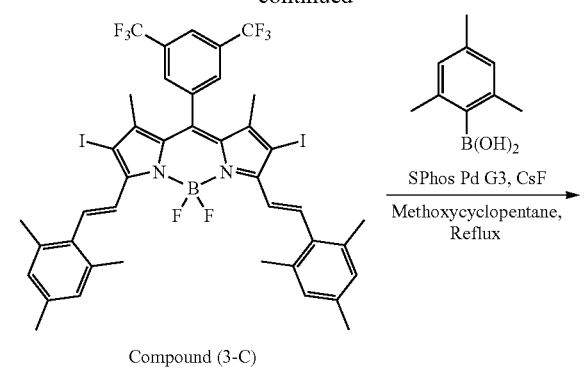

Compound (3-C)

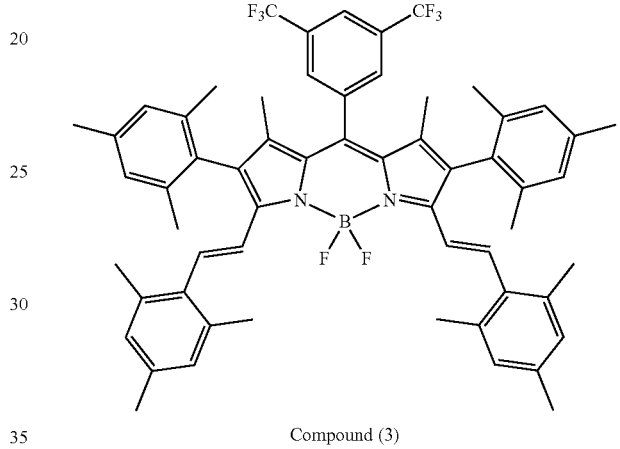

Compound (3)

Synthesis of Compound (3-A)

16.22 g of 3,5-bis(trifluoromethyl)benzaldehyde and 200 mL of dichloromethane were introduced into a 1 L three-neck flask under a nitrogen atmosphere, followed by stirring at room temperature. 15.75 g of 2,4-dimethylpyrrole was added dropwise while cooling with water, followed by addition of five drops of trifluoroacetic acid and then stirring at room temperature for 30 minutes. 19.45 g of chloranil was added while cooling with water, followed by stirring at room temperature for 30 minutes, and 80 mL of diisopropylethylamine (N$^i$Pr$_2$Et) was added dropwise while cooling with water, followed by stirring at room temperature for 30 minutes. Subsequently, 85 mL of a boron trifluoride-diethyl ether complex (BF$_3$.Et$_2$O) was added dropwise while cooling with water, followed by stirring at room temperature for 30 minutes. 400 mL of saturated sodium hydrogen carbonate was added dropwise, and an organic layer obtained by extraction and liquid separation was preliminarily dried over anhydrous sodium sulfate and then concentrated under reduced pressure. The resulting crude product was purified by silica gel column chromatography (developing solvent: hexane/ethyl acetate) and then recrystallized from ethanol to obtain 4.40 g of Compound (3-A).

Synthesis of Compound (3-B)

3.05 g of Compound (3-A) and 60 mL of 1,1,1,3,3,3-hexafluoro-2-propanol were introduced into a 300 mL three-neck flask, followed by stirring at room temperature. 3.60 g of N-iodosuccinimide was introduced, followed by stirring at room temperature for 1.5 hours. After concentrating the reaction liquid under reduced pressure, 50 mL of an aqueous sodium thiosulfate solution (10 g of sodium thiosulfate dissolved therein) and 100 mL of methylene chloride were added, and an organic layer obtained by extraction and liquid separation was preliminarily dried over anhydrous sodium sulfate and then concentrated under reduced pressure. The resulting crude product was recrystallized from ethanol to obtain 3.90 g of Compound (3-B).

Synthesis of Compound (3-C)

2.2 g of Compound (3-B), 2.6 g of 2,4,6-trimethylbenzaldehyde, and 40 mL of dehydrated toluene were introduced into a 100 mL three-neck flask, followed by stirring at room temperature. 4 mL of piperidine was introduced, followed by stirring at 65° C. for 1 hour. The crude product obtained by concentrating the reaction liquid under reduced pressure was purified by silica gel column chromatography (developing solvent: hexane/ethyl acetate) and then recrystallized from ethanol to obtain 2.4 g of Compound (3-C).

Synthesis of Compound (3)

96 mg of Compound (3-C), 64 mg of 2,4,6-trimethylphenylboronic acid, 130 mg of cesium fluoride, and 10 mL of methoxycyclopentane were introduced into a 100 mL three-neck flask, followed by degassing under reduced pressure while stirring at room temperature, and the reaction system was set to a nitrogen atmosphere. 63 mg of SPhos Pd G3 (manufactured by Sigma-Aldrich, Inc.) was added thereto, followed by heating under reflux for 1 hour. 10 mL of a saturated aqueous ammonium chloride solution and 10 mL of ethyl acetate were added, and an organic layer obtained by extraction and liquid separation was preliminarily dried over anhydrous sodium sulfate and then concentrated under reduced pressure. The resulting crude product was purified by preparative TLC (developing solvent: hexane/ethyl acetate) and then recrystallized from ethanol to obtain 16 mg of Compound (3). Identification of the compound was carried out by $^1$H-NMR and ESI-MS.

$^1$H NMR (CDCl$_3$, 400 MHz): δ 8.02 (s, 1H), 8.00 (s, 2H), 7.42 (d, J=22.4 Hz, 2H), 6.92 (s, 4H), 6.80 (s, 4H), 6.67 (d, J=22.4 Hz, 2H), 2.27 (s, 6H), 2.17 (s, 6H), 2.16 (s, 6H), 2.11 (s, 12H), 2.01 (s, 12H).

ESI-MS: [M−H]$^-$=955.8

<Synthesis of Compound (2)>

The synthesis was carried out in the same manner as in the synthesis of Compound (3), except that 3,5-bis(trifluoromethyl)benzaldehyde was replaced by 2,3,4,5,6-pentafluorobenzaldehyde and 2,4-dimethylpyrrole was replaced by 2,4-dimethyl-3-ethylpyrrole. The resulting crude product was purified by silica gel column chromatography (developing solvent: hexane/ethyl acetate) and then recrystallized from dichloromethane/methanol to obtain 8 mg of Compound (2). Identification of the compound was carried out by $^1$H-NMR measurement, thus confirming the same NMR spectrum as in Org. Biomol. Chem., 2010, Vol. 8, pp. 4546 to 4553.

<Synthesis of Compound (4)>

Compound (4) was synthesized in the same manner as in the synthesis of Compound (2), except that 2,4,6-trimethylbenzaldehyde was replaced by o-tolualdehyde. Identification of the compound was carried out by $^1$H-NMR and ESI-MS. A 400 MHz $^1$H-NMR spectrum is shown in FIG. 1.

ESI-MS: [M−H]$^-$=673.3

<Synthesis of Compound (5)>

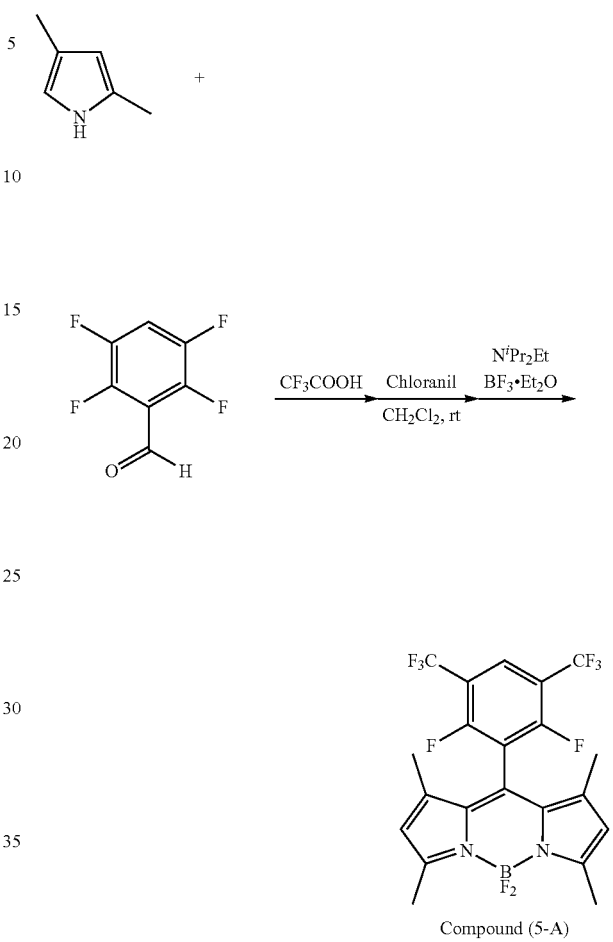

Compound (5-A)

Synthesis of Compound (5-A)

1.16 ml of 2,4-dimethylpyrrole and 140 mL of dichloromethane were introduced into a 500 mL three-neck flask under a nitrogen atmosphere, followed by stirring at room temperature. 1.0 g of 2,3,5,6-tetrafluorobenzaldehyde and one drop of trifluoroacetic acid were added, followed by stirring at room temperature for 15 minutes. 1.38 g of chloranil was added, followed by stirring at room temperature for 15 minutes, and then 6.8 mL of diisopropylethylamine (N$^i$Pr$_2$Et) was added dropwise while cooling with water, followed by stirring at room temperature for 20 minutes. Subsequently, 7.8 mL of a boron trifluoride-diethyl ether complex (BF$_3$.Et$_2$O) was added dropwise while cooling with water, followed by stirring at room temperature for 30 minutes. 400 mL of saturated sodium hydrogen carbonate was added dropwise, and an organic layer obtained by dichloromethane extraction and liquid separation was preliminarily dried over anhydrous sodium sulfate and then concentrated under reduced pressure. The resulting crude product was purified by silica gel column chromatography (developing solvent: hexane/ethyl acetate) and then recrystallized from methanol to obtain 360 mg of Compound (5-A).

Synthesis of Compound (5-B)

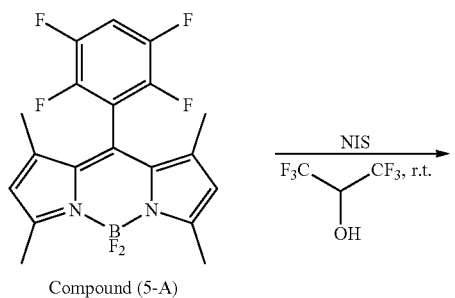

300 mg of Compound (5-A) and 8 mL of 1,1,1,3,3,3-hexafluoro-2-propanol were introduced into a 300 mL three-neck flask, followed by stirring at room temperature. 409 mg of N-iodosuccinimide was introduced, followed by stirring at room temperature for 1.5 hours. After concentrating the reaction liquid under reduced pressure, 40 mL of methylene chloride was added, and an organic layer obtained by extraction and liquid separation was preliminarily dried over anhydrous sodium sulfate, filtered, and concentrated under reduced pressure. Ethanol was added to the resulting crude product, followed by dispersion, washing, and filtration to obtain 382 mg of Compound (5-B).

Synthesis of Compound (5-C)

278 mg of Compound (5-B), 564 mg of 2,4,6-trimethylphenylboronic acid, 653 mg of cesium fluoride, and 43 mL of methoxycyclopentane were introduced into a 100 mL three-neck flask, followed by degassing under reduced pressure while stirring at room temperature, and the reaction system was set to a nitrogen atmosphere. 269 mg of SPhos Pd G3 (manufactured by Sigma-Aldrich, Inc.) was added thereto, followed by heating under reflux for 1 hour. 250 mL of ethyl acetate was added, and an organic layer obtained by extraction and liquid separation was preliminarily dried over anhydrous sodium sulfate and then concentrated under reduced pressure. The resulting crude product was purified by silica gel column chromatography (developing solvent: hexane/ethyl acetate) and then dissolved in 5 ml of dichloromethane, 15 ml of methanol was further added, and then dichloromethane was distilled off, followed by reprecipitation. The precipitate was filtered to obtain 206 mg of Compound (5-C).

Synthesis of Compound (5)

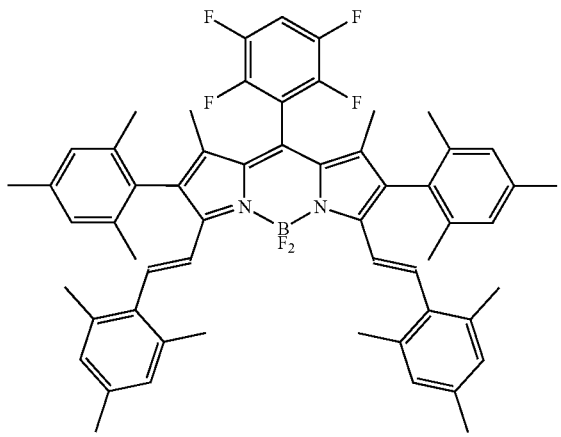

Compound (5)

50 mg of Compound (5-C), 5 ml of toluene, 46 µl of 2,4,6-trimethylbenzaldehyde, 400 µl of piperidine, and one piece of p-toluenesulfonic acid were introduced into a 100 mL three-neck flask, followed by heating under reflux under nitrogen for 1 hour. After further adding 46 µl of 2,4,6-trimethylbenzaldehyde, followed by heating under reflux for 1 hour, 200 µl of piperidine was further added, followed by heating under reflux for another 1 hour. After completion of the reaction, the reaction liquid was concentrated under reduced pressure. The resulting crude product was purified by silica gel column chromatography (developing solvent: hexane/toluene) and then dissolved in 3 ml of dichloromethane, 15 ml of methanol was added, and then dichloromethane was distilled off, followed by reprecipitation to obtain 16 mg of Compound (5). Identification of the compound was carried out by $^1$H-NMR and ESI-MS.

$^1$H NMR (CDCl$_3$, 400 MHz): δ 7.43 (s, 1H), 7.39 (s, 1H), 7.29-7.21 (m, 1H), 6.94 (s, 4H), 6.80 (s, 4H), 6.69 (s, 1H), 6.65 (s, 1H), 2.29 (s, 6H), 2.23 (s, 6H), 2.08 (s, 12H), 2.03 (s, 12H), 1.33 (s, 6H).

ESI-MS: [M–H]$^-$=891.4

<Synthesis of Compound (6)>

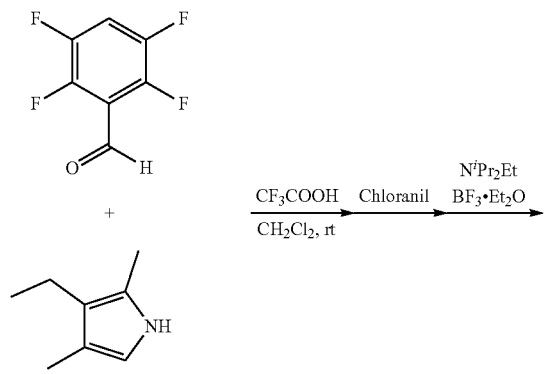

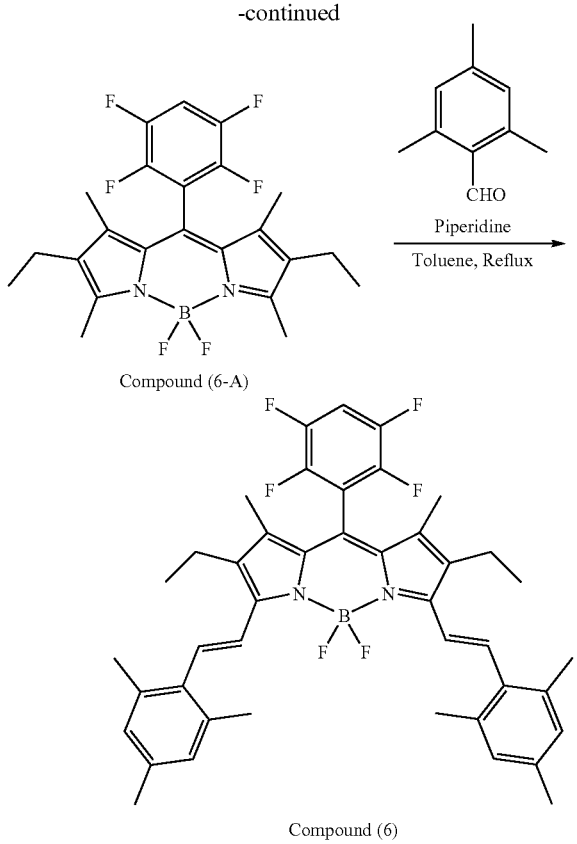

Compound (6)

Synthesis of Compound (6-A)

1.00 g of 2,3,5,6-tetrafluorobenzaldehyde and 20 mL of dichloromethane were introduced into a 100 mL three-neck flask under a nitrogen atmosphere, followed by stirring at room temperature. 0.98 g of 3-ethyl-2,4-dimethylpyrrole was added dropwise while cooling with water, followed by addition of two drops of trifluoroacetic acid and then stirring at room temperature for 15 minutes. 1.0 g of chloranil was added while cooling with water, followed by stirring at room temperature for 10 minutes, and 3.67 g of diisopropylethylamine was added dropwise while cooling with water, followed by stirring at room temperature for 15 minutes. Subsequently, 5.6 mL of a boron trifluoride-diethyl ether complex was added dropwise while cooling with water, followed by stirring at room temperature for 60 minutes. Saturated sodium hydrogen carbonate and toluene were added dropwise, and an organic layer obtained by extraction and liquid separation was preliminarily dried over anhydrous sodium sulfate and then concentrated under reduced pressure. The resulting crude product was purified by silica gel column chromatography (developing solvent: toluene) and then recrystallized from methanol to obtain 0.76 g of Compound (6-A).

$^1$H NMR (CDCl$_3$, 400 MHz): δ 7.20-7.30 (m, 1H), 2.54 (s, 6H), 2.33 (q, J=7.6 Hz, 4H), 1.51 (s, 6H), 1.01 (t, J=7.6 Hz, 6H).

Synthesis of Compound (6)

181 mg of Compound (6-A), 237 mg of 2,4,6-trimethylbenzaldehyde, and 10 mL of dehydrated toluene were introduced into a 100 mL three-neck flask, followed by stirring at room temperature. 2 mL of piperidine and two pieces of p-toluenesulfonic acid monohydrate (manufactured by Wako Pure Chemical Industries, Ltd., special grade chemical) were added, followed by stirring for 1 hour while distilling off the solvent at 140° C. The crude product obtained by concentrating the reaction liquid under reduced pressure was purified by silica gel column chromatography (developing solvent: toluene) and then recrystallized from acetonitrile to obtain 194 mg of Compound (6). Identification of the compound was carried out by $^1$H-NMR and ESI-MS.

$^1$H NMR (CDCl$_3$, 400 MHz): δ 7.40 (d, J=17.2 Hz, 2H), 7.32 (d, J=17.2 Hz, 2H), 7.20-7.30 (m, 1H), 6.93 (s, 4H), 2.66 (q, J=7.6 Hz, 4H), 2.44 (s, 12H), 2.30 (s, 6H), 1.55 (s, 6H), 1.19 (t, J=7.6 Hz, 6H).

ESI-MS: [M−H]$^−$=711.7

<Synthesis of Compound (7)>

Figure 2:
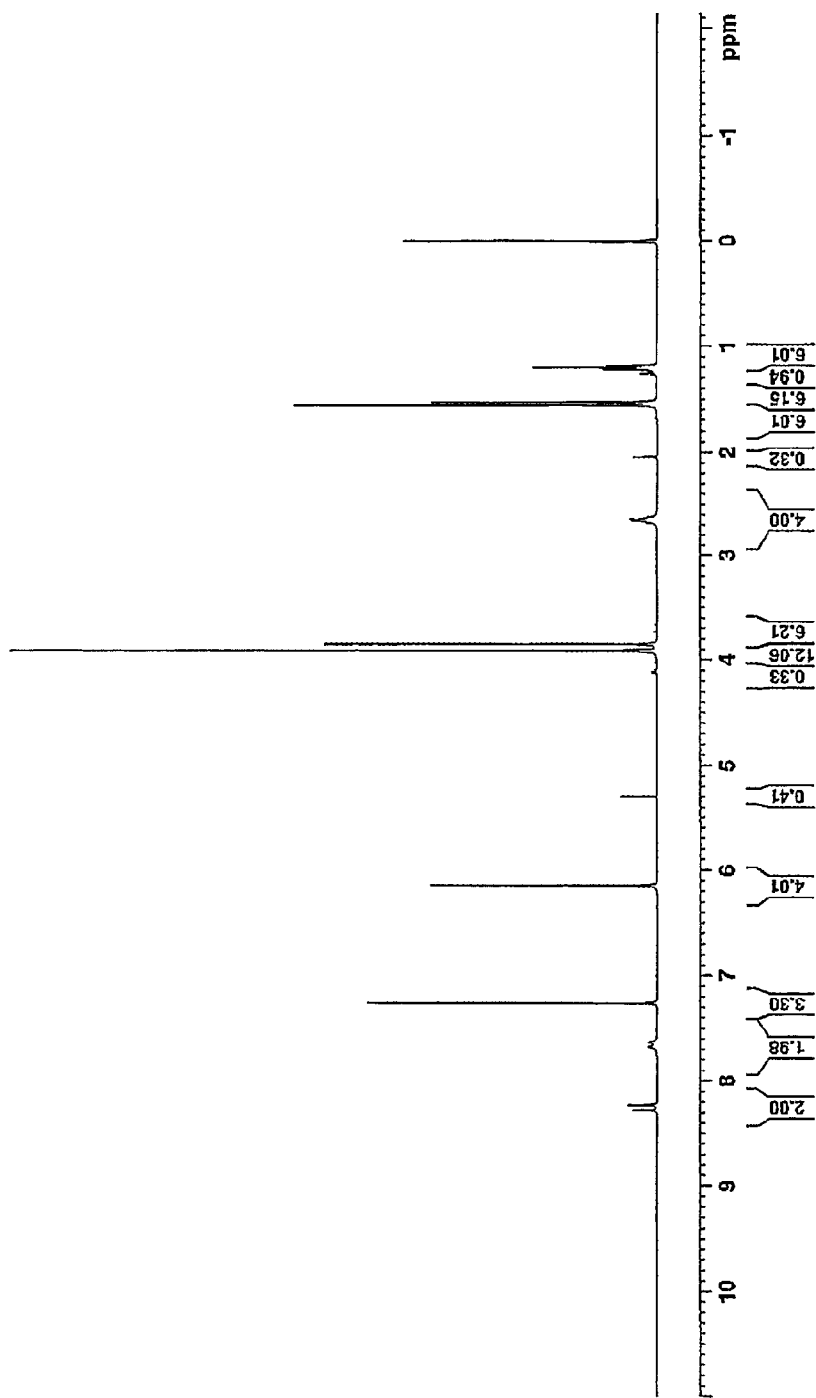
FIG. 2 shows a 400 MHz $^1$H NMR spectrum of Compound (7).

Compound (7) was synthesized in the same manner as in the synthesis of Compound (2), except that 2,4,6-trimethylbenzaldehyde was replaced by 2,4,6-trimethoxybenzaldehyde. Identification of the compound was carried out by $^1$H-NMR and ESI-MS. A 400 MHz $^1$H-NMR spectrum is shown in FIG. 2.

ESI-MS: [M+H]$^+$=825.3

<Synthesis of Compound (8)>

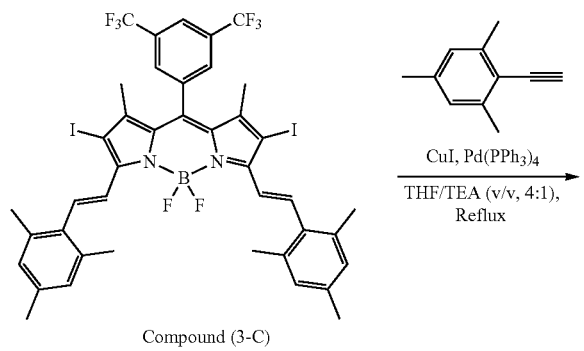
Compound (3-C)

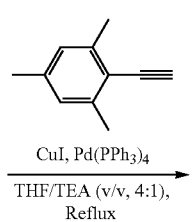

CuI, Pd(PPh$_3$)$_4$
THF/TEA (v/v, 4:1), Reflux

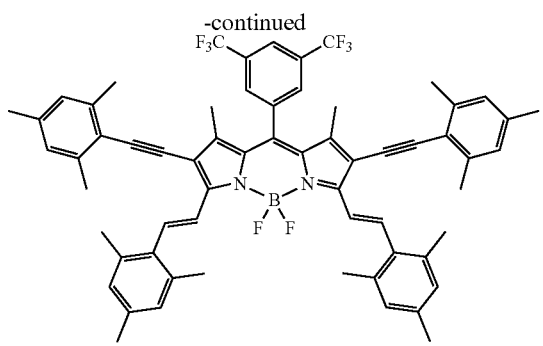
Compound (8)

Synthesis of Compound (8)

97 mg of Compound (3-C), 58 mg of 2-ethynyl-1,3,5-trimethylbenzene, 3.8 mg of copper(I) iodide, 4 mL of THF, and 1 mL of triethylamine were introduced into a 50 mL two-neck flask, followed by degassing under reduced pressure while stirring at room temperature, and the reaction system was set to a nitrogen atmosphere. Tetrakis(triphenylphosphine)palladium (0) (Pd(PPh$_3$)$_4$) was added thereto, followed by heating under reflux for 2 hours. The solvent was removed by distillation under reduced pressure, and 30 mL of dichloromethane was added thereto, followed by washing with 20 mL of water and 20 mL of a saturated aqueous sodium chloride solution. An organic layer was preliminarily dried over anhydrous sodium sulfate and concentrated under reduced pressure. The resulting crude product was purified by silica gel column chromatography (developing solvent: hexane/toluene) and then recrystallized from methanol to obtain 26 mg of Compound (8). Identification of the compound was carried out by $^1$H-NMR and ESI-MS.

$^1$H NMR (CDCl$_3$, 400 MHz): δ 8.60 (s, 1H), 8.56 (s, 1H), 8.09 (s, 1H), 7.90 (s, 2H), 7.41 (s, 1H), 7.37 (s, 1H), 6.88 (s, 4H), 6.85 (s, 4H), 2.36 (s, 12H), 2.34 (s, 12H), 2.28 (s, 6H), 2.27 (s, 6H).

ESI-MS: [M−H]$^−$=1003.5

<Synthesis of Compound (9)>

Compound (9) was synthesized in the same manner as in the method for synthesizing Compound (5) through Compounds (5-A) to (5-C), except that 2,4,6-trimethylbenzaldehyde in the synthesis of Compound (5) was replaced by benzaldehyde.

<Synthesis of Compound (10)>

Compound (10) was synthesized in the same manner as in the method for synthesizing Compound (5) through Compounds (5-A) to (5-C), except that 2,3,5,6-tetrafluorobenzaldehyde in the synthesis of Compound (5-A) was replaced by 2,4,6-trimethylbenzaldehyde.

<Synthesis of Compound (11)>

Compound (11) was synthesized in the same manner as in the method for synthesizing Compound (5) through Compounds (5-A) to (5-C), except that 2,4,6-trimethylbenzaldehyde in the synthesis of Compound (5) was replaced by 2-formylnaphthalene.

<Synthesis of Compound (12)>

Compound (12) was synthesized in the same manner as in the method for synthesizing Compound (5) through Compounds (5-A) to (5-C), except that 2,4,6-trimethylbenzaldehyde in the synthesis of Compound (5) was replaced by 2,6-dimethoxybenzaldehyde.

<1-2> Preparation of High Luminescent Fluorescent Latex Dispersion Liquid

Fluorescent latex particles were prepared. As the latex particles, particles having an average particle diameter of 150 nm prepared by polymerization in a state that a 9/1 (mass ratio) mixture of styrene and acrylic acid was dispersed in water were used. The average particle diameter was measured by a dynamic light scattering method. THF (5 mL) was added dropwise to the above-prepared latex particle dispersion liquid having a solid content of 2% (25 mL of latex dispersion, 500 mg of solid), followed by stirring for 10 minutes. A THF solution (2.5 mL) containing 24 µmol/g of Compound (1) was added thereto dropwise over 15 minutes. Regarding the amount of compound in a table, µmol/g represents the number of moles of the compound used per 1 g of solids in the latex, and % by mass represents the % by mass of the compound used per 1 g of solids in the latex. Completion of the dropwise addition of the compound was followed by stirring for 30 minutes and concentrating under reduced pressure to remove THF. Thereafter, the particles were precipitated by centrifugation, followed by addition of ultrapure water, and then dispersed again to produce a high luminescent fluorescent latex dispersion liquid having a solid content concentration of 2%.

Further, the same operation was performed using Compound (5) instead of Compound (1) to produce a high luminescent fluorescent latex dispersion liquid having a solid content concentration of 2% containing Compound (5).

Furthermore, the same operation was performed using a mixture of 24 µmol/g of Compound (1) and 12 µmol/g of Compound (5) to produce a high luminescent fluorescent latex dispersion liquid having a solid content concentration of 2% containing Compound (1) and Compound (5).

<2-1> Preparation of Fluorescent Particles Labeled with Anti-Progesterone Antibody High luminescent fluorescent latex particles (average particle diameter of 150 nm) labeled with anti-progesterone antibody were prepared as follows.

117 µL of a buffer solution (pH of 6.0) of 50 mM 2-morpholinoethanesulfonic acid (MES, manufactured by Dojindo Molecular Technologies, Inc.) and 5 µL of an aqueous solution of 10 mg/mL water-soluble carbodiimide (WSC) were added to 375 µL of a high luminescent fluorescent latex dispersion liquid having a solid content concentration of 2% by mass prepared in <1-2>, followed by stirring at room temperature for 15 minutes. Subsequently, 182.4 µL of a 0.5 mg/mL anti-progesterone monoclonal antibody (manufactured by GeneTex, Inc.) was added, followed by stirring at room temperature for 1.5 hours. 37.5 µL of an aqueous solution of 2 mol/L glycine (manufactured by Wako Pure Chemical Industries, Ltd.) was added, followed by stirring for 15 minutes, and then the fluorescent latex particles were precipitated by centrifugation (15,000 rpm, 4° C., 30 minutes). A supernatant liquid was removed, 750 µL of a phosphate buffered saline (PBS, manufactured by Wako Pure Chemical Industries, Ltd.) solution (pH of 7.4) was added, and the fluorescent latex particles were re-dispersed with an ultrasonic cleaner. Centrifugation (15,000 rpm, 4° C., 15 minutes) was performed, a supernatant liquid was removed, followed by addition of 750 µL of a PBS (pH of 7.4) solution containing 1% by mass of BSA, and then the fluorescent latex particles were re-dispersed to obtain a solution of 1 mass % anti-progesterone antibody-bound fluorescent latex particles.

<2-2> Preparation of Solution of Progesterone-BSA Conjugate in Citrate Buffer Solution 150 µg of a progesterone-BSA conjugate (manufactured by Bio-Rad Laboratories, Inc.) was added to and dissolved in 1 mL of a citrate buffer solution at a concentration of 50 mM (pH of 5.2, 150 mM NaCl), thereby obtaining a solution of a citrate buffer solution.

<2-3> Production of Progesterone-BSA Conjugate-Immobilized Substrate

A polymethyl methacrylate (PMMA) substrate (manufactured by Mitsubishi Rayon Co., Ltd., ACRYPET (registered trademark) VH) was prepared, a gold film having thickness of 50 nm was deposited on one side thereof by a vapor deposition method, and the resultant is cut to a width of 7 mm is performed to prepare seven identical substrates. The solution of the progesterone-BSA conjugate in the citrate buffer solution prepared in 1. was spotted on a gold-deposited surface of the substrate, and dried to prepare a substrate on which the progesterone-BSA conjugate is immobilized.

<2-4> Washing and Blocking of Substrate

Before the substrate prepared in this manner is attached to a flow channel of a sensor chip, a PBS solution (pH of 7.4) containing Tween 20 (polyoxyethylene (20) sorbitan monolaurate, Wako Pure Chemical Industries, Ltd.) at a concentration of 0.05% by mass was prepared in advance, and the substrate was repeatedly washed three times with 300 µL of the solution. After completion of the washing, in order to block a portion which was not adsorbed with the T4-BSA conjugate, on the gold-deposited film, 300 µL of a PBS solution (pH of 7.4) containing 1% by mass of casein (manufactured by Thermo Fisher Scientific Inc.) was added, followed by being left to stand for 1 hour at room temperature. After washing with the solution for washing, 300 µL of Immunoassay Stabilizer (manufactured by Advanced Biotechnologies Inc.) was added as a stabilizer, followed by being left to stand for 30 minutes at room temperature. Then, the solution was removed and moisture was completely removed using a dryer.

<2-5> Preparation of Sensor Chip

Figure 3:
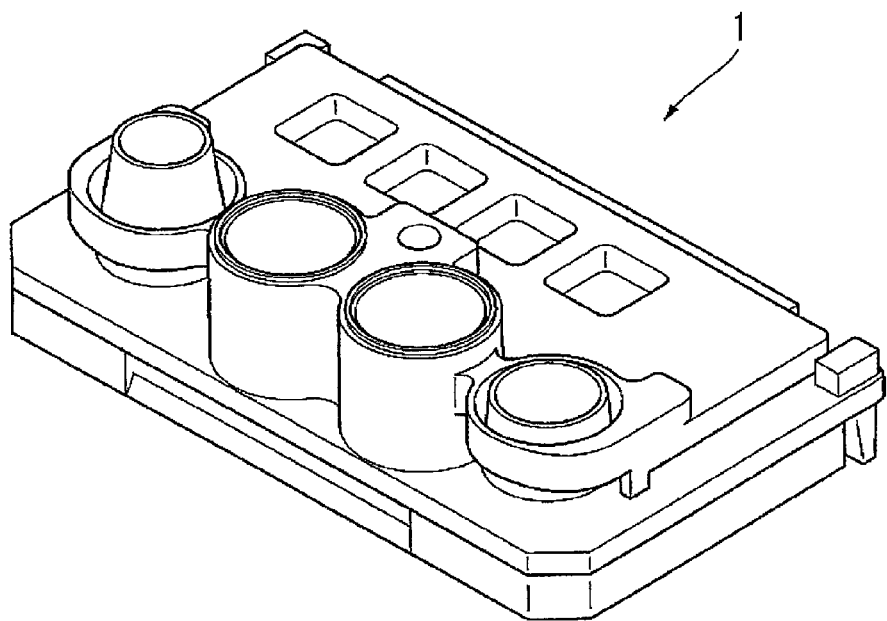
FIG. 3 shows a schematic view of a sensor chip.
Figure 4:
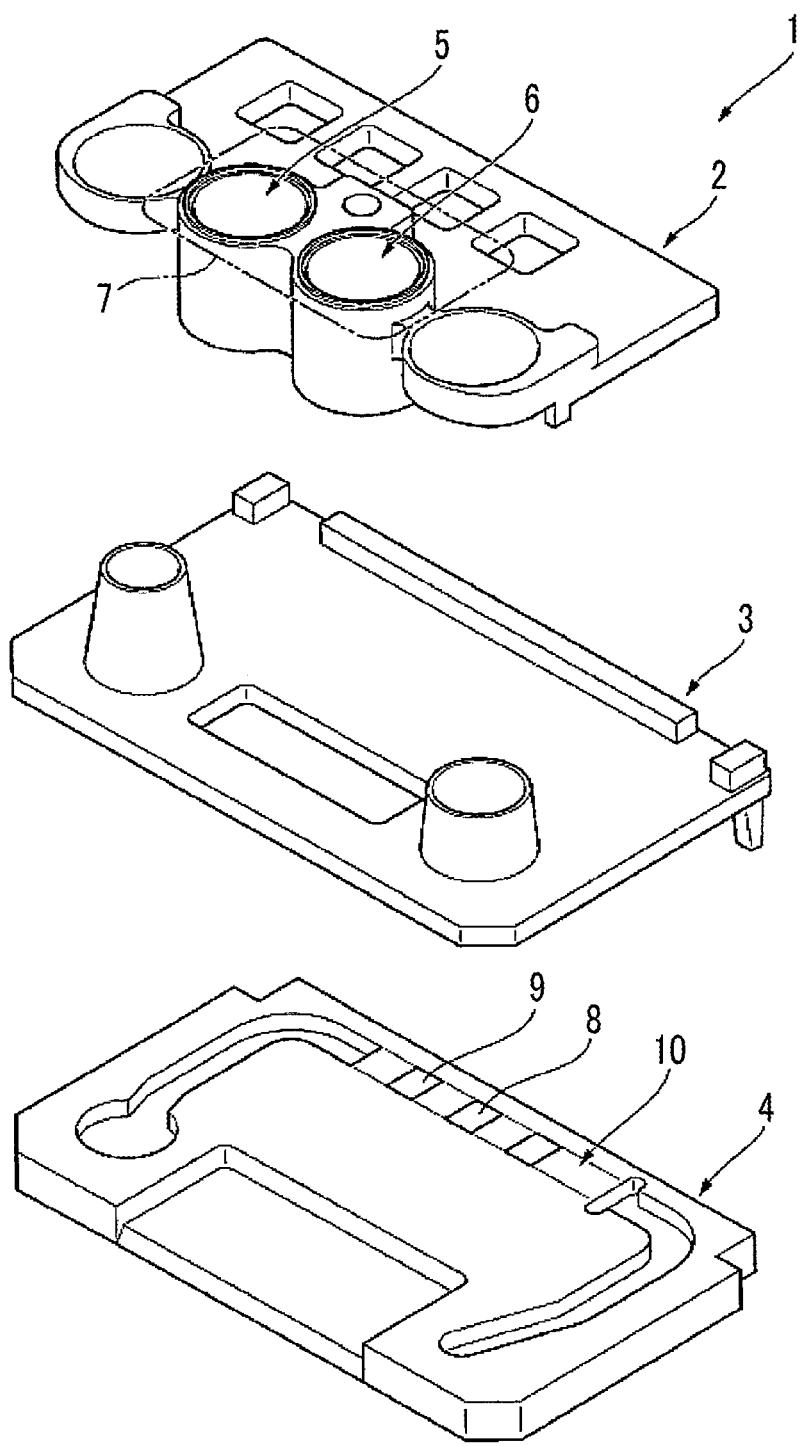
FIG. 4 shows an exploded view of the sensor chip.

A flow channel-type sensor chip was prepared to have the configuration of the second embodiment in JP2010-190880A. The schematic views thereof are shown in FIG. 3 and FIG. 4. FIG. 3 is a schematic view of a sensor chip 1, and FIG. 4 is an exploded view of the sensor chip 1. The sensor chip 1 includes an upper member 2, an intermediate member 3, and a substrate 4. The upper member 2 is provided with a first container 5 and a second container 6. The first container 5 and the second container 6 are collectively referred to as a container group 7. A flow channel 10 is formed in the substrate 4, and a detection area 8 and a reference area 9 are formed on the flow channel 10.

<3-1> Measurement with Large-Scale Apparatus (Pre-Existing Progesterone Measurement Reagent)

In immunoassay, measurement of a sample in which an amount of progesterone is known was performed by using IMMULYZE 1000 (LSI Medience Corporation), which is a large-scale apparatus widely used by those skilled in the art and according to the instruction manual, and measured values of progesterone were obtained.

<3-2> Measurement of Progesterone Using Antibody-Labeled Particles

Samples containing progesterone having various concentrations (0.00 ng/mL, 0.5 ng/mL, 2.0 ng/mL, 15.0 ng/mL, 30.0 ng/mL, and 45.0 ng/mL) were prepared. Next, a plurality of cups for antibody-labeled particle concentrations were prepared so that concentrations of antibody-labeled particles became 0.080%, 0.040%, 0.020%, 0.010%, 0.005%, 0.002%, and 0.001% at a time of preparing liquid mixtures of the antibody-labeled particles labeled with anti-progesterone antibody prepared in <2-1> and the various samples, the samples having various concentrations prepared above were added to the cups for respective concentrations, and while stirring for 10 minutes, the liquid mixtures of the antibody-labeled particles and the samples were prepared. Then, on the flow channel-type sensor chip in which the substrate was sealed, prepared in 2-5, the liquid mixtures of the antibody-labeled particles and the samples were respectively spotted. After spotting was completed, the liquid mixtures were allowed to flow down at a rate of 10 µL/min while pump suction was performed, and brought into contact with the surface of the gold film on which the progesterone-BSA conjugate was immobilized, and then the measurement of fluorescence intensity was continued for 1.5 minutes. Standardization was performed by acquiring an increase rate in the unit time of the fluorescence intensity of each of the detection area and the reference area obtained in each substrate, as a fluorescence signal value, and dividing the signal value of the detection area by the signal value of the reference area. In addition, a sample with a progesterone concentration of zero was prepared, and in the same manner as described above, standardization of a signal value from a sample without progesterone was performed.

<4> Creation of Calibration Curve

By acquiring the correlation between the fluorescence signal value standardized from the sample with the known amount of progesterone obtained in <3-2> and the value measured with the large-scale apparatus acquired in <3-1>, a calibration curve was created for the substrate using the progesterone-BSA conjugate prepared in <2-2>. Literature "The Immunoassay Handbook Third Edition Edited by David Wild (2005)" describes that a four-parameter logistic curve model of a sigmoid function can be applied as a calibration curve of a competition method, and according to this method, a four-parameter logistic curve passing the nearest neighbor of each point of the fluorescence signal values at the respective progesterone concentrations measured in 3-2. was acquired using the least squares method generally known as a method for obtaining an approximate line, and the curve was set as a calibration curve.

From the calibration curve acquired as described above, the measured value of the sample with each progesterone concentration was calculated.

The performance was determined according to whether to satisfy the standard of the calibration curve. The calibration curve was defined by two points. A first point was a slope of the calibration curve in a low concentration range, and a case where a reciprocal of the slope is within 2.0 was set as a standard. A second point was a deviation from the calibration curve at the measurement point in a high concentration range, and a case where the deviation was within 4% was set as a standard. Within this range, it is possible to achieve the coefficient of variation of the measured value within 10% and the accuracy within 10%, and to perform the high-precision measurement.

In the case of the low concentration range, a slope of a calibration curve at 0.5 ng/mL as the minimum concentration of progesterone which is clinically meaningful was acquired. In addition, in the case of the high concentration range, deviations from respective calibration curves at progesterone concentrations of 30.0 ng/mL and 45.0 ng/mL were acquired, and an average value thereof was calculated and evaluated. The results are summarized in Table 3.

<5> Preparation of Comparative Particles

<5-1> Preparation of Comparative Fluorescent Latex Particle Dispersion Liquid 100 mL of methanol was added to 100 mL of an aqueous dispersion liquid having the solid content concentration of the latex particle dispersion liquid prepared in <1-2> of 2% by mass, followed by stirring at room temperature for 10 minutes. On the other hand, a separately prepared fluorescent dye (comparative compound: Compound 5 described in JP3442777B) solution (dissolved in 1 mL of N,N-dimethylformamide, 9 mL of $CHCl_3$, and 16 mL of ethanol) was gradually added dropwise into the latex particle dispersion liquid over 60 minutes. After completion of the dropwise addition, an organic solvent was distilled off under reduced pressure with an evaporator, and then centrifugation and redispersion in an aqueous PBS solution were repeated three times to perform purification, thereby preparing a comparative fluorescent latex particle dispersion liquid.

<5-2> Preparation of Comparative Antibody-Labeled Particles Labeled with Anti-Progesterone Antibody In the preparation of the fluorescent latex particles prepared in <2-1>, the fluorescent latex particles were replaced by the comparative fluorescent latex particles of 2% by mass (solid content concentration) prepared in <5-1>, and other operations were performed in the same manner to prepare comparative antibody-labeled particles. The other operations were carried out in the same manner to the measurement of <4>.

<6> Measurement of Particle Fluorescence Intensity

The fluorescence latex dispersion liquid having a solid content concentration of 2% by mass was diluted 200 times with ultrapure water, the excitation light of a fluorescence spectrophotometer RF-5300PC (manufactured by Shimadzu Corporation) was set to 658 nm, and measurement was performed. In the case where the fluorescence intensity of the fluorescent latex dispersion liquid was high enough to exceed the measurement range, dilution was performed with ultrapure water to a range in which the maximum value of the fluorescence intensity was measurable. An integrated value of the fluorescence intensity of the emission spectrum of the fluorescent latex dispersion liquid with respect to an integrated value of the fluorescence intensity of the emission spectrum of the fluorescent latex dispersion liquid prepared in 7-1. was taken as the particle fluorescence intensity (relative value). A calculation expression used for the calculation is shown below.

Fluorescence intensity (relative value)=(Integrated value of fluorescence intensity of emission spectrum of fluorescent latex dispersion liquid)/(Integrated value of fluorescence intensity of emission spectrum of fluorescent latex dispersion liquid prepared in Comparative example)

<Evaluation Standards>

The determination was set as A in the case where the reciprocal of the slope of the calibration curve in the low concentration range was 2.0 or less, and the determination was set as B in the case where the reciprocal thereof was larger than 2.0.

The determination was set as A in the case where the deviation from the calibration curve in the high concentration range was 4% or less, and the determination was set as B in the case where the deviation therefrom was larger than 4%.

TABLE 3

| | Compound | Particle concentration | Particle fluorescence intensity (relative value) | Reciprocal of slope of calibration curve in low concentration range | Determination | Deviation from calibration curve in high concentration range | Determination |
|---|---|---|---|---|---|---|---|
| Example 1 | (1), (5) | 0.080% by mass | 12.1 | 1.7 | A | 1.8% | A |
| Example 2 | (1), (5) | 0.040% by mass | 12.1 | 1.6 | A | 1.9% | A |
| Example 3 | (1), (5) | 0.020% by mass | 12.1 | 1.5 | A | 2.0% | A |
| Example 4 | (1), (5) | 0.010% by mass | 12.1 | 1.4 | A | 2.4% | A |
| Example 5 | (1), (5) | 0.005% by mass | 12.1 | 1.3 | A | 2.9% | A |
| Example 6 | (1), (5) | 0.002% by mass | 12.1 | 1.2 | A | 3.3% | A |
| Example 7 | (1), (5) | 0.001% by mass | 12.1 | 1.1 | A | 3.4% | A |
| Example 8 | (1) | 0.080% by mass | 5.8 | 2.0 | A | 2.0% | A |
| Example 9 | (1) | 0.040% by mass | 5.8 | 1.9 | A | 2.4% | A |
| Example 10 | (1) | 0.020% by mass | 5.8 | 1.8 | A | 2.8% | A |
| Example 11 | (1) | 0.010% by mass | 5.8 | 1.7 | A | 3.2% | A |
| Example 12 | (1) | 0.005% by mass | 5.8 | 1.6 | A | 3.4% | A |
| Example 13 | (1) | 0.002% by mass | 5.8 | 1.5 | A | 3.6% | A |
| Example 14 | (1) | 0.001% by mass | 5.8 | 1.4 | A | 3.8% | A |
| Example 15 | (5) | 0.080% by mass | 7.0 | 1.9 | A | 1.9% | A |
| Example 16 | (5) | 0.040% by mass | 7.0 | 1.8 | A | 2.2% | A |
| Example 17 | (5) | 0.020% by mass | 7.0 | 1.7 | A | 2.5% | A |
| Example 18 | (5) | 0.010% by mass | 7.0 | 1.6 | A | 3.1% | A |
| Example 19 | (5) | 0.005% by mass | 7.0 | 1.5 | A | 3.3% | A |
| Example 20 | (5) | 0.002% by mass | 7.0 | 1.4 | A | 3.5% | A |
| Example 21 | (5) | 0.001% by mass | 7.0 | 1.3 | A | 3.6% | A |
| Comparative Example 1 | Comparative compound | 0.080% by mass | 1.0 | 3.8 | B | 2.0% | A |
| Comparative Example 2 | Comparative compound | 0.040% by mass | 1.0 | 2.0 | A | 4.1% | B |
| Comparative Example 3 | Comparative compound | 0.020% by mass | 1.0 | 1.9 | A | 4.5% | B |
| Comparative Example 4 | Comparative compound | 0.010% by mass | 1.0 | 1.8 | A | 5.2% | B |
| Comparative Example 5 | Comparative compound | 0.005% by mass | 1.0 | 1.7 | A | 7.2% | B |
| Comparative Example 6 | Comparative compound | 0.002% by mass | 1.0 | 1.6 | A | 9.0% | B |
| Comparative Example 7 | Comparative compound | 0.001% by mass | 1.0 | 1.5 | A | 10.2% | B |

As shown in the results in Table 3, in the particles of Comparative examples having low particle fluorescence intensity, in the case where the particle concentration was high, the slope of the calibration curve in the low concentration range could not be obtained and in the case where the particle concentration was low, the deviation from the calibration curve in the high concentration range became large. Therefore, there is no condition in which the measurement with high precision could be performed over the entire measurement range. In contrast, it was found that the high luminescent fluorescent particles of the present invention can be measured with high precision over the entire measurement range, and the effect of the present invention was confirmed.

EXPLANATION OF REFERENCES

1 Sensor chip
2 Upper member
3 Intermediate member
4 Substrate
5 First container
6 Second container
7 Container group
8 Detection area
9 Reference area
10 Flow channel

What is claimed is:

1. A kit for measuring a measurement target substance in a biological sample, the kit comprising:
   a labeled particle having a first binding substance capable of binding to a measurement target substance in a biological sample; and
   a substrate having a second binding substance capable of binding to any one of the measurement target substance or the first binding substance,
   wherein the labeled particle is a luminescent labeled particle containing at least one kind of compound represented by Formula (1) and a particle,

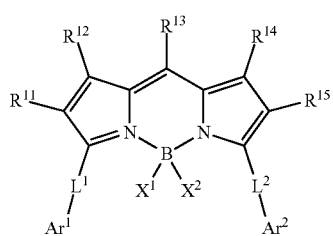

(1)

in the formula, both $R^{11}$ and $R^{15}$ are ethyl; phenyl which has methyl; or ethynyl which has phenyl having methyl; $R^{12}$ and $R^{14}$ each represents methyl; $R^{13}$ represents a phenyl having trifluoromethyl, fluorine atom or methyl; $X^1$ and $X^2$ each represents a fluorine atom; both $Ar^1$ and $Ar^2$ are a phenyl group, a naphthyl group, or a phenyl group which has a methyl or methoxy; and $L^1$ and $L^2$ represent Formula (L-1),

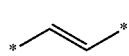

Formula (L-1)

with the proviso that the following Compound (2) is excluded from the compounds represented by Formula (1):

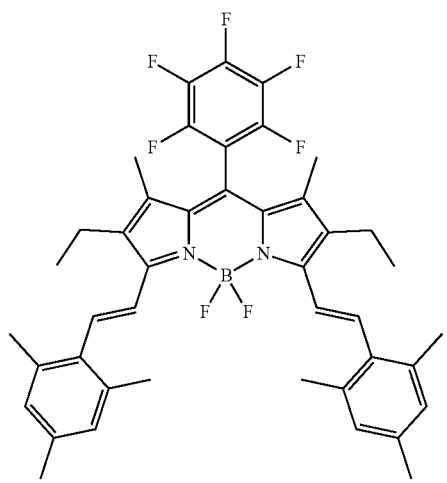

Compound (2)

2. The kit according to claim 1, wherein the labeled particle is a labeled latex particle.

3. The kit according to claim 1, wherein the labeled particle has a carboxyl group.

4. The kit according to claim 1, wherein an average particle size of the labeled particle is 70 to 500 nm.

5. The kit according to claim 1, wherein in Formula (1), both $R^{11}$ and $R^{15}$ are a phenyl group which has a methyl, or an ethynyl group which has a phenyl having a methyl.

6. The kit according to claim 1, wherein the labeled particle is a luminescent particle containing at least one kind of energy donor compound, at least one kind of energy acceptor compound, and a particle, and at least one kind of the energy donor compound or the energy acceptor compound is the compound represented by Formula (1).

7. The kit according to claim 6, wherein at least one kind of compound represented by Formula (1) is contained as the energy donor compound, and at least one kind of compound represented by Formula (1) is contained as the energy acceptor compound.

8. The kit according to claim 6, wherein a molar ratio of the energy donor compound to the energy acceptor compound is 1:10 to 10:1.

9. The kit according to claim 6, wherein a Stokes shift between the energy donor compound and the energy acceptor compound is 40 nm or more.

10. The kit according to claim 1, wherein the substrate includes a detection area having the second binding substance.

11. The kit according to claim 10, wherein the detection area is a metal film containing gold.

12. A method for measuring a measurement target substance in a biological sample, the method comprising:
    a reaction step of reacting a biological sample with a labeled particle having a first binding substance capable of binding to a measurement target substance;
    a capturing step of capturing the labeled particle on a substrate having a second binding substance capable of binding to any one of the measurement target substance or the first binding substance by bringing a reaction product obtained in the reaction step into contact with the substrate; and
    a label information acquisition step of acquiring label information related to the measurement target substance,
    wherein the labeled particle is a luminescent labeled particle containing at least one kind of compound represented by Formula (1) and a particle,

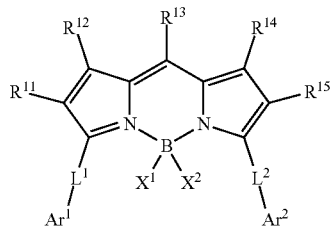

(1)

in the formula, both $R^{11}$ and $R^{15}$ are ethyl; phenyl which has methyl; or ethynyl which has phenyl having methyl; $R^{12}$ and $R^{14}$ each represents methyl; $R^{13}$ represents a phenyl having trifluoromethyl, fluorine atom or methyl; $X^1$ and $X^2$ each represents a fluorine atom; both $Ar^1$ and $Ar^2$ are a phenyl group, a naphthyl group, or a phenyl group which has a methyl or methoxy; and $L^1$ and $L^2$ represent Formula (L-1),

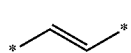

Formula (L-1)

with the proviso that the following Compound (2) is excluded from the compounds represented by Formula (1):

Compound (2)

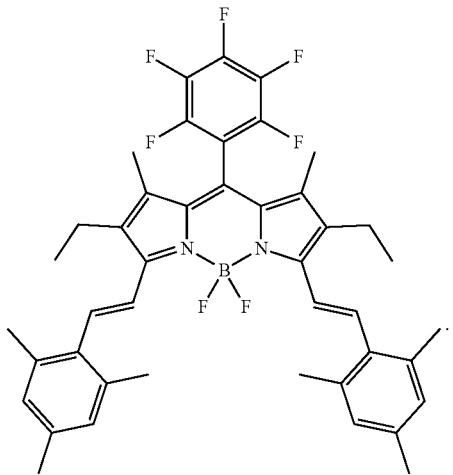

13. The method according to claim 12,
wherein the labeled particle is a luminescent particle containing at least one kind of energy donor compound, at least one kind of energy acceptor compound, and a particle, and at least one kind of the energy donor compound or the energy acceptor compound is the compound represented by Formula (1).

14. The method according to claim 13,
wherein at least one kind of compound represented by Formula (1) is contained as the energy donor compound, and at least one kind of compound represented by Formula (1) is contained as the energy acceptor compound.

15. The method according to claim 13,
wherein a molar ratio of the energy donor compound to the energy acceptor compound is 1:10 to 10:1.

16. The method according to claim 13,
wherein a Stokes shift between the energy donor compound and the energy acceptor compound is 40 nm or more.

17. The method according to claim 12,
wherein the substrate includes a detection area having the second binding substance.

18. The method according to claim 12,
wherein label information related to the measurement target substance is acquired by fluorescence detection due to surface plasmon excitation.

\* \* \* \* \*